(12) United States Patent
Michalak et al.

(10) Patent No.: US 12,260,296 B1
(45) Date of Patent: Mar. 25, 2025

(54) DIAMONDOID MATERIALS IN QUANTUM COMPUTING DEVICES

(71) Applicant: Intel Corporation, Santa Clara, CA (US)

(72) Inventors: David J. Michalak, Portland, OR (US); James Munro Blackwell, Portland, OR (US); John J. Plombon, Portland, OR (US); James S. Clarke, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 1129 days.

(21) Appl. No.: 17/124,347

(22) Filed: Dec. 16, 2020

(51) Int. Cl.
*G06N 10/40* (2022.01)
*C07C 13/615* (2006.01)
*H03K 19/195* (2006.01)
*H10N 60/12* (2023.01)
*H10N 60/80* (2023.01)
*H10N 69/00* (2023.01)

(52) U.S. Cl.
CPC ........... *G06N 10/40* (2022.01); *C07C 13/615* (2013.01); *C07C 2603/74* (2017.05); *H03K 19/195* (2013.01); *H10N 60/12* (2023.02); *H10N 60/805* (2023.02); *H10N 69/00* (2023.02)

(58) Field of Classification Search
CPC ...... G06N 10/00; G06N 10/40; C07C 13/615; C07C 2603/74; H10N 60/805; H10N 60/00; H10N 60/12; H03K 19/195
See application file for complete search history.

(56) References Cited

U.S. PATENT DOCUMENTS

| | | | | |
|---|---|---|---|---|
| 5,019,660 A * | 5/1991 | Chapman | ............... | C08G 61/00 528/392 |
| 5,053,434 A * | 10/1991 | Chapman | ............... | C08G 61/00 585/352 |
| 7,224,532 B2 * | 5/2007 | Dahl | ......................... | H01S 3/14 428/408 |
| 7,402,835 B2 * | 7/2008 | Liu | ......................... | C07F 5/027 257/E21.042 |
| 2002/0130407 A1 * | 9/2002 | Dahl | ..................... | C07C 47/347 257/712 |

(Continued)

FOREIGN PATENT DOCUMENTS

| | | |
|---|---|---|
| CN | 103665025 B | 7/2016 |
| JP | 2006005090 A | 1/2006 |
| WO | 2019190495 A1 | 10/2019 |

OTHER PUBLICATIONS

"Radio frequency measurements of tunnel couplings and singlet-triplet spin states in Si:P quantum dots," House et al., Nature Communications, 6:884, DOI: 10.1038/ncomms 9848, Nov. 9, 2015, pp. 1-6.

(Continued)

*Primary Examiner* — Ida M Soward
(74) *Attorney, Agent, or Firm* — Akona IP PC

(57) ABSTRACT

Disclosed herein are diamondoid materials in quantum computing devices, as well as related methods, devices, and materials. For example, in some embodiments, a quantum computing device may include: qubit circuitry, an interconnect in conductive contact with the qubit circuitry, and a dielectric material proximate to the interconnect, wherein the dielectric material includes a diamondoid film.

20 Claims, 33 Drawing Sheets

(56) References Cited

U.S. PATENT DOCUMENTS

| | | | |
|---|---|---|---|
| 2003/0130423 | A1 | 7/2003 | Apen et al. |
| 2004/0059145 | A1* | 3/2004 | Liu ..................... C07D 221/22 562/899 |
| 2006/0040115 | A1 | 2/2006 | Watanabe et al. |
| 2008/0094722 | A1* | 4/2008 | Dahl ...................... C23C 16/27 359/642 |
| 2008/0094723 | A1* | 4/2008 | Dahl ..................... C23C 16/278 359/642 |
| 2008/0094724 | A1* | 4/2008 | Dahl ....................... G02B 1/111 359/642 |
| 2008/0096308 | A1* | 4/2008 | Santori ................. G02B 6/122 438/105 |
| 2012/0074386 | A1 | 3/2012 | Rachmady et al. |
| 2013/0264617 | A1 | 10/2013 | Joshi et al. |
| 2020/0258984 | A1 | 8/2020 | George et al. |
| 2020/0356887 | A1* | 11/2020 | Moodera ................ G06N 10/00 |

OTHER PUBLICATIONS

"Reducing intrinsic loss in superconducting resonators by surface treatment and deep etching of silicon substrates," Bruno, et al., QuTech Advanced Research Center and Kavli Institute of Nanoscience, Delft University of Technology, The Netherlands, Feb. 16, 2015, 9 pages.

"Scalable gate architecture for densely packed semiconductor spin qubits," Zajac et al., Department of Physics, Princeton University; Sandia National Laboratories, retrieved [cond-mat.mes-hall] Jul. 24, 2016, 8 pages.

"Scalable quantum circuit and control for a superconducting surface code," Versluis et al, Netherlands Organisation for Applied Scientific Research, Dec. 28, 2016, 9 pages.

"Silicon CMOS architecture for a spin-based quantum computer," Veldhorst et al., Qutech, TU Delft, The Netherlands, Centre for Quantum Computation and Communication Technology, School of Electrical Engineering and Telecommunications, The University of New South Wales, NanoElectronics Group, MESA + Institute for Nanotechnology, University of Twente, The Netherlands, Oct. 2, 2016, 13 pages.

"Single-charge tunneling in ambipolar silicon quantum dots," Müller, Filipp, Dissertation, University of Twente, Jun. 19, 2015, 148 pages.

"Single-electron Transistors fabricated with sidewall spacer patterning," Park et al., Superlattices and Microstructures 34 (2003) 231-239.

"Single-electron Transistors with wide operating temperature range," Dubuc et al., Applied Physics Letters 90, 113104 (2007) pp. 113104-1 through 113104-3.

"Single-shot read-out of an individual electron spin in a quantum dot," Elzerman et al., Nature, vol. 430, Jul. 22, 2004, pp. 431-435.

"Spin Relaxation and Decoherence of Holes in Quantum Dots," Bulaev et al., Phys. Rev. Lett. 95, 076805, Aug. 11, 2005, 1 page.

"Surface loss simulations of superconducting coplanar waveguide resonators," Wenner et al, Applied Physics Letters 99, 113513 (2011), pp. 113513-1 through 113513-3.

"Suspending superconducting qubits by silicon micromachining," Chu et al., Department of Applied Physics, Yale University, Jun. 10, 2016, 10 pages.

"Ultafast high-fidelity initialization of a quantum-dot spin qubit without magnetic fields," Mar et al., Phys. Rev. B 90 241303®, published Dec. 15, 2014, 1 page.

"Ultrafast optical control of individual quantum dot spin qubits," De Greve et al., Reports on Progress in Physics, vol. 76, No. 9, Sep. 4, 2013, 2 pages.

"Undoped accumulation-mode Si/SiGe quantum dots," Borselli et al, HRL Laboratories, LLC., Jul. 15, 2014, 4 pages.

Alcaire, Maria et al, "Plasma Enabled Conformal and Damage Free Encapsulation of Fragile Molecular Matter: from Surface-Supported to On-Device Nanostructures", Adv. Funct. Master 2019, 29, vol. 29, No. 36, Jul. 8, 2019, pp. 1-9.

"A Nanodamascene Process for Advanced Single-Electron Transistor Fabrication," Dubuc et al, IEEE Transactions on Nanotechnology, vol. 7, No. 1, Jan. 2008, pp. 68-73.

"A Reconfigurable Gate Architecture for Si/SiGe Quantum Dots," Zajac et al., Department of Physics, Princeton University; Department of Physics, University of California; Feb. 6, 2015, 5 pages.

"A two-qubit logic gate in silicon," Veldhorst et al., Nature, vol. 526, Oct. 15, 2015, pp. 410-414.

"An addressable quantum dot qubit with fault-tolerant control-fidelity," Veldhorst et al., Nature Nanotechnology vol. 9, Dec. 2014, pp. 981-985.

"Defect reduction of selective Ge epitaxy in trenches on Si(001) substrates using aspect ratio trapping," Park et al., Applied Physics Letter 90, 052113 (2007), pp. 052113-1 through 052113-3.

"Detecting bit-flip errors in a logical qubit using stabilizer measurements," Riste et al., Nature Communications, 6:6983, DOI: 10.1038/ncomms7983, Apr. 29, 2015, pp. 1-6.

"Embracing the quantum limit in silicon computing," Morton et al, Macmillan Publishers, Nov. 17, 2011, vol. 479, Nature, pp. 345-353.

"Fabrication and Characterization of Sidewall Defined Silicon-on-Insulator Single-Electron Transistor," Jung et al., IEEE Transactions on Nanotechnology, vol. 7, No. 5, Sep. 2008, pp. 544-550.

"Fast sensing of double-dot charge arrangement and spin state with an rf sensor quantum dot," Barthel et al, Materials Department, University of California, Santa Barbara, Jan. 16, 2014, 4 pages.

"Fundamentals of Silicon Material Properties for Successful Exploitation of Strain Engineering in Modern CMOS Manufacturing," Chidambaram et al, IEE Transactions on Electron Devices, vol. 53, No. 5, May 2006, pp. 944-964.

"Gate-Defined Quantum Dots in Intrinsic Silicon," Angus et al., Nano Letters 2007, vol. 7, No. 7, 2051-2055, publication date Jun. 14, 2007, retrieved from http://pubs.acs.org on Mar. 31, 2009, 6 pages.

"How it's built: Micron/Intel3D NAND Micron Opens the Veil a Little," Moyer, Bryon, retrieved from https://www.eejournal.com/article/20160201-micron/ on Nov. 29, 2017, 9 pages.

"Independent, extensible control of same-frequency superconducting qubits by selective broadcasting," Asaad et al., Netherlands Organisation for Applied Scientific Research, Aug. 28, 2015, 17 pages.

"Investigation of Vertical Type Single-Electron Transistor with Sidewall Spacer Quantum Dot," Kim et al, Student Paper, Inter-University Semiconductor Research Center and School of Electrical Engineering and Computer Science, Seoul National University, ISDRS 2011, Dec. 7-9, 2011, ISDRS 2011—http://www.ece.umd.edu/ISDR2011, 2 pages.

"Magnetic field tuning of coplanar waveguide resonators," Healey, et al., Applied Physics Letters 93, 043513 (2008), pp. 043513-1 through 043513-3 (4 pages with cover sheet).

"Multilayer microwave integrated quantum circuits for scalable quantum computing," Brecht et al, Department of Applied Physics, Yale University, Sep. 4, 2015, 5 pages.

"Photon- and phonon-assisted tunneling in the three-dimensional charge stability diagram of a triple quantum dot array," Braakman et al., Applied Physics Letters 102, 112110 (2013), pp. 112110-1 through 112110-4 (5 pages with cover sheet).

"Platinum single-electron transistors with tunnel barriers made by atomic layer deposition", George et al., Department of Electrical Engineering, University of Notre Dame, Received Jul. 7, 2010:Published Nov. 5, 2010, 3 pages.

"Quantum computation with quantum dots," Loss et al , Physical Review A, vol. 57, No. 1, Jan. 1998, pp. 120-126.

Butler, James et al., "The CVD of Nanodiamond Materials", Chemical Vapor Deposition, vol. 14, Issue 7-8, 2008, pp. 145-160.

Celii, F., et al "Diamond Chemical VAport-Deposition", Annual Review of Physical Chemistry, vol. 42, 1991, pp. 643-684.

Grill, A., "Amorphous carbon based materials as the interconnect dielectric in ULSI chips", Diamond and Related Materials 10 (2001) 234-239.

Grill, Alfred, "Diamond-like carbon: state of the art", Diamond and Related Materials 8 (1994) 428-434.

(56) References Cited

OTHER PUBLICATIONS

Li, Xiaowei et al., "Structural properties and growth evolution of diamond-like carbon films with different incident energies: A molecular dynamics study", Applied Surface Science 273 (2013) 670-675.
Roberton, J., "Diamond-like amorphous carbon", Materials Science and Engineering R 37 (2002) 129-281.
Shirafuji, Tatsuru et al., "Plasma-enhanced chemical vapor deposition of carbon films using dibromoadamantane", Thin Solid Films 518 (2009) 993-1000.
Zeze, D.A., et al "Control and Mass selection of CnH+m fragments in an inductively coupled pulsed plasma", Appl. Phys. Lett. 80, 22 (2002), https://doi.org/10.1063/1.1428776.
Zeze, D.A., et al "Targeting mass-selected cluster ions for the deposition of advanced carbonaceous materials using an inductively coupled plasma", Journal of Applied Physics 91, 1819 (2002); https://doi.org/10.1063./1.1435417.
Mistry, K. et al, "Delaying Forever: Uniaxial Strained Silicon Transistors in a 90nm CMOS Technology," Digest of Technical Papers. 2004 Symposium on VLSI Technology, 2004. (2004): 2 pages.
Morley, Gavin, "Review : Towards Spintronic Quantum Technologies with Dopants in Silicon," Electron Paramagnetic Resonance [2014], 13 pages.
Supplementary Information, retrieved from www.nature.com, doi: 10.1038/nature 15263, 8 pages (Oct. 15, 2015).

\* cited by examiner

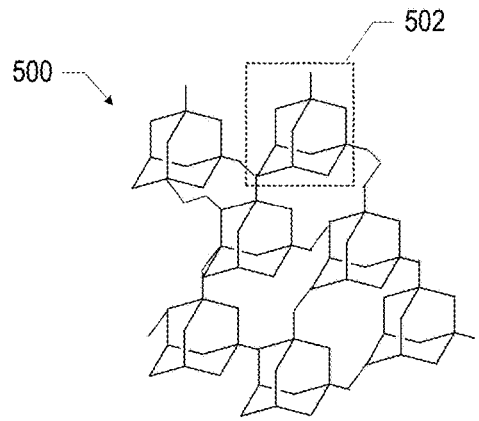 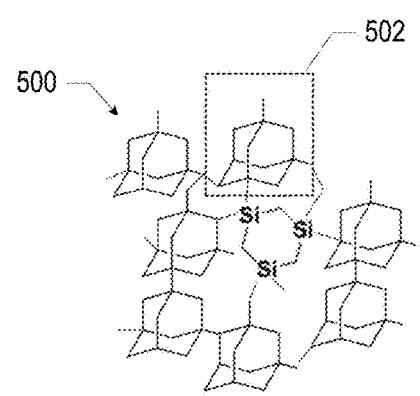
FIG. 1A    FIG. 1B
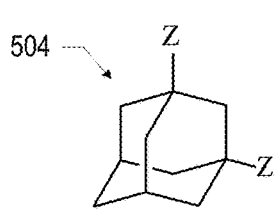 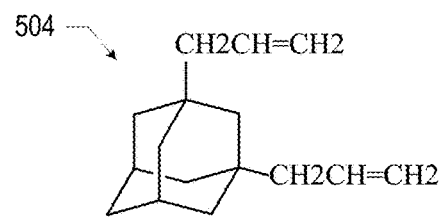
FIG. 2    FIG. 3
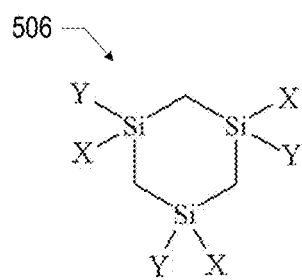 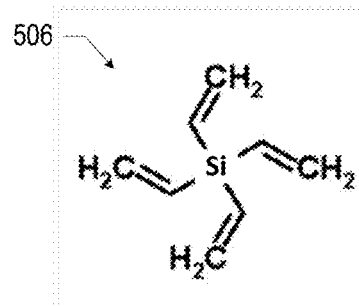 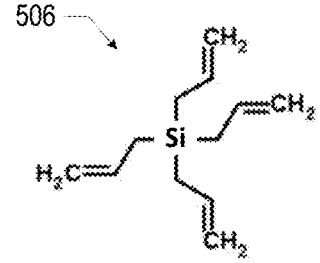
FIG. 4    FIG. 5    FIG. 6

1040

```
┌─────────────────────────────────────────────────────────────────┐
│ Apply a voltage to a first gate disposed above a quantum well stack │
│ region to cause a first quantum dot to form in a first quantum well in the │
│ quantum well stack region under the first gate, wherein the voltage is │
│ applied to the first gate through a conductive via in conductive contact │
│                     with the first gate                          │
│                             1042                                 │
└─────────────────────────────────────────────────────────────────┘
                                  │
                                  ▼
┌─────────────────────────────────────────────────────────────────┐
│ Apply a voltage to a second gate disposed above the quantum well stack │
│ region to cause a second quantum dot to form in a second quantum well │
│     in the quantum well stack region under the second gate       │
│                             1044                                 │
└─────────────────────────────────────────────────────────────────┘
                                  │
                                  ▼
┌─────────────────────────────────────────────────────────────────┐
│ Apply a voltage to a third gate disposed on the quantum well stack region │
│  to (1) cause a third quantum dot to form in a third quantum well in the │
│  quantum well stack region under the third gate or (2) provide a potential │
│     barrier between the first quantum well and the second quantum well │
│                             1046                                 │
└─────────────────────────────────────────────────────────────────┘
```

FIG. 83

DIAMONDOID MATERIALS IN QUANTUM COMPUTING DEVICES

BACKGROUND

Quantum computing refers to the field of research related to computation systems that use quantum mechanical phenomena to manipulate data. These quantum mechanical phenomena, such as superposition (in which a quantum variable can simultaneously exist in multiple different states) and entanglement (in which multiple quantum variables have related states irrespective of the distance between them in space or time), do not have analogs in the world of classical computing, and thus cannot be implemented with classical computing devices.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example, not by way of limitation, in the figures of the accompanying drawings.

FIGS. 1A and 1B illustrate example diamondoid dielectric materials (DDMs), in accordance with various embodiments.

FIGS. 2-6 illustrate example precursors for the manufacture of a DDM, in accordance with various embodiments.

FIG. 81 is a flow diagram of an illustrative method of manufacturing a quantum dot device including a DDM, in accordance with various embodiments.

FIGS. 82-83 are flow diagrams of illustrative methods of operating a quantum dot device including a DDM, in accordance with various embodiments.

DETAILED DESCRIPTION

Figure 7:
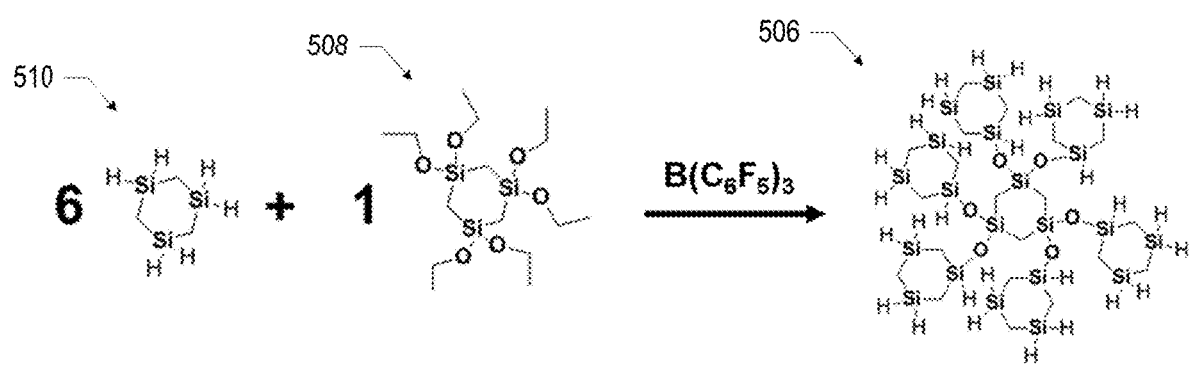
FIG. 7 illustrates a method of manufacturing an example precursor for the manufacture of a DDM, in accordance with various embodiments.

Disclosed herein are diamondoid materials in quantum computing devices, as well as related methods, devices, and materials. For example, in some embodiments, a quantum computing device may include: qubit circuitry, an interconnect in conductive contact with the qubit circuitry, and a dielectric material proximate to the interconnect, wherein the dielectric material includes a diamondoid film.

The quantum dot devices disclosed herein may enable the formation of quantum dots to serve as quantum bits ("qubits") in a quantum computing device, as well as the control of these quantum dots to perform quantum logic operations. Unlike previous approaches to quantum dot formation and manipulation, various embodiments of the quantum dot devices disclosed herein provide strong spatial localization of the quantum dots (and therefore good control over quantum dot interactions and manipulation), good scalability in the number of quantum dots included in the device, and/or design flexibility in making electrical connections to the quantum dot devices to integrate the quantum dot devices in larger computing devices.

In the following detailed description, reference is made to the accompanying drawings that form a part hereof, and in which is shown, by way of illustration, embodiments that may be practiced. It is to be understood that other embodiments may be utilized and structural or logical changes may be made without departing from the scope of the present disclosure. Therefore, the following detailed description is not to be taken in a limiting sense.

Various operations may be described as multiple discrete actions or operations in turn in a manner that is most helpful in understanding the claimed subject matter. However, the order of description should not be construed as to imply that these operations are necessarily order dependent. In particular, these operations may not be performed in the order of presentation. Operations described may be performed in a different order from the described embodiment. Various additional operations may be performed, and/or described operations may be omitted in additional embodiments.

For the purposes of the present disclosure, the phrase "A and/or B" means (A), (B), or (A and B). For the purposes of the present disclosure, the phrases "A, B, or C" and "A, B, and/or C" mean (A), (B), (C), (A and B), (A and C), (B and C), or (A, B, and C). The term "between," when used with reference to measurement ranges, is inclusive of the ends of the measurement ranges. As used herein, the notation "A/B/C" means (A), (B), and/or (C).

The description uses the phrases "in an embodiment" or "in embodiments," which may each refer to one or more of the same or different embodiments. Furthermore, the terms "comprising," "including," "having," and the like, as used with respect to embodiments of the present disclosure, are synonymous. The disclosure may use perspective-based descriptions such as "above," "below," "top," "bottom," and "side"; such descriptions are used to facilitate the discussion and are not intended to restrict the application of disclosed embodiments. The accompanying drawings are not necessarily drawn to scale. As used herein, a "high-k dielectric" refers to a material having a higher dielectric constant than silicon oxide.

FIGS. 1A and 1B illustrate diamondoid dielectric materials (DDMs) 500, in accordance with various embodiments. The DDM 500 of FIG. 1A may be a "pure diamondoid" DDM 500, while the DDM 500 of FIG. 1B may be a carbosilane DDM 500. The DDM 500 may include adamantane units 502 arranged in an amorphous manner to form a noncrystalline film, and thus the DDM 500 may have an amorphous macrostructure and a diamondoid microstructure. The amorphous macrostructure of the DDM 500 may contribute to the low loss tangent of the DDM 500 by avoiding the losses associated with grain boundaries in crystalline or polycrystalline films. The adamantane units 502 may originate from any suitable multi-functional adamantane as optimized for a given material deposition condition, such as diallyladamantane, divinyladamantane, or dibromoadamantane. The starting molecules could also originate from tri-substituted adamantane, tetra-substituted adamantane, or a combination thereof. The adamantane units 502 may also include larger-sized diamondoids, such as diadamantane, triadamantane, other larger diamondoid units, or a combination thereof. In some embodiments, as illustrated in FIG. 1B, the DDM 500 may include ringed or caged structures comprising silicon and carbon atoms; examples of carbosilane precursors 506 that may be used to manufacture a DDM 500 are discussed below with reference to FIGS. 4-7. The DDM 500 may include a number of carbon-to-carbon bonds, and the majority of the carbon-to-carbon bonds in the DDM 500 may be sp3 carbon bonds. In some embodiments, the proportion of sp3 carbon-to-carbon bonds among carbon-to-carbon bonds in the DDM 500 may be greater than 90 percent (e.g., greater than 95 percent, or greater than 99 percent). The high degree of cross-linking and the structural rigidity of the network of sp3 carbon-to-carbon bonds in the DDMs 500 disclosed herein may impart thermal stability to the DDMs 500 disclosed herein. The DDM 500 may include additional components, not shown in FIG. 1A or 1B for ease of illustration.

As discussed further below, the DDM 500 may serve as a dielectric material in quantum computing devices (e.g., including electron or nuclear spin-type quantum computing devices and/or superconducting-type quantum computing devices), having a desirably low loss tangent and being manufacturable at the low temperatures and pressures compatible with quantum device fabrication (e.g., at 450 degrees Celsius or less). Existing dielectric materials utilized in quantum computing devices typically have loss-tangents that are higher than desired (e.g., higher than 1e-3), leading to chip heating, pulse distortion, charge noise, and decoherence of the sensitive quantum state. Dielectric materials having lower loss-tangents exist, but typically require very high temperatures (e.g., greater than 600 degrees Celsius) and pressures during fabrication, and such temperatures and pressures may degrade or destroy the qubit devices. The DDMs 500 disclosed herein that predominantly include carbon and hydrogen (and, in some embodiments, silicon, as discussed below) may have low bond polarities, and therefore are not expected to undergo as much atomic reorientation under applied electric fields as conventional dielectric materials, leading to lower losses. Although some quantum computing approaches attempt to minimize the use of dielectric materials to avoid losses, the low-loss dielectric materials disclosed herein may enable the scaling of quantum computing devices to large numbers of qubit devices because large numbers of signal control lines can be effectively insulated without unacceptable losses. In some embodiments, the DDM 500 may be manufactured as a thin film having a thickness that is less than 1 micron (e.g., between 10 nanometers and 200 nanometers, or between 50 nanometers and 200 nanometers).

A DDM 500 may be manufactured in any suitable manner. For example, in some embodiments, a diamondoid precursor may be used to form a "pure diamondoid" DDM 500. FIG. 2 illustrates a diamondoid precursor 504 that may be used to manufacture a DDM 500. The diamondoid precursor 504 may be a functionalized adamantane; the units Z in the diamondoid precursor 504 may include vinyl groups (e.g., when the diamondoid precursor 504 includes divinyladamantane), methyl groups (e.g., when the diamondoid precursor 504 includes dimethyladamantane) allyl groups (e.g., when the diamondoid precursor 504 includes diallyladamantane), bromine (e.g., when the diamondoid precursor 504 includes dibromoadamantane), OH groups, or others. FIG. 3 illustrates a particular example of a diamondoid precursor 504 that includes prop-2-enyl, an allyl. FIG. 2 illustrates the particular embodiment of a di-functionalized adamantane unit, but tri-functionalized and/or tetra-functionalized adamantane units, on up to all four tertiary positions, may also be used. FIG. 2 also illustrates the particular embodiment in which both Z groups contain the same chemical identity; in other embodiments, the various Z groups may be different (e.g., when the diamondoid precursor 504 includes methyl, allyladamantane). Similarly, in some embodiments, any or all of the six secondary carbon atoms may be functionalized. In some embodiments, a diamondoid precursor 504 (e.g., any of the diamondoid precursors 504 discussed herein with reference to FIGS. 2-3) may be used as a precursor for plasma-enhanced chemical vapor deposition (PECVD) or plasma-enhanced atomic layer deposition (PEALD) of a "pure diamondoid" DDM 500. In other embodiments, multiple units of precursors can be synthesized into larger macromolecules (e.g., oligomers) to enable deposition via a spin-coating process. As such, the precursors may have different desired sizes depending upon the deposition technique.

In some embodiments, a carbosilane-based precursor may be used to form a DDM 500. FIG. 4 illustrates a carbosilane-based precursor 506 that may be used to manufacture a DDM 500. The carbosilane-based precursor 506 of FIG. 4 may be a functionalized silacyclohexane; the units X in the carbosilane-based precursor 506 may include hydrogen, and the units Y in the carbosilane-based precursor 506 may include hydrogen or a methyl group. In some embodiments, a carbosilane-based precursor 506 like that of FIG. 4 may be used as a precursor for PECVD/PEALD of a DDM 500. FIGS. 5 and 6 illustrate other carbosilane-based precursors 506, tetravinylsilane (TVS) and tetraallylsilane (TAS), respectively. In some embodiments, carbosilane-based precursors 506 like those of FIGS. 5 and 6 may be oligomerized and deposited using spin-coating to manufacture a DDM

Figure 8:
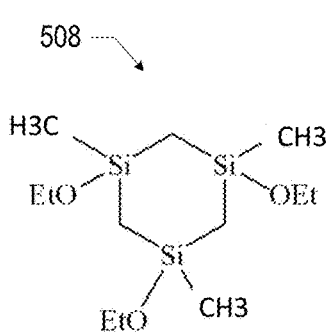
FIGS. 8-9 illustrate example inputs for the manufacture of the precursor of FIG. 7, in accordance with various embodiments.
Figure 9:
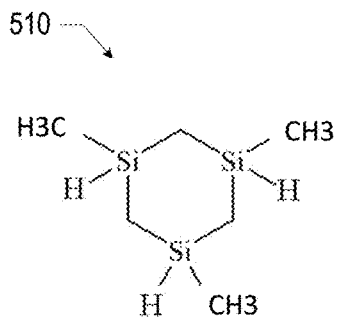

500. In some embodiments, a DDM 500 formed by spin-coating a carbosilane-based precursor 506 may achieve a loss tangent less than 6e-4 (e.g., between 2e-4 and 6e-4, or less than 2e-4). FIG. 7 illustrates a method of manufacturing an example carbosilane-based precursor 506 for the manufacture of a DDM 500, in accordance with various embodiments. In FIG. 7, a hexaethoxytrisilacyclohexane unit 508 may be reacted with 1,3,5-trisilacyclohexane units 510 to form an oligomeric mixture that is a carbosilane-based precursor 506 that may be used to form a DDM 500. In some embodiments, the hexaethoxytrisilacyclohexane unit 508 of FIG. 7 may be replaced with the triethoxy,trimethyltrisilacyclohexane unit 508 depicted in FIG. 8, and/or the 1,3,5-trisilacyclohexane unit 510 of FIG. 7 may be replaced with the trimethyltrisilacyclohexane unit 510 depicted in FIG. 9.

In some embodiments, a diamondoid precursor and a carbosilane-based precursor may be used together to form a carbosilane DDM 500. For example, a diamondoid precursor 504 (e.g., any of the diamondoid precursors 504 discussed herein) and a carbosilane-based precursor 506 (e.g., the carbosilane-based precursor 506 of FIG. 4) may be oligomerized and deposited using spin-coating to manufacture a carbosilane DDM 500. For example, some embodiments may include oligomerization of diallyladamantane with 1,3,5-trisilacyclohexane; oligomerization of diallyladamantane with trimethyl trisilacyclohexane; or oligomerization of tetravinylsilane with excess 1,3,5-trisilacyclohexane, followed by oligomerization of the resulting product with diallyladamantane; etc. Different precursor sizes and combinations might be desirable for PECVD or PEALD deposition, in which co-flow of lower molecular weight precursors may be desired (e.g.: diallyladamantane and divinylsilane, dibromoadamantane with 1,3,5-trisilacyclohexane, dimethyladamantane and trimethyltrisilacyclohexane, etc.).

Figure 84:
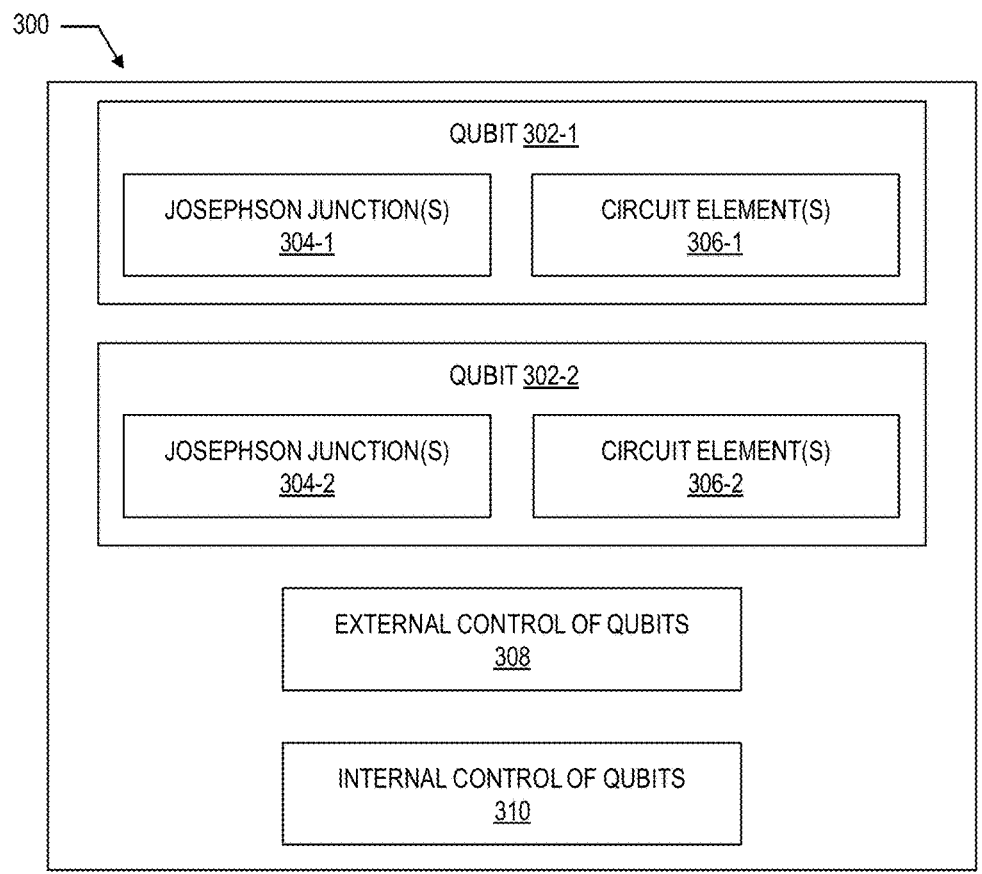
FIG. 84 is a block diagram of an example superconducting qubit-type quantum device including a DDM, in accordance with various embodiments.
Figure 85:
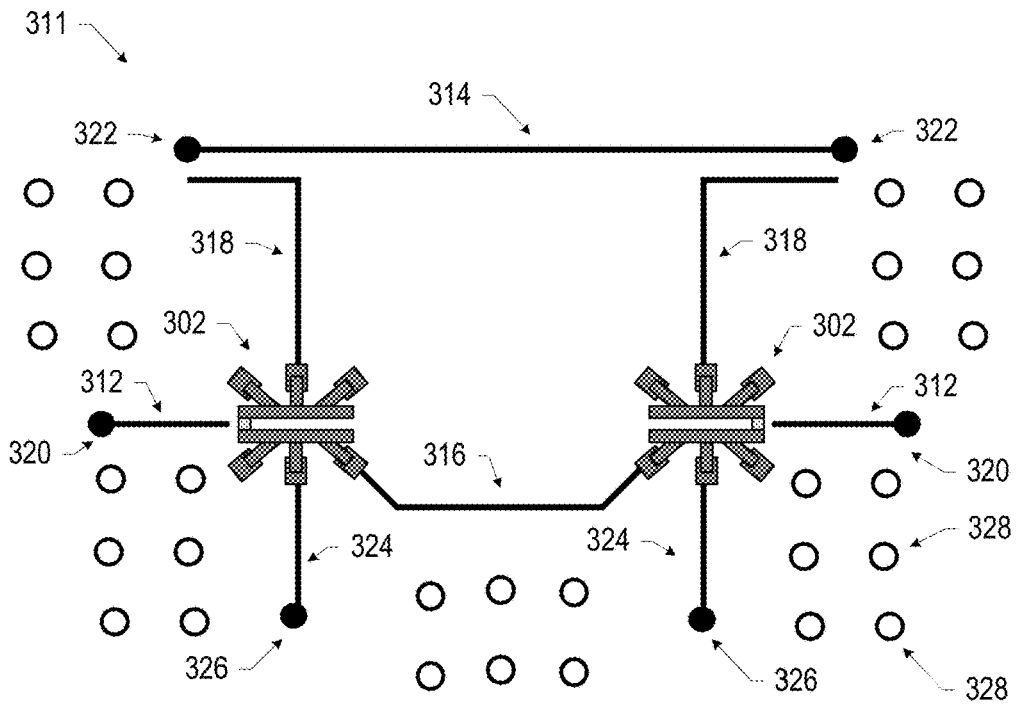
FIG. 85 illustrates an example physical layout of superconducting qubit-type quantum devices, in accordance with various embodiments.

Any of the DDMs 500 disclosed herein may be utilized as a dielectric material in any suitable quantum computing system. For example, FIGS. 10-83 illustrate example embodiments in which a DDM 500 may be included in spin qubit-type circuitry, and FIGS. 84-85 illustrate example embodiments in which a DDM 500 may be included in superconducting qubit-type circuitry.

Figure 10:
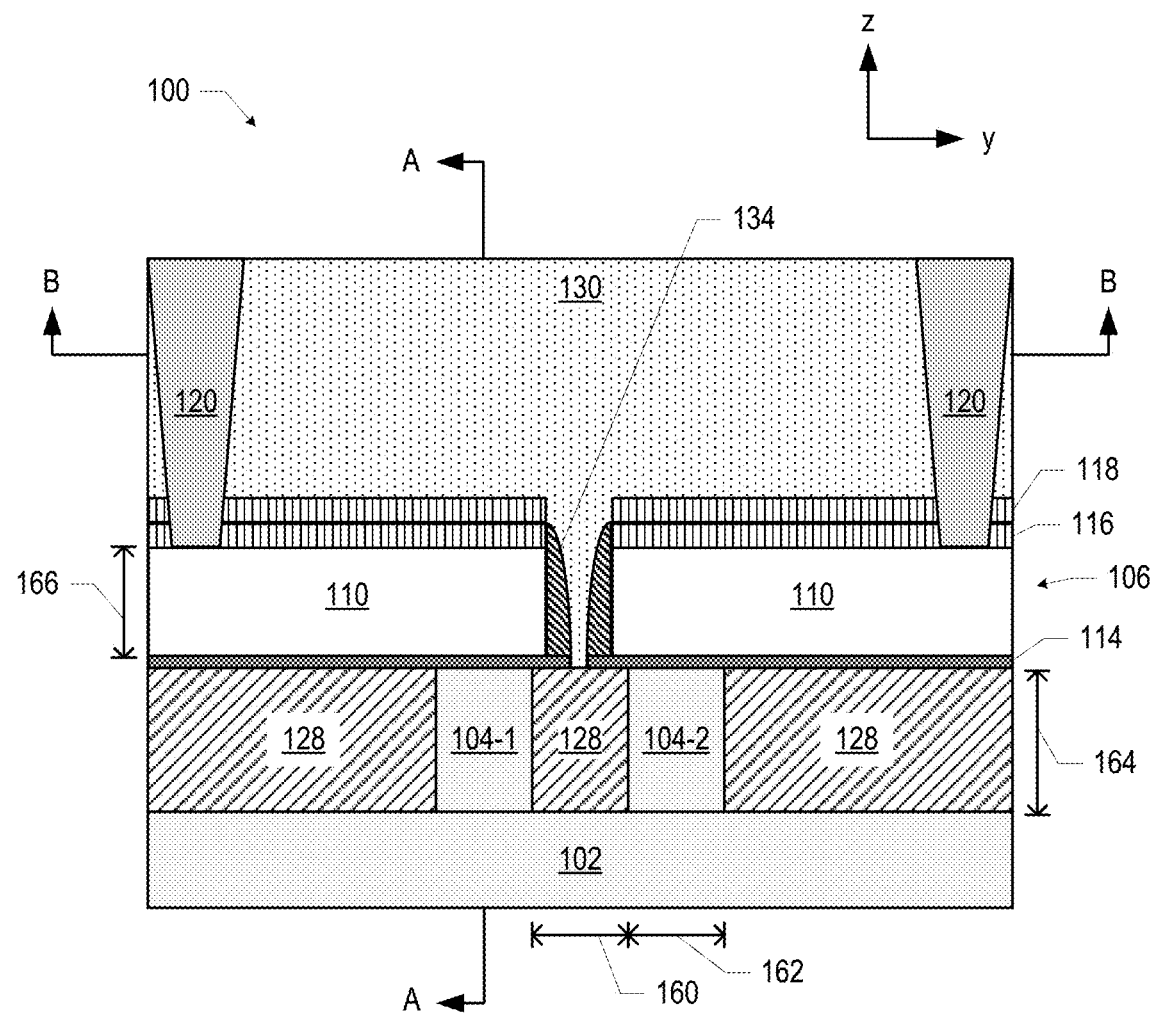
FIGS. 10-12 are cross-sectional views of a quantum dot device including a DDM, in accordance with various embodiments.
Figure 11:
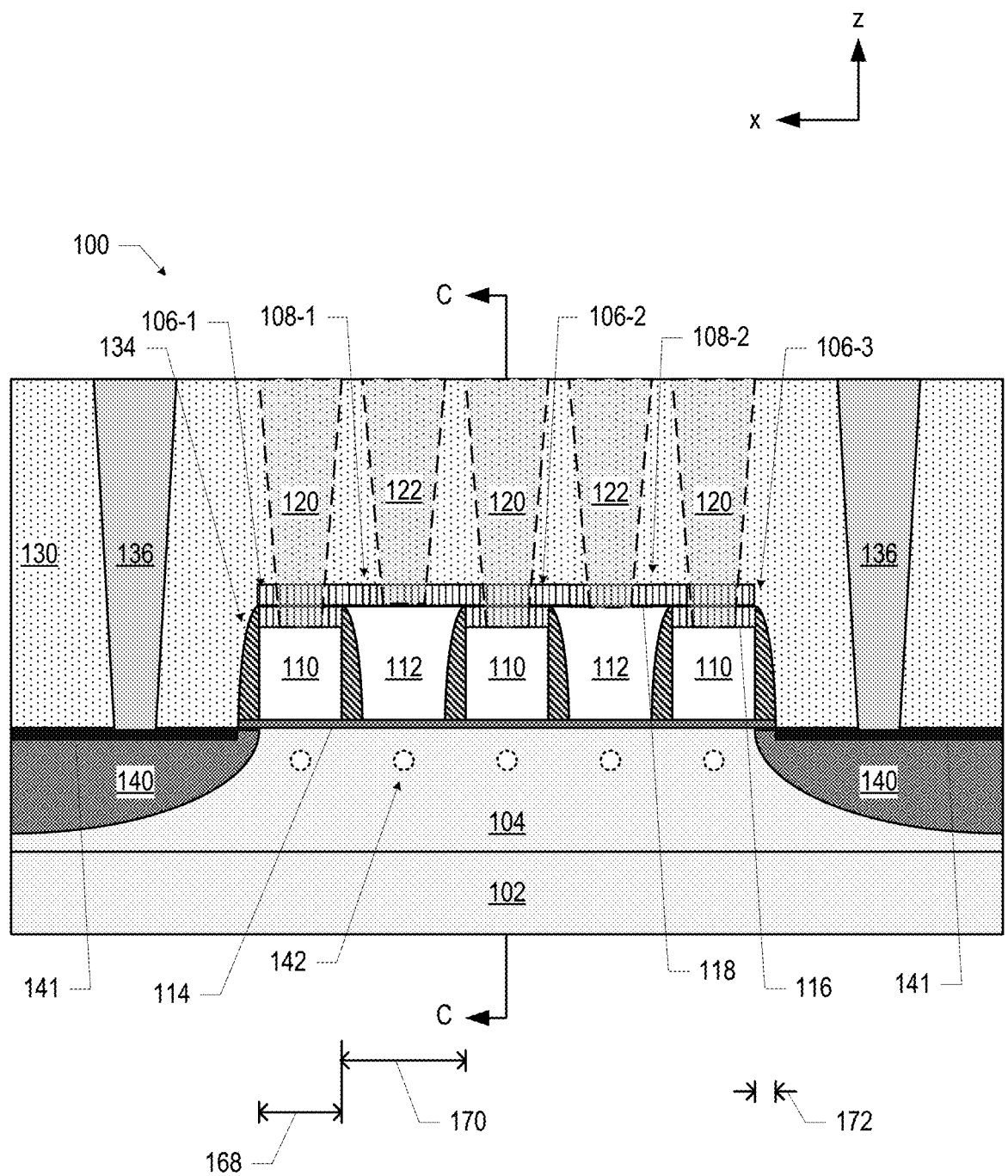
Figure 12:
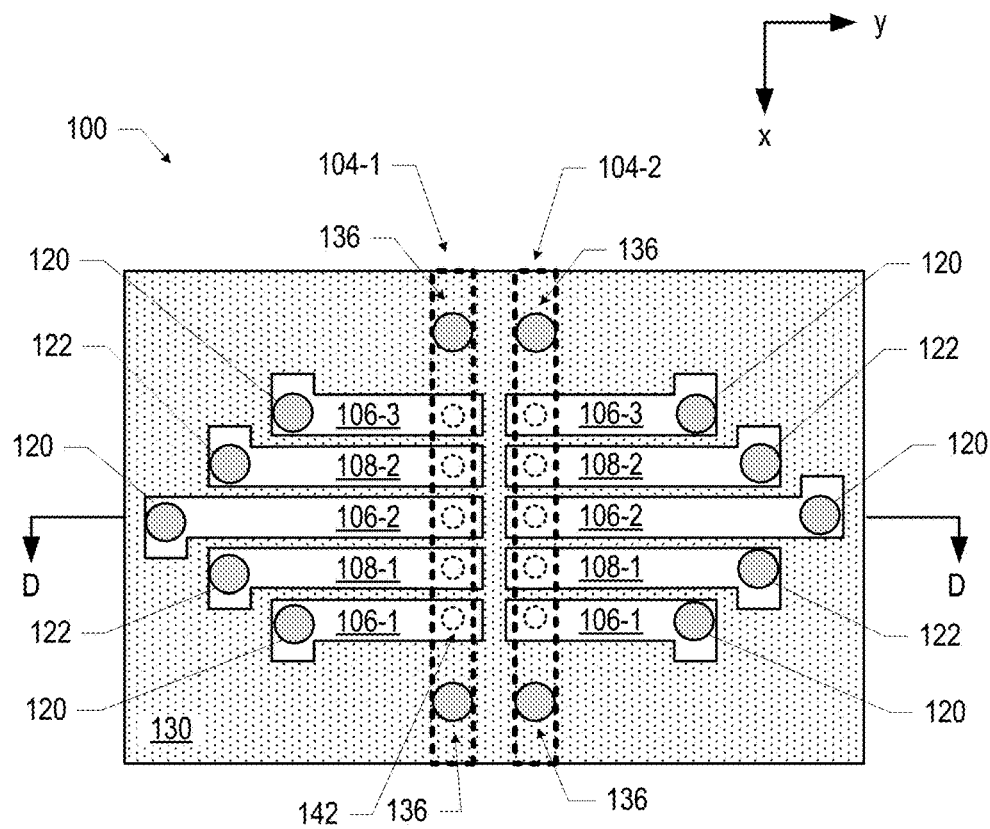

FIGS. 10-12 are cross-sectional views of a spin qubit-type quantum dot device 100, in accordance with various embodiments. In particular, FIG. 11 illustrates the quantum dot device 100 taken along the section A-A of FIG. 10 (while FIG. 10 illustrates the quantum dot device 100 taken along the section C-C of FIG. 11), and FIG. 12 illustrates the quantum dot device 100 taken along the section B-B of FIG. 10 with a number of components not shown to more readily illustrate how the gates 106/108 may be patterned (while FIG. 10 illustrates a quantum dot device 100 taken along the section D-D of FIG. 12). Although FIG. 10 indicates that the cross-section illustrated in FIG. 11 is taken through the fin 104-1, an analogous cross-section taken through the fin 104-2 may be identical, and thus the discussion of FIG. 11 refers generally to the "fin 104."

The quantum dot device 100 may include a base 102 and multiple fins 104 extending away from the base 102. The base 102 and the fins 104 may include a substrate and a quantum well stack (not shown in FIGS. 10-12, but discussed below with reference to the substrate 144 and the quantum well stack 146), distributed in any of a number of ways between the base 102 and the fins 104. The base 102 may include at least some of the substrate, and the fins 104 may each include a quantum well layer of the quantum well stack (discussed below with reference to the quantum well layer 152). Examples of base/fin arrangements are discussed below with reference to the base/fin arrangements 158 of FIGS. 38-44.

Although only two fins, 104-1 and 104-2, are shown in FIGS. 10-12, this is simply for ease of illustration, and more than two fins 104 may be included in the quantum dot device 100. In some embodiments, the total number of fins 104 included in the quantum dot device 100 is an even number, with the fins 104 organized into pairs including one active fin 104 and one read fin 104, as discussed in detail below. When the quantum dot device 100 includes more than two fins 104, the fins 104 may be arranged in pairs in a line (e.g., 2N fins total may be arranged in a 1×2N line, or a 2×N line) or in pairs in a larger array (e.g., 2N fins total may be arranged as a 4×N/2 array, a 6×N/3 array, etc.). The discussion herein will largely focus on a single pair of fins 104 for ease of illustration, but all the teachings of the present disclosure apply to quantum dot devices 100 with more fins 104.

As noted above, each of the fins 104 may include a quantum well layer (not shown in FIGS. 10-12, but discussed below with reference to the quantum well layer 152). The quantum well layer included in the fins 104 may be arranged normal to the z-direction, and may provide a layer in which a two-dimensional electron gas (2DEG) may form to enable the generation of a quantum dot during operation of the quantum dot device 100, as discussed in further detail below. The quantum well layer itself may provide a geometric constraint on the z-location of quantum dots in the fins 104, and the limited extent of the fins 104 (and therefore the quantum well layer) in the y-direction may provide a geometric constraint on the y-location of quantum dots in the fins 104. To control the x-location of quantum dots in the fins 104, voltages may be applied to gates disposed on the fins 104 to adjust the energy profile along the fins 104 in the x-direction and thereby constrain the x-location of quantum dots within quantum wells (discussed in detail below with reference to the gates 106/108). The dimensions of the fins 104 may take any suitable values. For example, in some embodiments, the fins 104 may each have a width 162 between 10 and 30 nanometers. In some embodiments, the fins 104 may each have a height 164 between 200 nanometers and 400 nanometers (e.g., between 250 nanometers and 350 nanometers, or equal to 300 nanometers).

The fins 104 may be arranged in parallel, as illustrated in FIGS. 10 and 12, and may be spaced apart by an insulating material 128, which may be disposed on opposite faces of the fins 104. The insulating material 128 may be a dielectric material, such as silicon oxide or any of the DDMs 500 disclosed herein. For example, in some embodiments, the fins 104 may be spaced apart by a distance 160 between 100 microns and 250 microns.

Multiple gates may be disposed on each of the fins 104. In the embodiment illustrated in FIG. 11, three gates 106 and two gates 108 are shown as distributed on the top of the fin 104. This particular number of gates is simply illustrative, and any suitable number of gates may be used. Additionally, as discussed below with reference to FIG. 48, multiple groups of gates (like the gates illustrated in FIG. 11) may be disposed on the fin 104.

As shown in FIG. 11, the gate 108-1 may be disposed between the gates 106-1 and 106-2, and the gate 108-2 may be disposed between the gates 106-2 and 106-3. Each of the gates 106/108 may include a gate dielectric 114; in the embodiment illustrated in FIG. 11, the gate dielectric 114 for all of the gates 106/108 is provided by a common layer of gate dielectric material. In other embodiments, the gate dielectric 114 for each of the gates 106/108 may be provided by separate portions of gate dielectric 114 (e.g., as discussed below with reference to FIGS. 49-53). In some embodiments, the gate dielectric 114 may be a multilayer gate dielectric (e.g., with multiple materials used to improve the interface between the fin 104 and the corresponding gate metal). The gate dielectric 114 may be, for example, silicon oxide, aluminum oxide, or a high-k dielectric, such as hafnium oxide. More generally, the gate dielectric 114 may include elements such as hafnium, silicon, oxygen, titanium, tantalum, lanthanum, aluminum, zirconium, barium, strontium, yttrium, lead, scandium, niobium, and zinc. Examples of materials that may be used in the gate dielectric 114 may include, but are not limited to, hafnium oxide, hafnium silicon oxide, lanthanum oxide, lanthanum aluminum oxide, zirconium oxide, zirconium silicon oxide, tantalum oxide, titanium oxide, barium strontium titanium oxide, barium titanium oxide, strontium titanium oxide, yttrium oxide, aluminum oxide, tantalum oxide, tantalum silicon oxide, lead scandium tantalum oxide, and lead zinc niobate. In some embodiments, an annealing process may be carried out on the gate dielectric 114 to improve the quality of the gate dielectric 114.

Each of the gates 106 may include a gate metal 110 and a hardmask 116. The hardmask 116 may be formed of silicon nitride, silicon carbide, or another suitable material. The gate metal 110 may be disposed between the hardmask 116 and the gate dielectric 114, and the gate dielectric 114 may be disposed between the gate metal 110 and the fin 104. Only one portion of the hardmask 116 is labeled in FIG. 11 for ease of illustration. In some embodiments, the gate metal 110 may be a superconductor, such as aluminum, titanium nitride (e.g., deposited via atomic layer deposition), or niobium titanium nitride. In some embodiments, the hardmask 116 may not be present in the quantum dot device 100 (e.g., a hardmask like the hardmask 116 may be removed during processing, as discussed below). The sides of the gate metal 110 may be substantially parallel, as shown in FIG. 11, and insulating spacers 134 may be disposed on the sides of the gate metal 110 and the hardmask 116. As illustrated in FIG. 11, the spacers 134 may be thicker closer to the fin 104 and thinner farther away from the fin 104. In some embodiments, the spacers 134 may have a convex shape. The spacers 134 may be formed of any suitable material, such as a carbon-doped oxide, silicon nitride, silicon oxide, or other carbides or nitrides (e.g., silicon carbide, silicon nitride doped with carbon, and silicon oxynitride). The gate metal 110 may be any suitable metal, such as titanium nitride.

Each of the gates 108 may include a gate metal 112 and a hardmask 118. The hardmask 118 may be formed of silicon nitride, silicon carbide, or another suitable material. The gate metal 112 may be disposed between the hardmask 118 and the gate dielectric 114, and the gate dielectric 114 may be disposed between the gate metal 112 and the fin 104. In the embodiment illustrated in FIG. 11, the hardmask 118 may extend over the hardmask 116 (and over the gate metal 110 of the gates 106), while in other embodiments, the hardmask 118 may not extend over the gate metal 110 (e.g., as discussed below with reference to FIG. 54). In some embodiments, the gate metal 112 may be a different metal from the gate metal 110; in other embodiments, the gate metal 112 and the gate metal 110 may have the same material composition. In some embodiments, the gate metal 112 may be a superconductor, such as aluminum, titanium nitride (e.g., deposited via atomic layer deposition), or niobium titanium nitride. In some embodiments, the hardmask 118 may not be present in the quantum dot device 100 (e.g., a hardmask like the hardmask 118 may be removed during processing, as discussed below).

The gate 108-1 may extend between the proximate spacers 134 on the sides of the gate 106-1 and the gate 106-2, as shown in FIG. 11. In some embodiments, the gate metal 112 of the gate 108-1 may extend between the spacers 134 on the sides of the gate 106-1 and the gate 106-2. Thus, the gate metal 112 of the gate 108-1 may have a shape that is substantially complementary to the shape of the spacers 134, as shown. Similarly, the gate 108-2 may extend between the proximate spacers 134 on the sides of the gate 106-2 and the gate 106-3. In some embodiments in which the gate dielectric 114 is not a layer shared commonly between the gates 108 and 106, but instead is separately deposited on the fin 104 between the spacers 134 (e.g., as discussed below with reference to FIGS. 49-53), the gate dielectric 114 may extend at least partially up the sides of the spacers 134, and the gate metal 112 may extend between the portions of gate dielectric 114 on the spacers 134. The gate metal 112, like the gate metal 110, may be any suitable metal, such as titanium nitride.

The dimensions of the gates 106/108 may take any suitable values. For example, in some embodiments, the z-height 166 of the gate metal 110 may be between 40 nanometers and 75 nanometers (e.g., approximately 50 nanometers); the z-height of the gate metal 112 may be in the same range. In embodiments like the ones illustrated in FIGS. 11, 47, and 54, the z-height of the gate metal 112 may be greater than the z-height of the gate metal 110. In some embodiments, the length 168 of the gate metal 110 (i.e., in the x-direction) may be between 20 nanometers and 40 nanometers (e.g., 30 nanometers). In some embodiments, the distance 170 between adjacent ones of the gates 106 (e.g., as measured from the gate metal 110 of one gate 106 to the gate metal 110 of an adjacent gate 106 in the x-direction, as illustrated in FIG. 11) may be between 40 nanometers and 60 nanometers (e.g., 50 nanometers). In some embodiments, the thickness 172 of the spacers 134 may be between 1 nanometer and 10 nanometers (e.g., between 3 nanometers and 5 nanometers, between 4 nanometers and 6 nanometers, or between 4 nanometers and 7 nanometers). The length of the gate metal 112 (i.e., in the x-direction) may depend on the dimensions of the gates 106 and the spacers 134, as illustrated in FIG. 11. As indicated in FIG. 10, the gates 106/108 on one fin 104 may extend over the insulating material 128 beyond their respective fins 104 and toward the other fin 104, but may be isolated from their counterpart gates by the intervening insulating material 130 and spacers 134.

As shown in FIG. 11, the gates 106 and 108 may be alternatingly arranged along the fin 104 in the x-direction. During operation of the quantum dot device 100, voltages may be applied to the gates 106/108 to adjust the potential energy in the quantum well layer (not shown) in the fin 104 to create quantum wells of varying depths in which quantum dots 142 may form. Only one quantum dot 142 is labeled with a reference numeral in FIGS. 11 and 12 for ease of illustration, but five are indicated as dotted circles in each fin 104. The location of the quantum dots 142 in FIG. 11 is not intended to indicate a particular geometric positioning of the quantum dots 142. The spacers 134 may themselves provide "passive" barriers between quantum wells under the gates 106/108 in the quantum well layer, and the voltages applied to different ones of the gates 106/108 may adjust the potential energy under the gates 106/108 in the quantum well layer; decreasing the potential energy may form quantum wells, while increasing the potential energy may form quantum barriers.

The fins 104 may include doped regions 140 that may serve as a reservoir of charge carriers for the quantum dot device 100. For example, an n-type doped region 140 may supply electrons for electron-type quantum dots 142, and a p-type doped region 140 may supply holes for hole-type quantum dots 142. In some embodiments, an interface material 141 may be disposed at a surface of a doped region 140, as shown. The interface material 141 may facilitate electrical coupling between a conductive contact (e.g., a conductive via 136, as discussed below) and the doped region 140. The interface material 141 may be any suitable metal-semiconductor ohmic contact material; for example, in embodiments in which the doped region 140 includes silicon, the interface material 141 may include nickel silicide, aluminum silicide, titanium silicide, molybdenum silicide, cobalt silicide, tungsten silicide, or platinum silicide (e.g., as discussed below with reference to FIGS. 31-32). In some embodiments, the interface material 141 may be a non-silicide compound, such as titanium nitride. In some embodiments, the interface material 141 may be a metal (e.g., aluminum, tungsten, or indium).

The quantum dot devices 100 disclosed herein may be used to form electron-type or hole-type quantum dots 142. Note that the polarity of the voltages applied to the gates 106/108 to form quantum wells/barriers depend on the charge carriers used in the quantum dot device 100. In embodiments in which the charge carriers are electrons (and thus the quantum dots 142 are electron-type quantum dots), amply negative voltages applied to a gate 106/108 may increase the potential barrier under the gate 106/108, and amply positive voltages applied to a gate 106/108 may decrease the potential barrier under the gate 106/108 (thereby forming a potential well in which an electron-type quantum dot 142 may form). In embodiments in which the charge carriers are holes (and thus the quantum dots 142 are hole-type quantum dots), amply positive voltages applied to a gate 106/108 may increase the potential barrier under the gate 106/108, and amply negative voltages applied to a gate 106 and 108 may decrease the potential barrier under the gate 106/108 (thereby forming a potential well in which a hole-type quantum dot 142 may form). The quantum dot devices 100 disclosed herein may be used to form electron-type or hole-type quantum dots.

Voltages may be applied to each of the gates 106 and 108 separately to adjust the potential energy in the quantum well layer under the gates 106 and 108, and thereby control the formation of quantum dots 142 under each of the gates 106 and 108. Additionally, the relative potential energy profiles under different ones of the gates 106 and 108 allow the quantum dot device 100 to tune the potential interaction between quantum dots 142 under adjacent gates. For example, if two adjacent quantum dots 142 (e.g., one quantum dot 142 under a gate 106 and another quantum dot 142 under a gate 108) are separated by only a short potential barrier, the two quantum dots 142 may interact more strongly than if they were separated by a taller potential barrier. Since the depth of the potential wells/height of the potential barriers under each gate 106/108 may be adjusted by adjusting the voltages on the respective gates 106/108, the differences in potential between adjacent gates 106/108 may be adjusted, and thus the interaction tuned.

In some applications, the gates 108 may be used as plunger gates to enable the formation of quantum dots 142 under the gates 108, while the gates 106 may be used as barrier gates to adjust the potential barrier between quantum dots 142 formed under adjacent gates 108. In other applications, the gates 108 may be used as barrier gates, while the gates 106 are used as plunger gates. In other applications, quantum dots 142 may be formed under all of the gates 106 and 108, or under any desired subset of the gates 106 and 108.

Conductive vias and lines may make contact with the gates 106/108, and to the doped regions 140, to enable electrical connection to the gates 106/108 and the doped regions 140 to be made in desired locations. As shown in FIGS. 10-12, the gates 106 may extend away from the fins 104, and conductive vias 120 may contact the gates 106 (and are drawn in dashed lines in FIG. 11 to indicate their location behind the plane of the drawing). The conductive vias 120 may extend through the hardmask 116 and the hardmask 118 to contact the gate metal 110 of the gates 106. The gates 108 may extend away from the fins 104, and conductive vias 122 may contact the gates 108 (also drawn in dashed lines in FIG. 11 to indicate their location behind the plane of the drawing). The conductive vias 122 may extend through the hardmask 118 to contact the gate metal 112 of the gates 108. Conductive vias 136 may contact the interface material 141 and may thereby make electrical contact with the doped regions 140. The quantum dot device 100 may include further conductive vias and/or lines (not shown) to make electrical contact to the gates 106/108 and/or the doped regions 140, as desired. Example techniques for forming conductive vias 120/122/136 (as well as conductive lines and further interconnect structures to contact the conductive vias 120/122/136) are discussed below with reference to FIGS. 57-80. The conductive vias and lines included in a quantum dot device 100 may include any suitable materials, such as copper, tungsten (deposited, e.g., by chemical vapor deposition (CVD)), or a superconductor (e.g., aluminum, tin, titanium nitride, niobium titanium nitride, tantalum, niobium, or other niobium compounds such as niobium tin and niobium germanium).

During operation, a bias voltage may be applied to the doped regions 140 (e.g., via the conductive vias 136 and the interface material 141) to cause current to flow through the doped regions 140. When the doped regions 140 are doped with an n-type material, this voltage may be positive; when the doped regions 140 are doped with a p-type material, this voltage may be negative. The magnitude of this bias voltage may take any suitable value (e.g., between 0.25 volts and 2 volts).

The conductive vias 120, 122, and 136 may be electrically isolated from each other by an insulating material 130. The insulating material 130 may be any suitable material, such as an interlayer dielectric (ILD). The insulating material 130 may include any of the DDMs 500 disclosed herein. In other embodiments, the insulating material 130 may include silicon oxide, silicon nitride, aluminum oxide, carbon-doped oxide, and/or silicon oxynitride. As known in the art of integrated circuit manufacturing, conductive vias and lines may be formed in an iterative process in which layers of structures are formed on top of each other. In some embodiments, the conductive vias 120/122/136 may have a width that is 20 nanometers or greater at their widest point (e.g., 30 nanometers), and a pitch of 80 nanometers or greater (e.g., 100 nanometers). In some embodiments, conductive lines (not shown) included in the quantum dot device 100 may have a width that is 100 nanometers or greater, and a pitch of 100 nanometers or greater. The particular arrangement of conductive vias shown in FIGS. 10-12 is simply illustrative, and any electrical routing arrangement may be implemented.

As discussed above, the structure of the fin 104-1 may be the same as the structure of the fin 104-2; similarly, the construction of gates 106/108 on the fin 104-1 may be the same as the construction of gates 106/108 on the fin 104-2. The gates 106/108 on the fin 104-1 may be mirrored by corresponding gates 106/108 on the parallel fin 104-2, and the insulating material 130 may separate the gates 106/108 on the different fins 104-1 and 104-2. In particular, quantum dots 142 formed in the fin 104-1 (under the gates 106/108) may have counterpart quantum dots 142 in the fin 104-2 (under the corresponding gates 106/108). In some embodiments, the quantum dots 142 in the fin 104-1 may be used as "active" quantum dots in the sense that these quantum dots 142 act as qubits and are controlled (e.g., by voltages applied to the gates 106/108 of the fin 104-1) to perform quantum computations. The quantum dots 142 in the fin 104-2 may be used as "read" quantum dots in the sense that these quantum dots 142 may sense the quantum state of the quantum dots 142 in the fin 104-1 by detecting the electric field generated by the charge in the quantum dots 142 in the fin 104-1, and may convert the quantum state of the quantum dots 142 in the fin 104-1 into electrical signals that may be detected by the gates 106/108 on the fin 104-2. Each quantum dot 142 in the fin 104-1 may be read by its corresponding quantum dot 142 in the fin 104-2. Thus, the quantum dot device 100 enables both quantum computation and the ability to read the results of a quantum computation.

The quantum dot devices 100 disclosed herein may be manufactured using any suitable techniques. FIGS. 13-34 illustrate various example stages in the manufacture of the quantum dot device 100 of FIGS. 10-12, in accordance with various embodiments. Although the particular manufacturing operations discussed below with reference to FIGS. 13-34 are illustrated as manufacturing a particular embodiment of the quantum dot device 100, these operations may be applied to manufacture many different embodiments of the quantum dot device 100, as discussed herein. Any of the elements discussed below with reference to FIGS. 13-34 may take the form of any of the embodiments of those elements discussed above (or otherwise disclosed herein).

Figure 13:
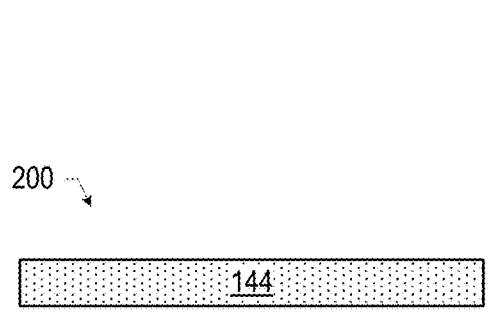
FIGS. 13-34 illustrate various example stages in the manufacture of a quantum dot device including a DDM, in accordance with various embodiments.

FIG. 13 illustrates a cross-sectional view of an assembly 200 including a substrate 144. The substrate 144 may include any suitable semiconductor material or materials. In some embodiments, the substrate 144 may include a semiconductor material. For example, the substrate 144 may include silicon (e.g., may be formed from a silicon wafer).

Figure 14:
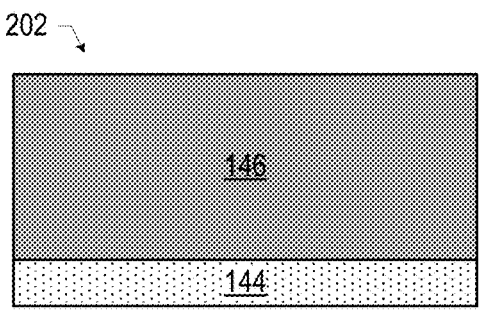

FIG. 14 illustrates a cross-sectional view of an assembly 202 subsequent to providing a quantum well stack 146 on the substrate 144 of the assembly 200 (FIG. 13). The quantum well stack 146 may include a quantum well layer (not shown) in which a 2DEG may form during operation of the quantum dot device 100. Various embodiments of the quantum well stack 146 are discussed below with reference to FIGS. 35-37.

Figure 15:
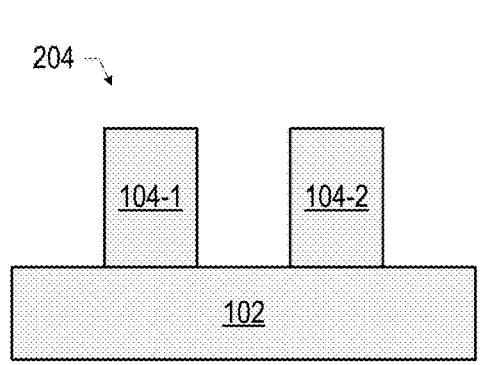

FIG. 15 illustrates a cross-sectional view of an assembly 204 subsequent to forming fins 104 in the assembly 202 (FIG. 14). The fins 104 may extend from a base 102, and may be formed in the assembly 202 by patterning and then etching the assembly 202, as known in the art. For example, a combination of dry and wet etch chemistry may be used to form the fins 104, and the appropriate chemistry may depend on the materials included in the assembly 202, as known in the art. At least some of the substrate 144 may be included in the base 102, and at least some of the quantum well stack 146 may be included in the fins 104. In particular, the quantum well layer (not shown) of the quantum well stack 146 may be included in the fins 104. Example arrangements in which the quantum well stack 146 and the substrate 144 are differently included in the base 102 and the fins 104 are discussed below with reference to FIGS. 38-44.

Figure 16:
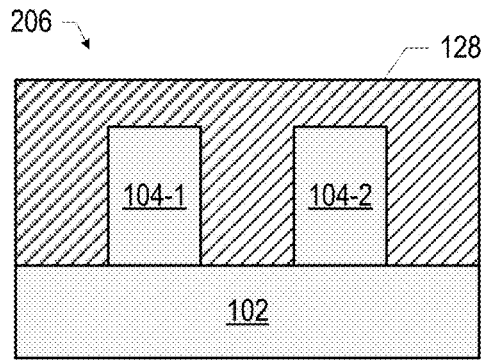

FIG. 16 illustrates a cross-sectional view of an assembly 206 subsequent to providing an insulating material 128 to the assembly 204 (FIG. 15). Any suitable material may be used as the insulating material 128 to electrically insulate the fins 104 from each other. As noted above, in some embodiments, the insulating material 128 may be a dielectric material, such as any of the DDMs 500 disclosed herein or silicon oxide.

Figure 17:
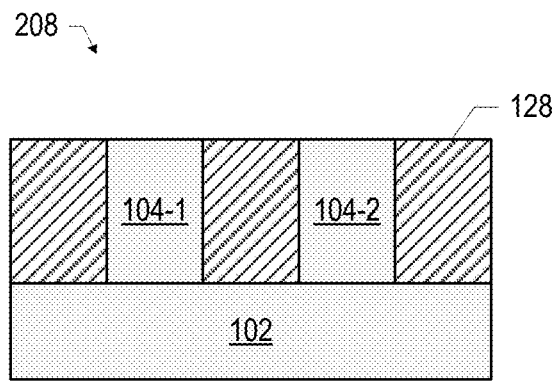

FIG. 17 illustrates a cross-sectional view of an assembly 208 subsequent to planarizing the assembly 206 (FIG. 16) to remove the insulating material 128 above the fins 104. In some embodiments, the assembly 206 may be planarized using a chemical mechanical polishing (CMP) technique.

Figure 18:
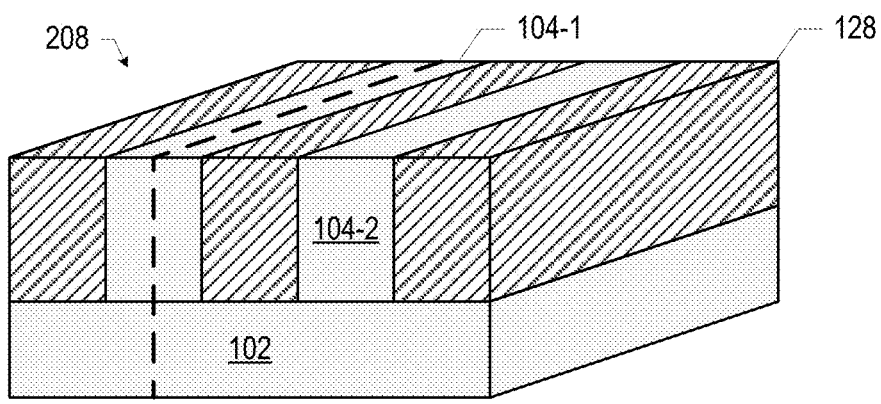
Figure 19:
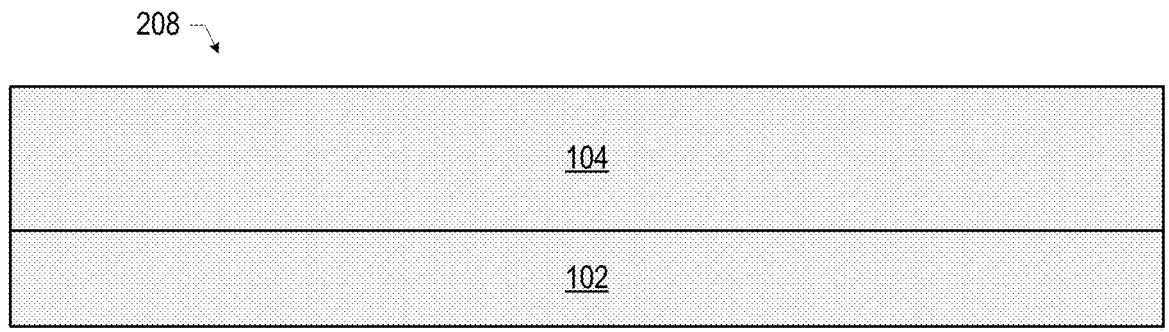

FIG. 18 is a perspective view of at least a portion of the assembly 208, showing the fins 104 extending from the base 102 and separated by the insulating material 128. The cross-sectional views of FIGS. 13-17 are taken parallel to the plane of the page of the perspective view of FIG. 18. FIG. 19 is another cross-sectional view of the assembly 208, taken along the dashed line along the fin 104-1 in FIG. 18. The cross-sectional views illustrated in FIGS. 20-34 are taken along the same cross-section as FIG. 19.

Figure 20:
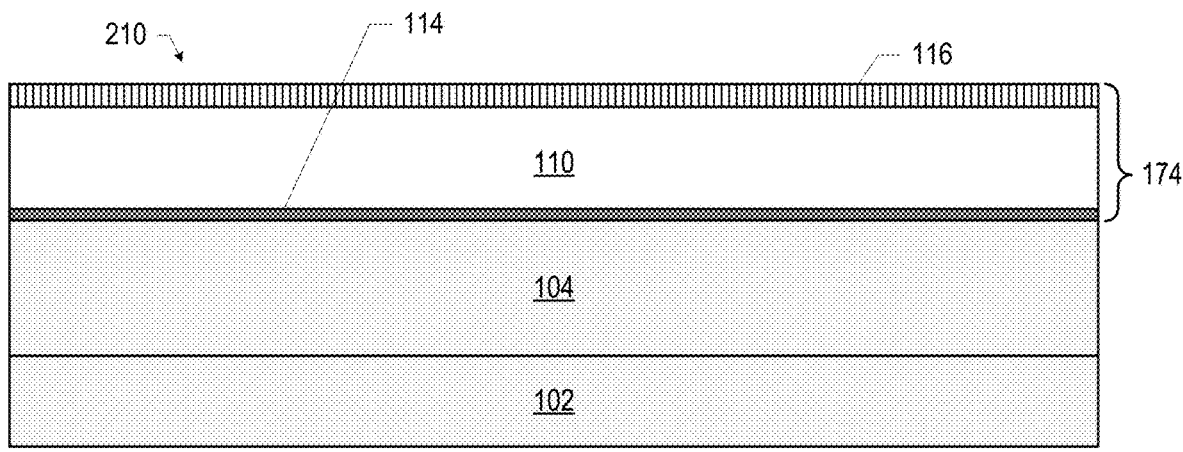

FIG. 20 is a cross-sectional view of an assembly 210 subsequent to forming a gate stack 174 on the fins 104 of the assembly 208 (FIGS. 17-19). The gate stack 174 may include the gate dielectric 114, the gate metal 110, and a hardmask 116. The hardmask 116 may be formed of an electrically insulating material, such as silicon nitride or carbon-doped nitride. In some embodiments, the hardmask 116 (or any of the hardmasks disclosed herein) may include a DDM 500.

Figure 21:
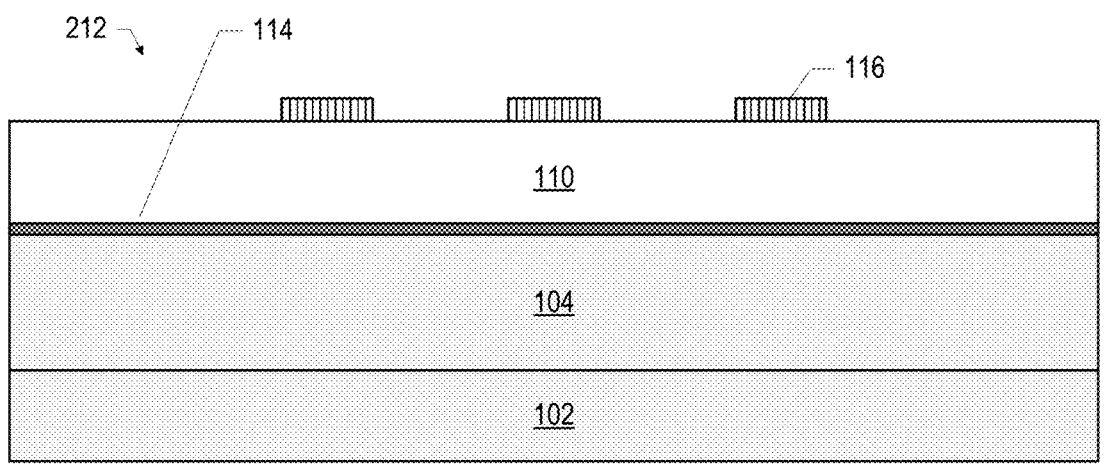

FIG. 21 is a cross-sectional view of an assembly 212 subsequent to patterning the hardmask 116 of the assembly 210 (FIG. 20). The pattern applied to the hardmask 116 may correspond to the locations for the gates 106, as discussed below. The hardmask 116 may be patterned by applying a resist, patterning the resist using lithography, and then etching the hardmask (using dry etching or any appropriate technique).

Figure 22:
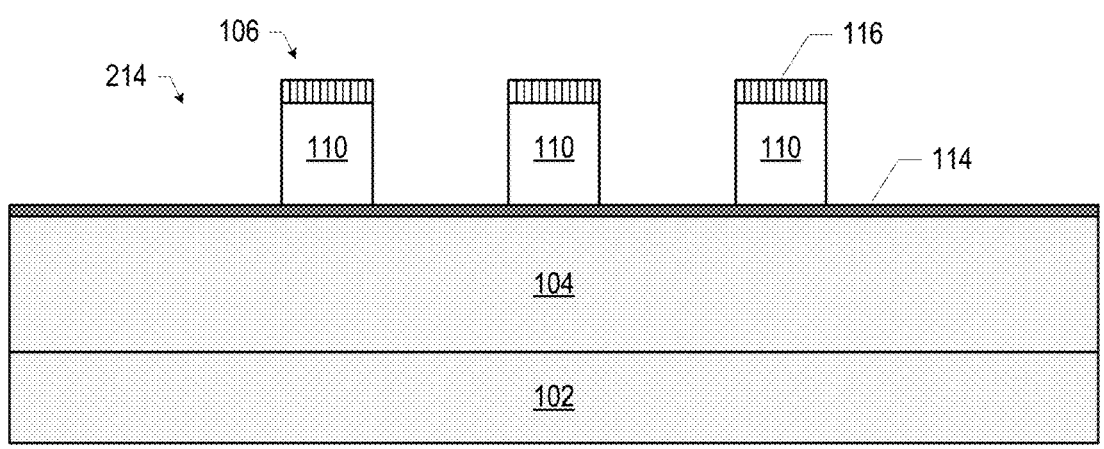

FIG. 22 is a cross-sectional view of an assembly 214 subsequent to etching the assembly 212 (FIG. 21) to remove the gate metal 110 that is not protected by the patterned hardmask 116 to form the gates 106. In some embodiments, as illustrated in FIG. 22, the gate dielectric 114 may remain after the etched gate metal 110 is etched away; in other embodiments, the gate dielectric 114 may also be etched during the etching of the gate metal 110. Examples of such embodiments are discussed below with reference to FIGS. 49-53.

Figure 23:
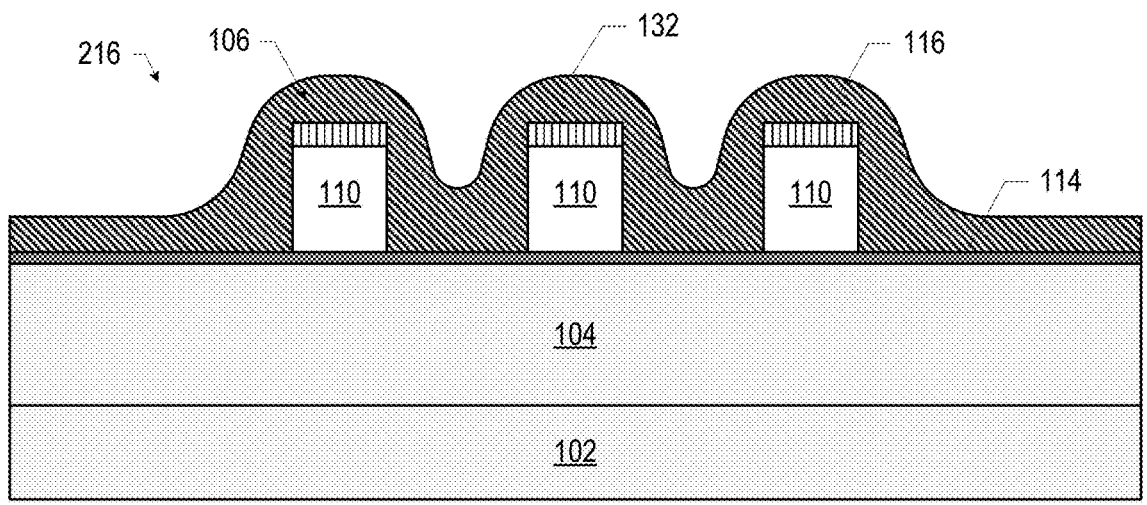

FIG. 23 is a cross-sectional view of an assembly 216 subsequent to providing spacer material 132 on the assembly 214 (FIG. 22). The spacer material 132 may include any of the materials discussed above with reference to the spacers 134, for example, and may be deposited using any suitable technique. For example, the spacer material 132 may be a nitride material (e.g., silicon nitride) deposited by sputtering.

Figure 24:
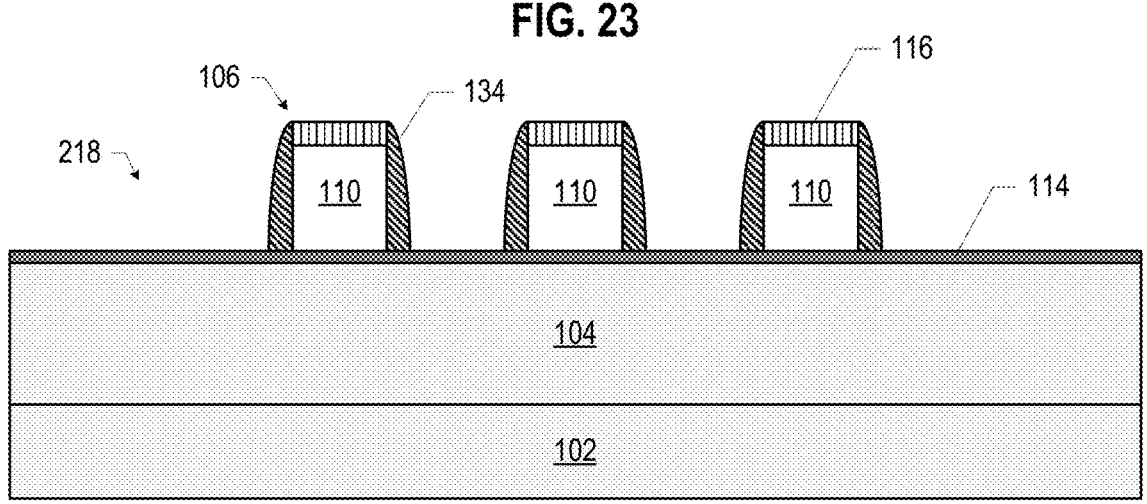

FIG. 24 is a cross-sectional view of an assembly 218 subsequent to etching the spacer material 132 of the assembly 216 (FIG. 23), leaving spacers 134 formed of the spacer material 132 on the sides of the gates 106 (e.g., on the sides of the hardmask 116 and the gate metal 110). The etching of the spacer material 132 may be an anisotropic etch, etching the spacer material 132 "downward" to remove the spacer material 132 on top of the gates 106 and in some of the area between the gates 106, while leaving the spacers 134 on the sides of the gates 106. In some embodiments, the anisotropic etch may be a dry etch.

Figure 25:
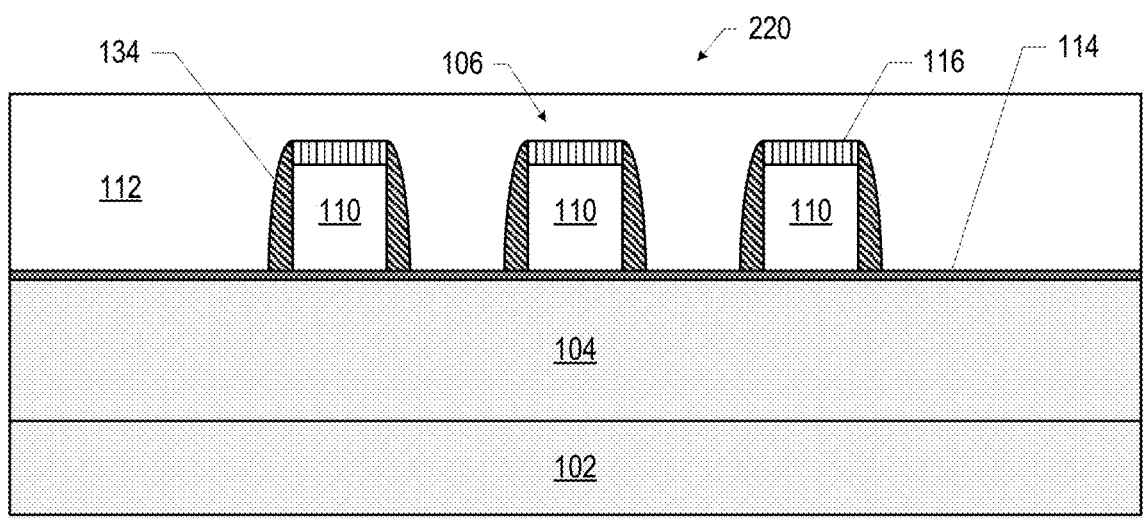

FIG. 25 is a cross-sectional view of an assembly 220 subsequent to providing the gate metal 112 on the assembly 218 (FIG. 24). The gate metal 112 may fill the areas between adjacent ones of the gates 106, and may extend over the tops of the gates 106.

Figure 26:
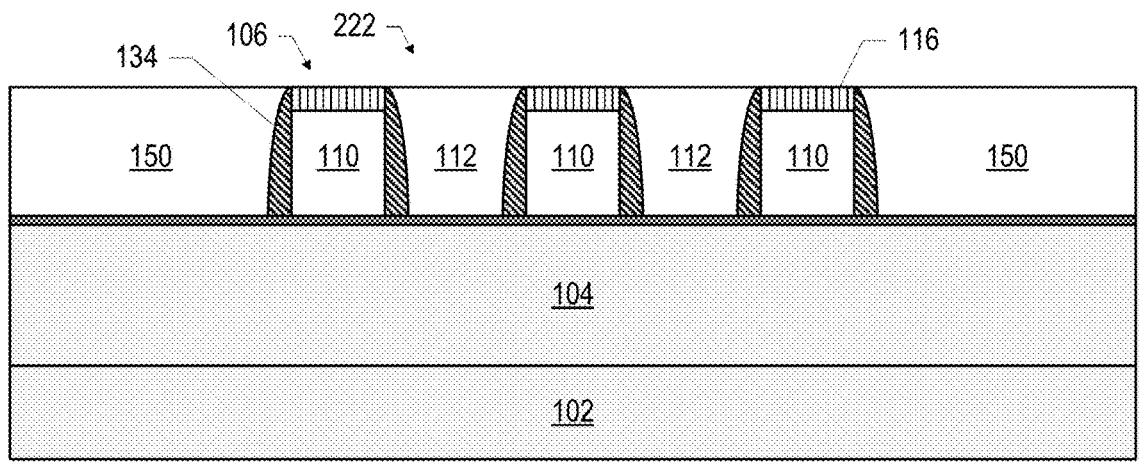

FIG. 26 is a cross-sectional view of an assembly 222 subsequent to planarizing the assembly 220 (FIG. 25) to remove the gate metal 112 above the gates 106. In some embodiments, the assembly 220 may be planarized using a CMP technique. Some of the remaining gate metal 112 may fill the areas between adjacent ones of the gates 106, while other portions 150 of the remaining gate metal 112 may be located "outside" of the gates 106.

Figure 27:
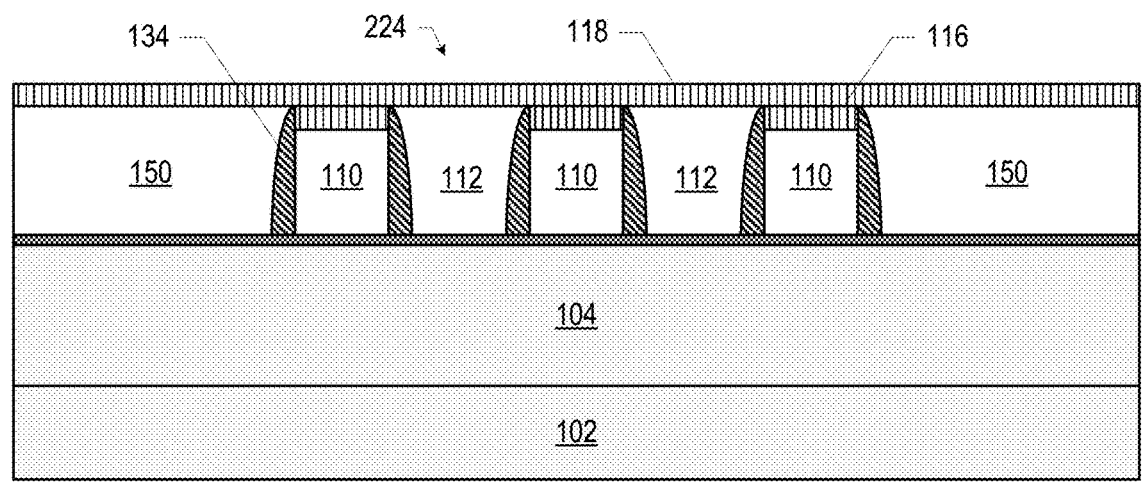

FIG. 27 is a cross-sectional view of an assembly 224 subsequent to providing a hardmask 118 on the planarized surface of the assembly 222 (FIG. 26). The hardmask 118 may be formed of any of the materials discussed above with reference to the hardmask 116, for example.

Figure 28:
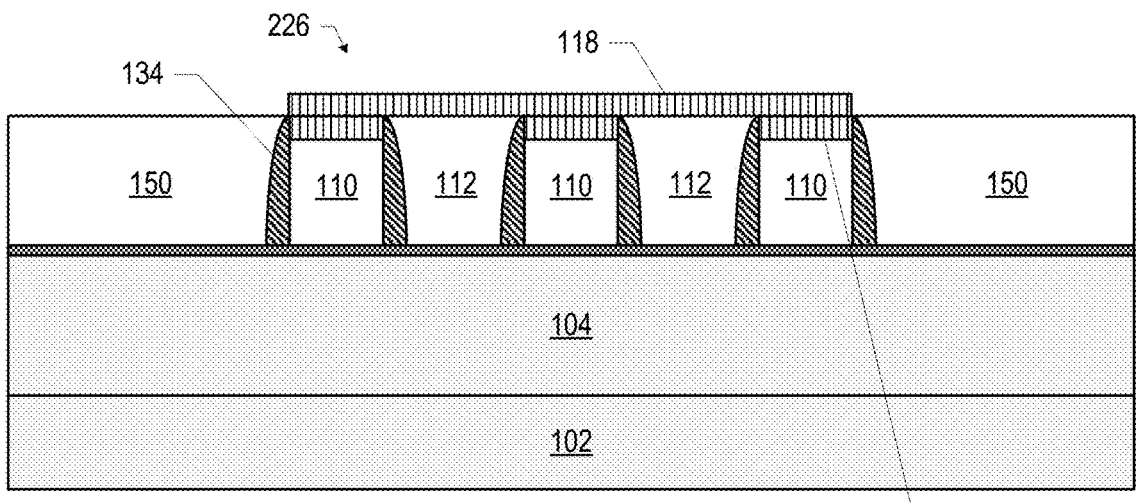

FIG. 28 is a cross-sectional view of an assembly 226 subsequent to patterning the hardmask 118 of the assembly 224 (FIG. 27). The pattern applied to the hardmask 118 may extend over the hardmask 116 (and over the gate metal 110 of the gates 106, as well as over the locations for the gates 108) (as illustrated in FIG. 11). The hardmask 118 may be non-coplanar with the hardmask 116, as illustrated in FIG. 28. The hardmask 118 illustrated in FIG. 28 may thus be a common, continuous portion of hardmask 118 that extends over all of the hardmask 116. Examples of embodiments in which the hardmask 118 is not disposed over the entirety of the hardmask 116 are discussed below with reference to FIGS. 45-47 and 54. The hardmask 118 may be patterned using any of the techniques discussed above with reference to the patterning of the hardmask 116, for example.

Figure 29:
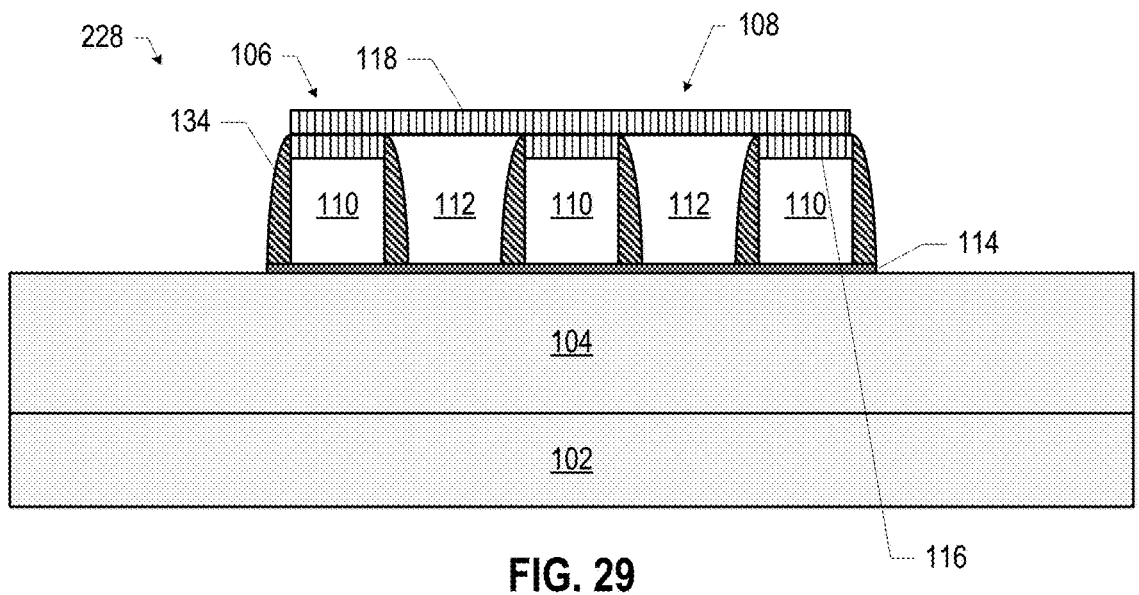

FIG. 29 is a cross-sectional view of an assembly 228 subsequent to etching the assembly 226 (FIG. 28) to remove the portions 150 that are not protected by the patterned hardmask 118 to form the gates 108. Portions of the hardmask 118 may remain on top of the hardmask 116, as shown. The operations performed on the assembly 226 may include removing any gate dielectric 114 that is "exposed" on the fin 104, as shown. The excess gate dielectric 114 may be removed using any suitable technique, such as chemical etching or silicon bombardment.

Figure 30:
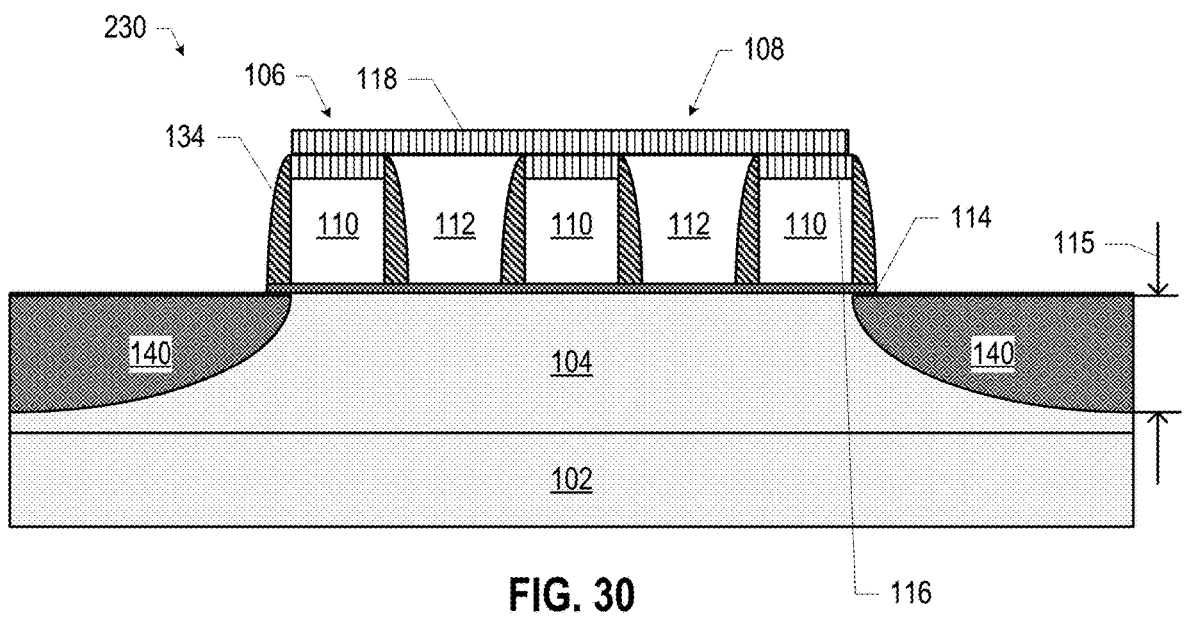

FIG. 30 is a cross-sectional view of an assembly 230 subsequent to doping the fins 104 of the assembly 228 (FIG. 29) to form doped regions 140 in the portions of the fins 104 "outside" of the gates 106/108. The type of dopant used to form the doped regions 140 may depend on the type of quantum dot desired, as discussed above. In some embodiments, the doping may be performed by ion implantation. For example, when the quantum dot 142 is to be an electron-type quantum dot 142, the doped regions 140 may be formed by ion implantation of phosphorous, arsenic, or another n-type material. When the quantum dot 142 is to be a hole-type quantum dot 142, the doped regions 140 may be formed by ion implantation of boron or another p-type material. An annealing process that activates the dopants and causes them to diffuse farther into the fins 104 may follow the ion implantation process. The depth of the doped regions 140 may take any suitable value; for example, in some embodiments, the doped regions 140 may extend into the fin 104 to a depth 115 between 500 Angstroms and 1000 Angstroms.

The outer spacers 134 on the outer gates 106 may provide a doping boundary, limiting diffusion of the dopant from the doped regions 140 into the area under the gates 106/108. As shown, the doped regions 140 may extend under the adjacent outer spacers 134. In some embodiments, the doped regions 140 may extend past the outer spacers 134 and under the gate metal 110 of the outer gates 106, may extend only to the boundary between the outer spacers 134 and the adjacent gate metal 110, or may terminate under the outer spacers 134 and not reach the boundary between the outer spacers 134 and the adjacent gate metal 110. Examples of such embodiments are discussed below with reference to FIGS. 55 and 56. The doping concentration of the doped regions 140 may, in some embodiments, be between $10^{17}/cm^3$ and $10^{20}/cm^3$.

Figure 31:
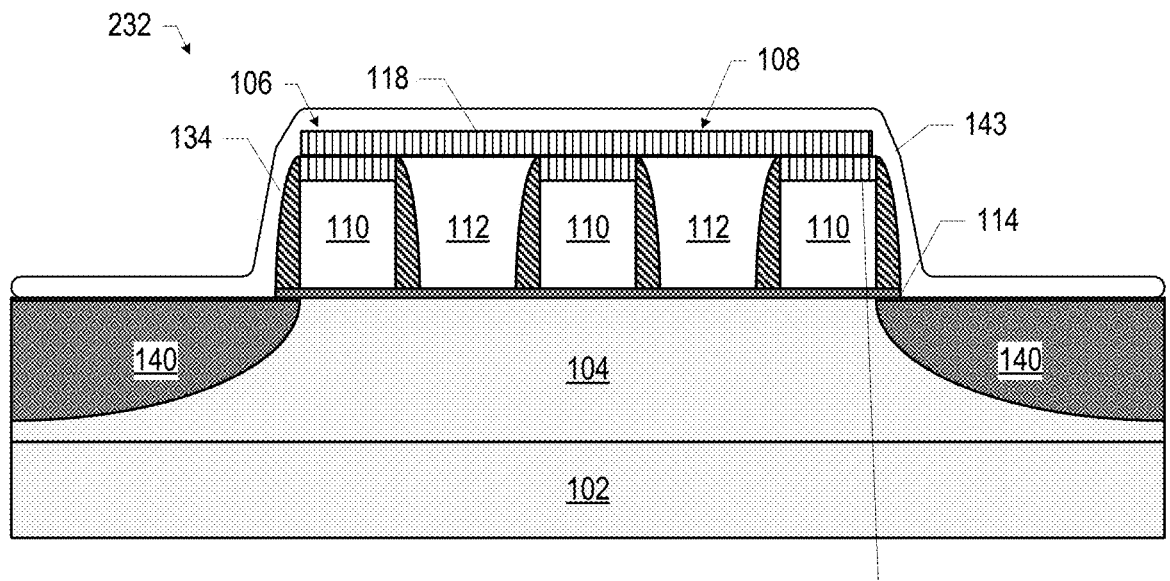

FIG. 31 is a cross-sectional side view of an assembly 232 subsequent to providing a layer of nickel or other material 143 over the assembly 230 (FIG. 30). The nickel or other material 143 may be deposited on the assembly 230 using any suitable technique (e.g., a plating technique, CVD, or atomic layer deposition).

Figure 32:
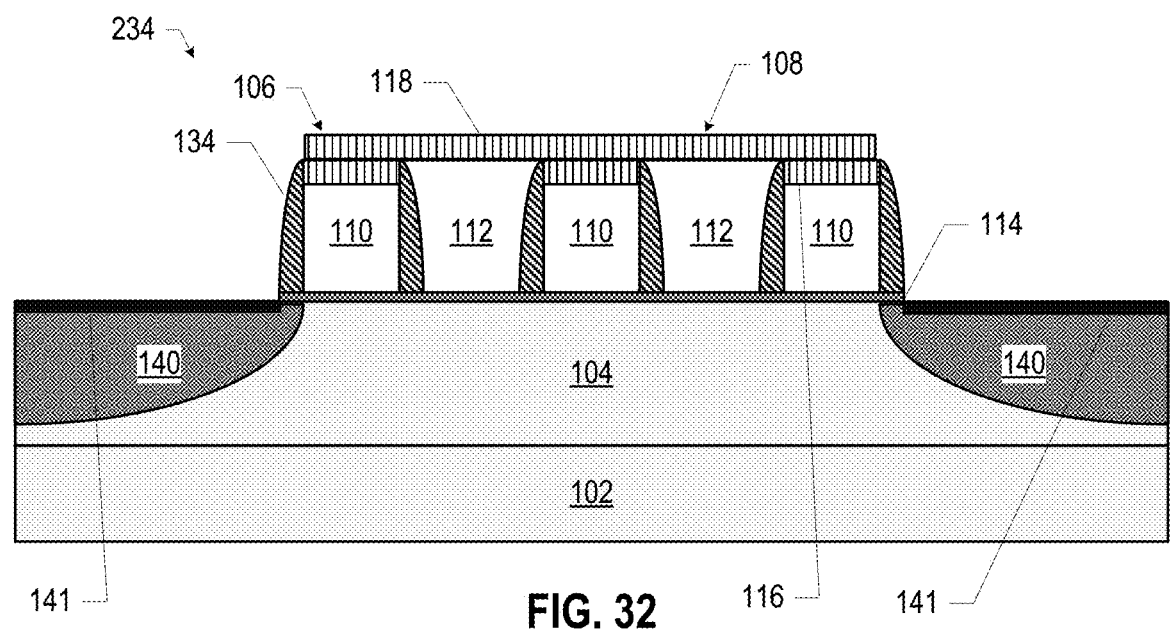

FIG. 32 is a cross-sectional side view of an assembly 234 subsequent to annealing the assembly 232 (FIG. 31) to cause the material 143 to interact with the doped regions 140 to form the interface material 141, then removing the unreacted material 143. When the doped regions 140 include silicon and the material 143 includes nickel, for example, the interface material 141 may be nickel silicide. Materials other than nickel may be deposited in the operations discussed above with reference to FIG. 31 in order to form other interface materials 141, including titanium, aluminum, molybdenum, cobalt, tungsten, or platinum, for example. More generally, the interface material 141 of the assembly 234 may include any of the materials discussed herein with reference to the interface material 141.

Figure 33:
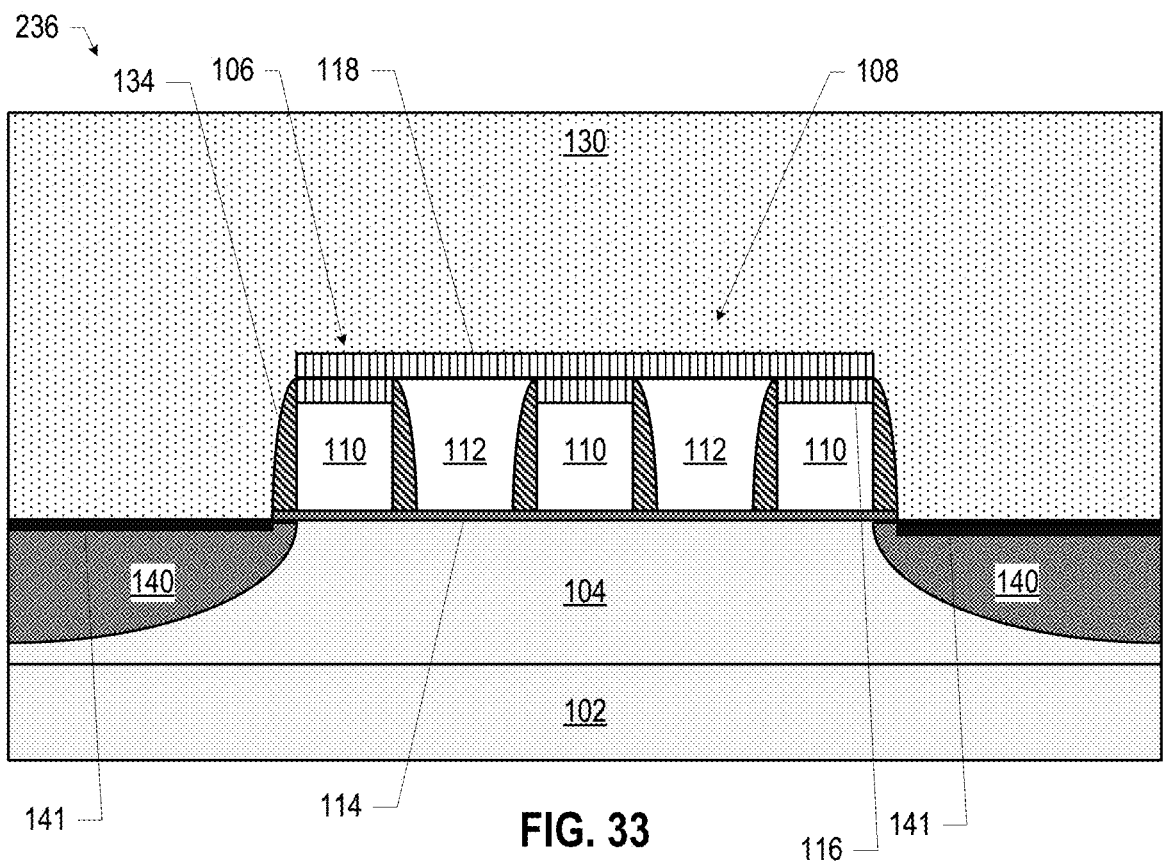

FIG. 33 is a cross-sectional view of an assembly 236 subsequent to providing an insulating material 130 on the assembly 234 (FIG. 32). The insulating material 130 may take any of the forms discussed above. For example, the insulating material 130 may be a dielectric material, such as any of the DDMs 500 disclosed herein. The insulating material 130 may be provided on the assembly 234 using any suitable technique, such as spin-coating, CVD, or PECVD. In some embodiments, the insulating material 130 may be polished back after deposition, and before further processing.

Figure 34:
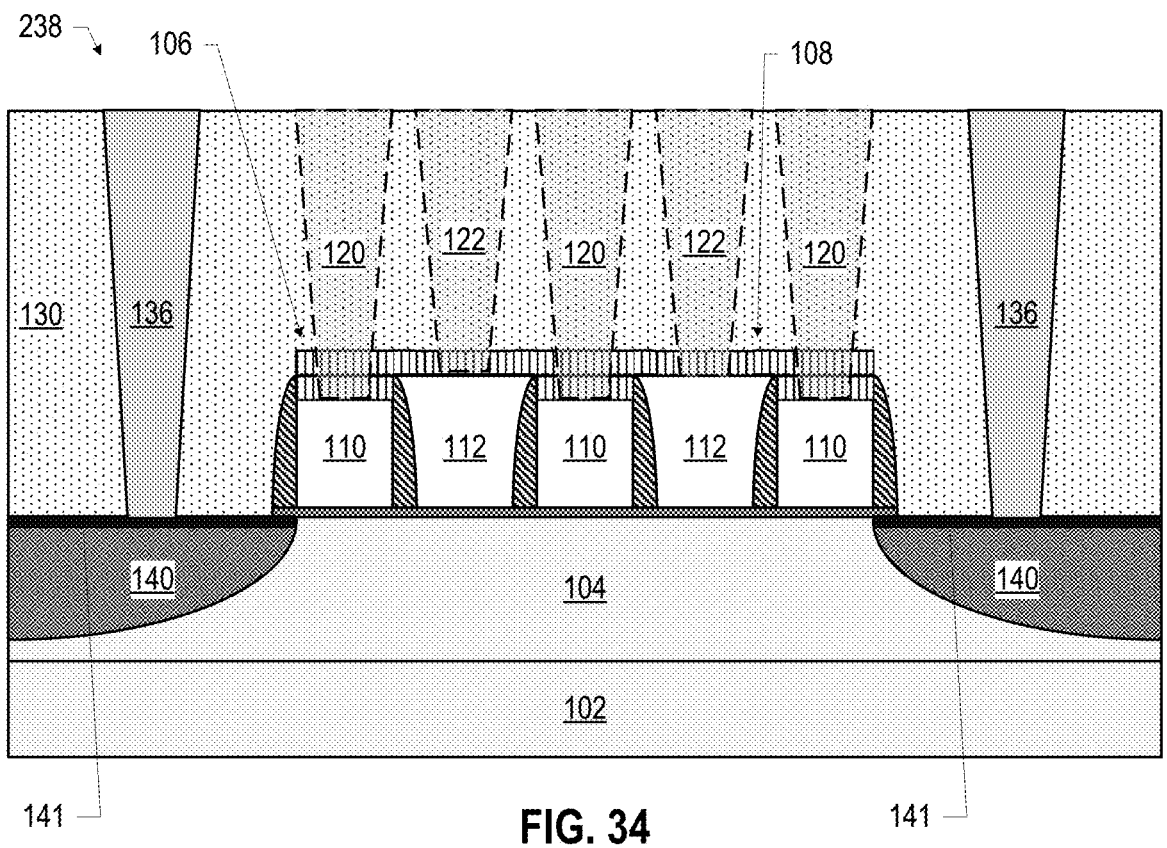

FIG. 34 is a cross-sectional view of an assembly 238 subsequent to forming, in the assembly 236 (FIG. 33), conductive vias 120 through the insulating material 130 (and the hardmasks 116 and 118) to contact the gate metal 110 of the gates 106, conductive vias 122 through the insulating material 130 (and the hardmask 118) to contact the gate metal 112 of the gates 108, and conductive vias 136 through the insulating material 130 to contact the interface material 141 of the doped regions 140. Further conductive vias and/or lines may be formed on the assembly 238 using conventional interconnect techniques, if desired. The resulting assembly 238 may take the form of the quantum dot device 100 discussed above with reference to FIGS. 10-12. In some embodiments, the assembly 236 may be planarized to remove the hardmasks 116 and 118, then additional insulating material 130 may be provided on the planarized surface before forming the conductive vias 120, 122, and 136; in such an embodiment, the hardmasks 116 and 118 would not be present in the quantum dot device 100.

As discussed above, the base 102 and the fin 104 of a quantum dot device 100 may be formed from a substrate 144 and a quantum well stack 146 disposed on the substrate 144.

Figure 35:
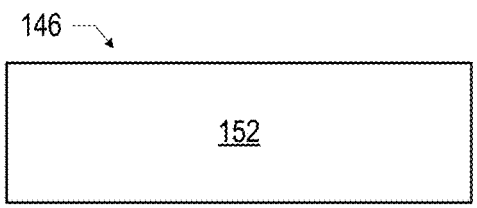
FIGS. 35-37 are cross-sectional views of various examples of quantum well stacks that may be used in a quantum dot device, in accordance with various embodiments.
Figure 36:
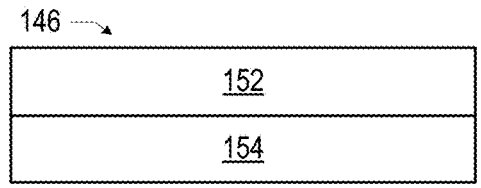
Figure 37:
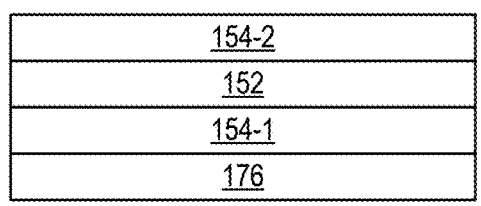

The quantum well stack 146 may include a quantum well layer in which a 2DEG may form during operation of the quantum dot device 100. The quantum well stack 146 may take any of a number of forms, several of which are illustrated in FIGS. 35-37. The various layers in the quantum well stacks 146 discussed below may be grown on the substrate 144 (e.g., using epitaxial processes).

FIG. 35 is a cross-sectional view of a quantum well stack 146 including only a quantum well layer 152. The quantum well layer 152 may be disposed on the substrate 144 (e.g., as discussed above with reference to FIG. 14), and may be formed of a material such that, during operation of the quantum dot device 100, a 2DEG may form in the quantum well layer 152 proximate to the upper surface of the quantum well layer 152. The gate dielectric 114 of the gates 106/108 may be disposed on the upper surface of the quantum well layer 152 (e.g., as discussed above with reference to FIG. 20). In some embodiments, the quantum well layer 152 of FIG. 35 may be formed of intrinsic silicon, and the gate dielectric 114 may be formed of silicon oxide; in such an arrangement, during use of the quantum dot device 100, a 2DEG may form in the intrinsic silicon at the interface between the intrinsic silicon and the silicon oxide. Embodiments in which the quantum well layer 152 of FIG. 35 is formed of intrinsic silicon may be particularly advantageous for electron-type quantum dot devices 100. In some embodiments, the quantum well layer 152 of FIG. 35 may be formed of intrinsic germanium, and the gate dielectric 114 may be formed of germanium oxide; in such an arrangement, during use of the quantum dot device 100, a 2DEG may form in the intrinsic germanium at the interface between the intrinsic germanium and the germanium oxide. Such embodiments may be particularly advantageous for hole-type quantum dot devices 100. In some embodiments, the quantum well layer 152 may be strained, while in other embodiments, the quantum well layer 152 may not be strained. The thicknesses (i.e., z-heights) of the layers in the quantum well stack 146 of FIG. 35 may take any suitable values. For example, in some embodiments, the thickness of the quantum well layer 152 (e.g., intrinsic silicon or germanium) may be between 0.8 microns and 1.2 microns.

FIG. 36 is a cross-sectional view of a quantum well stack 146 including a quantum well layer 152 and a barrier layer 154. The quantum well stack 146 may be disposed on a substrate 144 (e.g., as discussed above with reference to FIG. 14) such that the barrier layer 154 is disposed between the quantum well layer 152 and the substrate 144. The barrier layer 154 may provide a potential barrier between the quantum well layer 152 and the substrate 144. As discussed above with reference to FIG. 35, the quantum well layer 152 of FIG. 36 may be formed of a material such that, during operation of the quantum dot device 100, a 2DEG may form in the quantum well layer 152 proximate to the upper surface of the quantum well layer 152. For example, in some embodiments in which the substrate 144 is formed of silicon, the quantum well layer 152 of FIG. 36 may be formed of silicon, and the barrier layer 154 may be formed of silicon germanium. The germanium content of this silicon germanium may be 20-80 atomic-% (e.g., 30 atomic-%). In some embodiments in which the quantum well layer 152 is formed of germanium, the barrier layer 154 may be formed of silicon germanium (with a germanium content of 20-80 atomic-% (e.g., 70 atomic-%)). The thicknesses (i.e., z-heights) of the layers in the quantum well stack 146 of FIG. 36 may take any suitable values. For example, in some embodiments, the thickness of the barrier layer 154 (e.g., silicon germanium) may be between 0 nanometers and 400 nanometers. In some embodiments, the thickness of the quantum well layer 152 (e.g., silicon or germanium) may be between 5 nanometers and 30 nanometers.

FIG. 37 is a cross-sectional view of a quantum well stack 146 including a quantum well layer 152 and a barrier layer 154-1, as well as a buffer layer 176 and an additional barrier layer 154-2. The quantum well stack 146 may be disposed on the substrate 144 (e.g., as discussed above with reference to FIG. 14) such that the buffer layer 176 is disposed between the barrier layer 154-1 and the substrate 144. The buffer layer 176 may be formed of the same material as the barrier layer 154, and may be present to trap defects that form in this material as it is grown on the substrate 144. In some embodiments, the buffer layer 176 may be grown under different conditions (e.g., deposition temperature or growth rate) from the barrier layer 154-1. In particular, the barrier layer 154-1 may be grown under conditions that achieve fewer defects than the buffer layer 176. In some embodiments in which the buffer layer 176 includes silicon germanium, the silicon germanium of the buffer layer 176 may have a germanium content that varies from the substrate 144 to the barrier layer 154-1; for example, the silicon germanium of the buffer layer 176 may have a germanium content that varies from zero percent at the silicon substrate 144 to a nonzero percent (e.g., 30 atomic-%) at the barrier layer 154-1. The thicknesses (i.e., z-heights) of the layers in the quantum well stack 146 of FIG. 37 may take any suitable values. For example, in some embodiments, the thickness of the buffer layer 176 (e.g., silicon germanium) may be between 0.3 microns and 4 microns (e.g., between 0.3 microns and 2 microns, or 0.5 microns). In some embodiments, the thickness of the barrier layer 154-1 (e.g., silicon germanium) may be between 0 nanometers and 400 nanometers. In some embodiments, the thickness of the quantum well layer 152 (e.g., silicon or germanium) may be between 5 nanometers and 30 nanometers (e.g., 10 nanometers). The barrier layer 154-2, like the barrier layer 154-1, may provide a potential energy barrier around the quantum well layer 152, and may take the form of any of the embodiments of the barrier layer 154-1. In some embodiments, the thickness of the barrier layer 154-2 (e.g., silicon germanium) may be between 25 nanometers and 75 nanometers (e.g., 32 nanometers).

As discussed above with reference to FIG. 36, the quantum well layer 152 of FIG. 37 may be formed of a material such that, during operation of the quantum dot device 100, a 2DEG may form in the quantum well layer 152 proximate to the upper surface of the quantum well layer 152. For example, in some embodiments in which the substrate 144 is formed of silicon, the quantum well layer 152 of FIG. 37 may be formed of silicon, and the barrier layer 154-1 and the buffer layer 176 may be formed of silicon germanium. In some such embodiments, the silicon germanium of the buffer layer 176 may have a germanium content that varies from the substrate 144 to the barrier layer 154-1; for example, the silicon germanium of the buffer layer 176 may have a germanium content that varies from zero percent at the silicon substrate 144 to a nonzero percent (e.g., 30%) at the barrier layer 154-1. The barrier layer 154-1 may in turn have a germanium content equal to the nonzero percent. In other embodiments, the buffer layer 176 may have a germanium content equal to the germanium content of the barrier layer 154-1 but may be thicker than the barrier layer 154-1 so as to absorb the defects that arise during growth.

In some embodiments, the quantum well layer 152 of FIG. 37 may be formed of germanium, and the buffer layer 176 and the barrier layer 154-1 may be formed of silicon germanium. In some such embodiments, the silicon germanium of the buffer layer 176 may have a germanium content that varies from the substrate 144 to the barrier layer 154-1; for example, the silicon germanium of the buffer layer 176 may have a germanium content that varies from zero percent at the substrate 144 to a nonzero percent (e.g., 70 atomic-%) at the barrier layer 154-1. The barrier layer 154-1 may in turn have a germanium content equal to the nonzero percent. In other embodiments, the buffer layer 176 may have a germanium content equal to the germanium content of the barrier layer 154-1 but may be thicker than the barrier layer 154-1 so as to absorb the defects that arise during growth. In some embodiments of the quantum well stack 146 of FIG. 37, the buffer layer 176 and/or the barrier layer 154-2 may be omitted.

The substrate 144 and the quantum well stack 146 may be distributed between the base 102 and the fins 104 of the quantum dot device 100, as discussed above. This distribution may occur in any of a number of ways. For example, FIGS. 38-44 illustrate example base/fin arrangements 158 that may be used in a quantum dot device 100, in accordance with various embodiments.

Figure 38:
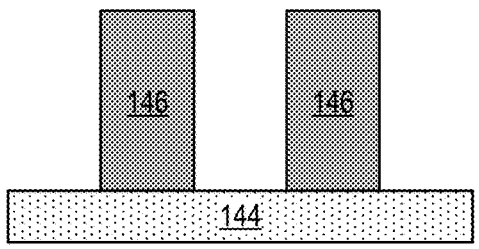
FIGS. 38-44 illustrate example base/fin arrangements that may be used in a quantum dot device, in accordance with various embodiments.

In the base/fin arrangement 158 of FIG. 38, the quantum well stack 146 may be included in the fins 104, but not in the base 102. The substrate 144 may be included in the base 102, but not in the fins 104. When the base/fin arrangement 158 of FIG. 38 is used in the manufacturing operations discussed with reference to FIGS. 14-15, the fin etching may etch through the quantum well stack 146, and stop when the substrate 144 is reached.

Figure 39:
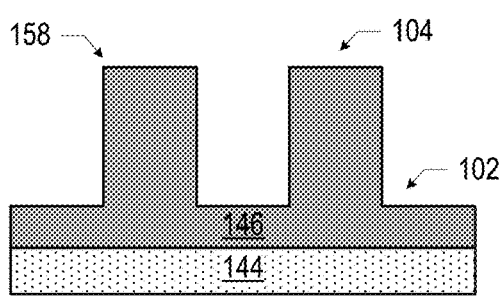
Figure 40:
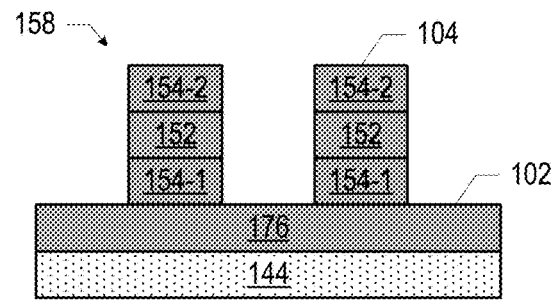

In the base/fin arrangement 158 of FIG. 39, the quantum well stack 146 may be included in the fins 104, as well as in a portion of the base 102. A substrate 144 may be included in the base 102 as well, but not in the fins 104. When the base/fin arrangement 158 of FIG. 39 is used in the manufacturing operations discussed with reference to FIGS. 14-15, the fin etching may etch partially through the quantum well stack 146, and stop before the substrate 144 is reached. FIG. 40 illustrates a particular embodiment of the base/fin arrangement 158 of FIG. 39. In the embodiment of FIG. 40, the quantum well stack 146 of FIG. 37 is used; the fins 104 include the barrier layer 154-1, the quantum well layer 152, and the barrier layer 154-2, while the base 102 includes the buffer layer 176 and the substrate 144.

Figure 41:
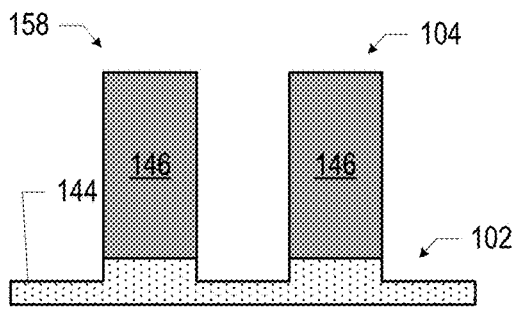
Figure 42:
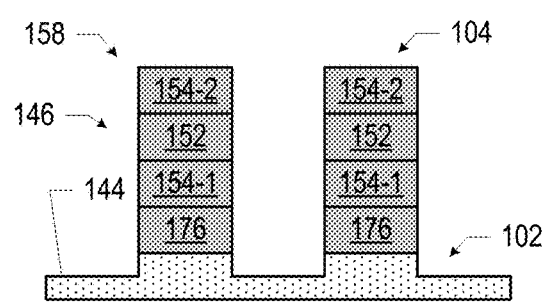

In the base/fin arrangement 158 of FIG. 41, the quantum well stack 146 may be included in the fins 104, but not the base 102. The substrate 144 may be partially included in the fins 104, as well as in the base 102. When the base/fin arrangement 158 of FIG. 41 is used in the manufacturing operations discussed with reference to FIGS. 14-15, the fin etching may etch through the quantum well stack 146 and into the substrate 144 before stopping. FIG. 42 illustrates a particular embodiment of the base/fin arrangement 158 of FIG. 41. In the embodiment of FIG. 42, the quantum well stack 146 of FIG. 37 is used; the fins 104 include the quantum well stack 146 and a portion of the substrate 144, while the base 102 includes the remainder of the substrate 144.

Figure 43:
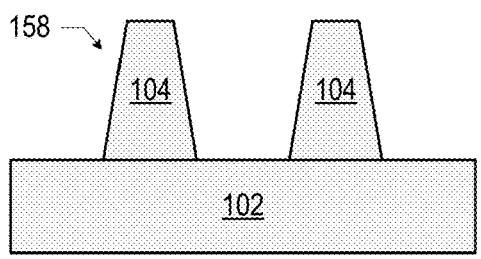
Figure 44:
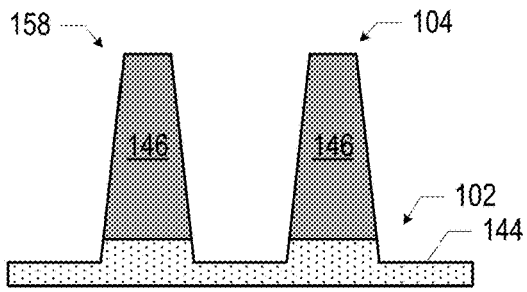

Although the fins 104 have been illustrated in many of the preceding figures as substantially rectangular with parallel sidewalls, this is simply for ease of illustration, and the fins 104 may have any suitable shape (e.g., shape appropriate to the manufacturing processes used to form the fins 104). For example, as illustrated in the base/fin arrangement 158 of FIG. 43, in some embodiments, the fins 104 may be tapered. In some embodiments, the fins 104 may taper by 3-10 nanometers in x-width for every 100 nanometers in z-height (e.g., 5 nanometers in x-width for every 100 nanometers in z-height). When the fins 104 are tapered, the wider end of the fins 104 may be the end closest to the base 102, as illustrated in FIG. 43. FIG. 44 illustrates a particular embodiment of the base/fin arrangement 158 of FIG. 43. In FIG. 44, the quantum well stack 146 is included in the tapered fins 104 while a portion of the substrate 144 is included in the tapered fins and a portion of the substrate 144 provides the base 102.

Figure 45:
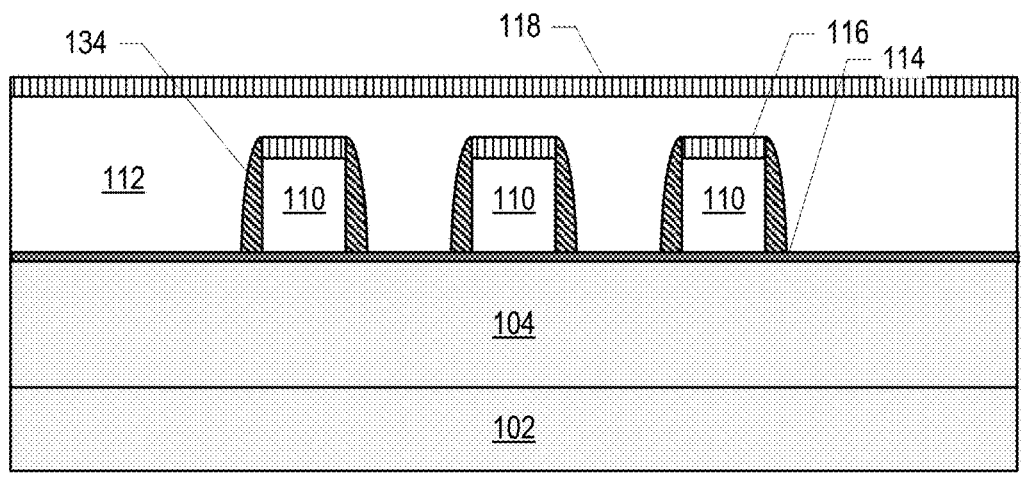
FIGS. 45-47 illustrate various example stages in the manufacture of alternative gate arrangements that may be included in a quantum dot device, in accordance with various embodiments.
Figure 46:
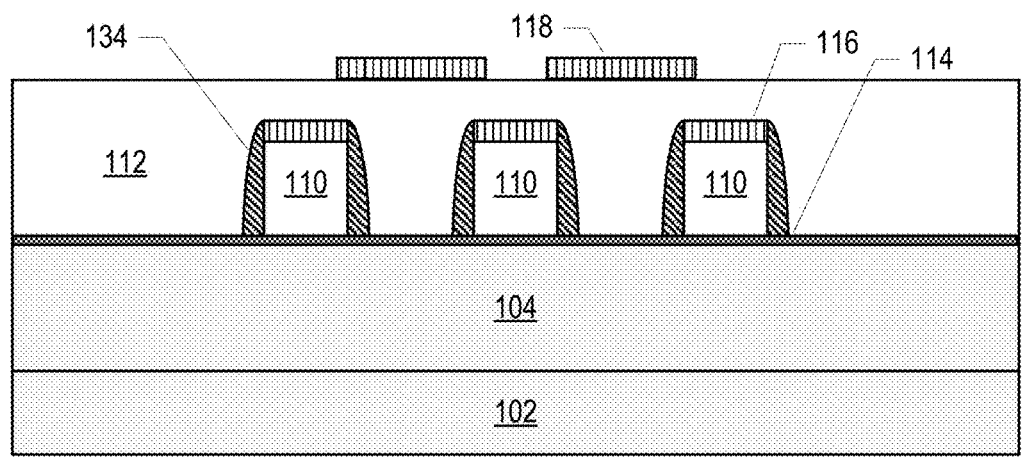
Figure 47:
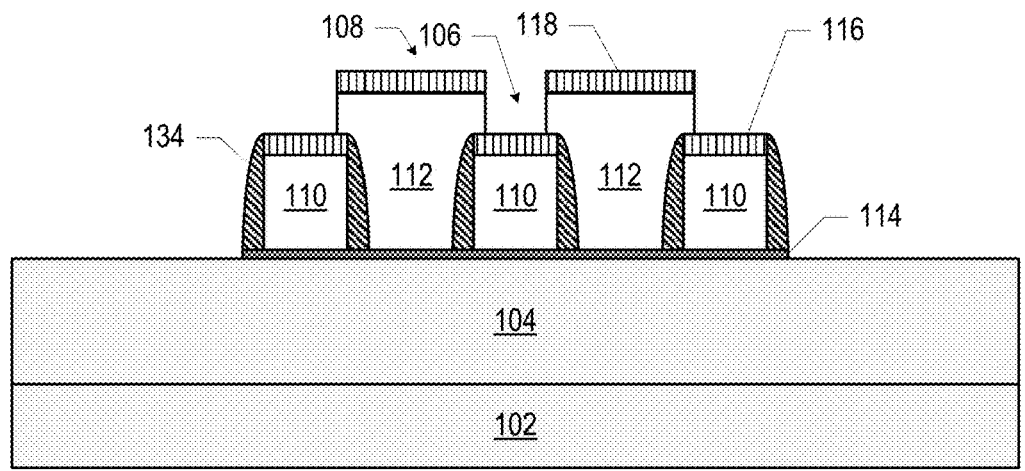

In the embodiment of the quantum dot device 100 illustrated in FIG. 11, the z-height of the gate metal 112 of the gates 108 may be approximately equal to the sum of the z-height of the gate metal 110 and the z-height of the hardmask 116, as shown. Also in the embodiment of FIG. 11, the gate metal 112 of the gates 108 may not extend in the x-direction beyond the adjacent spacers 134. In other embodiments, the z-height of the gate metal 112 of the gates 108 may be greater than the sum of the z-height of the gate metal 110 and the z-height of the hardmask 116, and in some such embodiments, the gate metal 112 of the gates may extend beyond the spacers 134 in the x-direction. FIGS. 45-47 illustrate various example stages in the manufacture of alternative gate arrangements that may be included in a quantum dot device 100, in accordance with various embodiments.

FIG. 45 illustrates an assembly 242 subsequent to providing the gate metal 112 and a hardmask 118 on the assembly 218 (FIG. 24). The assembly 242 may be similar to the assembly 224 of FIG. 27 (and may be formed using any of the techniques discussed above with reference to FIGS. 25-27), but may include additional gate metal 112 between the hardmask 116 and the hardmask 118, of any desired thickness. In some embodiments, the gate metal 112 may be planarized prior to provision of the hardmask 118, but the hardmask 118 may still be spaced away from the hardmask 116 in the z-direction by the gate metal 112, as shown in FIG. 45.

FIG. 46 illustrates an assembly 244 subsequent to patterning the hardmask 118 of the assembly 242 (FIG. 45). The pattern applied to the hardmask 118 may include the locations for the gates 108, as discussed below. The hardmask 118 may be non-coplanar with the hardmask 116, as illustrated in FIG. 45, and may extend "over" at least a portion of the hardmask 116 (and thus over the gate metal 110 of the gates 106).

FIG. 47 illustrates an assembly 246 subsequent to etching the assembly 244 (FIG. 46) to remove the portions 150 that are not protected by the patterned hardmask 118 to form the gates 108. The gate metal 112 of the gates 106 may extend "over" the hardmask 116 of the gates 108, and may be electrically insulated from the gate metal 110 by the hardmask 116. In the embodiment illustrated in FIG. 47, the z-height of the gate metal 112 of the gates 108 may be greater than the sum of the z-height of the gate metal 110 and the z-height of the hardmask 116 of the gates 106. Additionally, the gate metal 112 of the gates 108 may extend beyond the spacers 134 in the x-direction, as shown. Further manufacturing operations may be performed on the assembly 246, as discussed above with reference to FIGS. 30-34.

Figure 48:
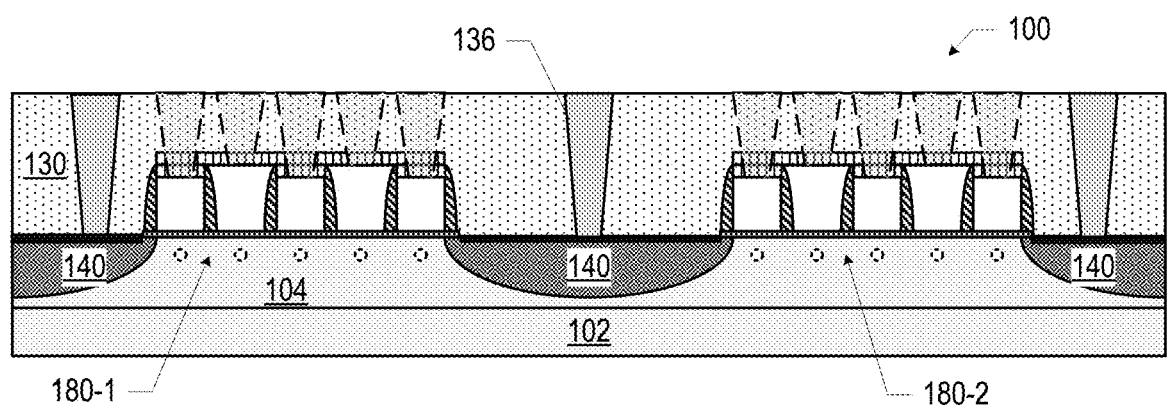
FIG. 48 illustrates an embodiment of a quantum dot device having multiple groups of gates on a single fin, in accordance with various embodiments.

As noted above, a single fin 104 may include multiple groups of gates 106/108, spaced apart along the fin by a doped region 140. FIG. 48 is a cross-sectional view of an example of such a quantum dot device 100 having multiple groups of gates 180 on a single fin 104, in accordance with various embodiments. Each of the groups 180 may include gates 106/108 (not labeled in FIG. 48 for ease of illustration) that may take the form of any of the embodiments of the gates 106/108 discussed herein. A doped region 140 (and its interface material 141) may be disposed between two adjacent groups 180 (labeled in FIG. 48 as groups 180-1 and 180-2), and may provide a common reservoir for both groups 180. In some embodiments, this "common" doped region 140 may be electrically contacted by a single conductive via 136. The particular number of gates 106/108 illustrated in FIG. 48, and the particular number of groups 180, is simply illustrative, and a fin 104 may include any suitable number of gates 106/108 arranged in any suitable number of groups 180.

As discussed above with reference to FIGS. 10-12, in some embodiments in which the gate dielectric 114 is not a layer shared commonly between the gates 108 and 106, but instead is separately deposited on the fin 104 between the spacers 134, the gate dielectric 114 may extend at least partially up the sides of the spacers 134, and the gate metal 112 may extend between the portions of gate dielectric 114 on the spacers 134. FIGS. 49-53 illustrate various alternative stages in the manufacture of such an embodiment of a quantum dot device 100, in accordance with various embodiments. In particular, the operations illustrated in FIGS. 49-53 may take the place of the operations illustrated in FIGS. 22-24.

Figure 49:
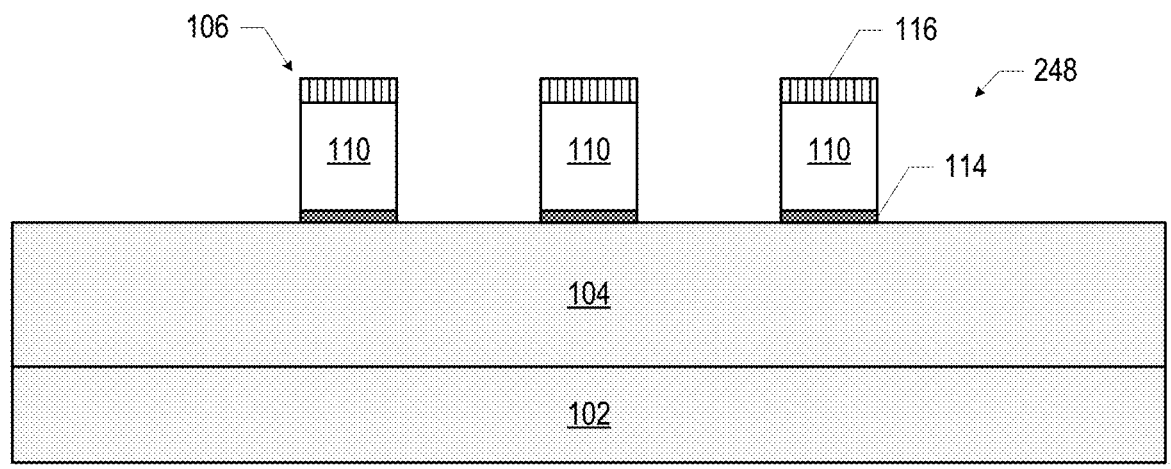
FIGS. 49-53 illustrate various alternative stages in the manufacture of a quantum dot device, in accordance with various embodiments.

FIG. 49 is a cross-sectional view of an assembly 248 subsequent to etching the assembly 212 (FIG. 21) to remove the gate metal 110, and the gate dielectric 114 that is not protected by the patterned hardmask 116, to form the gates 106.

Figure 50:
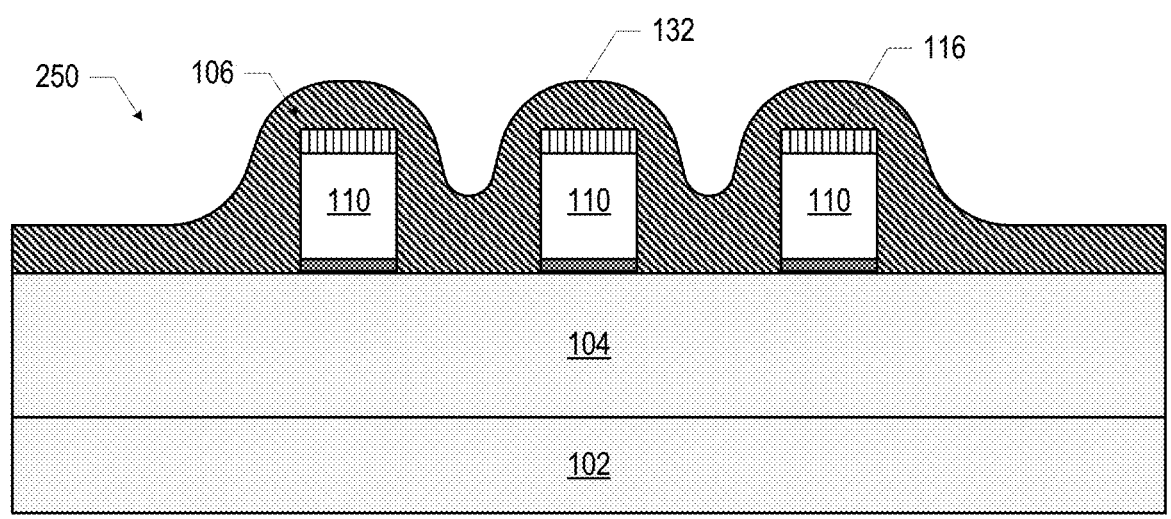

FIG. 50 is a cross-sectional view of an assembly 250 subsequent to providing spacer material 132 on the assembly 248 (FIG. 49). The deposition of the spacer material 132 may take any of the forms discussed above with reference to FIG. 23, for example.

Figure 51:
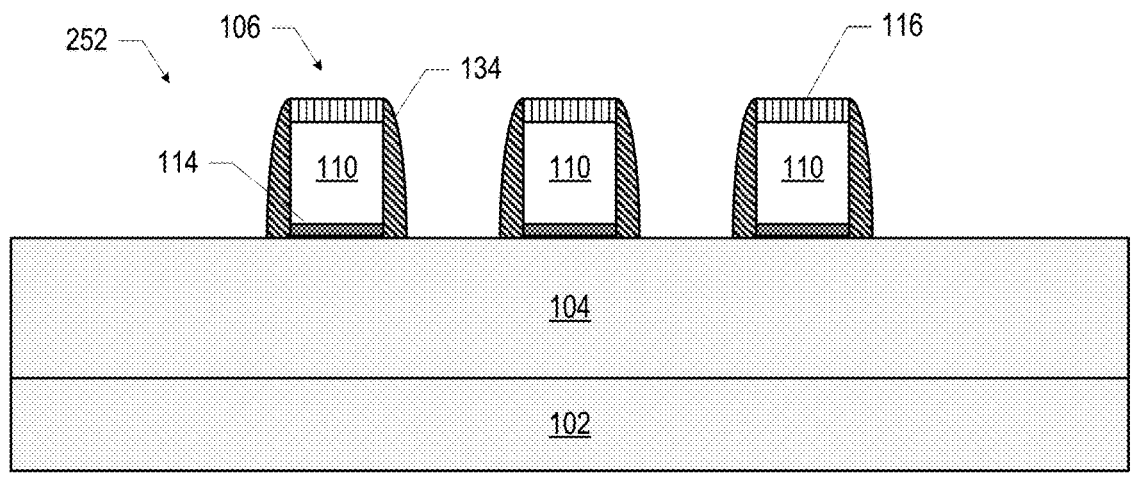

FIG. 51 is a cross-sectional view of an assembly 252 subsequent to etching the spacer material 132 of the assembly 250 (FIG. 50), leaving spacers 134 formed of the spacer material 132 on the sides of the gates 106 (e.g., on the sides of the hardmask 116, the gate metal 110, and the gate dielectric 114). The etching of the spacer material 132 may take any of the forms discussed above with reference to FIG. 24, for example.

Figure 52:
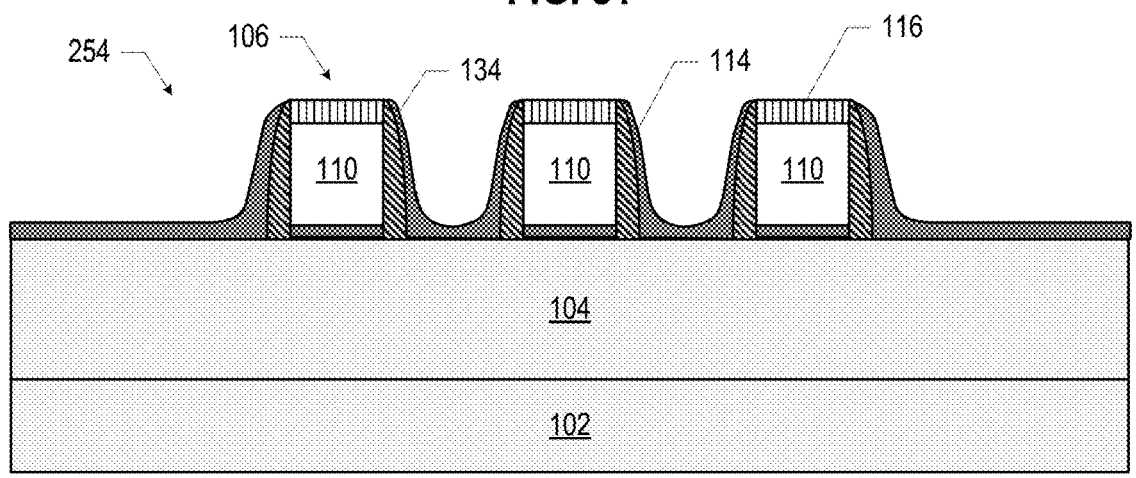

FIG. 52 is a cross-sectional view of an assembly 254 subsequent to providing a gate dielectric 114 on the fin 104 between the gates 106 of the assembly 252 (FIG. 51). In some embodiments, the gate dielectric 114 provided between the gates 106 of the assembly 252 may be formed by atomic layer deposition (ALD) and, as illustrated in FIG. 52, may cover the exposed fin 104 between the gates 106, and may extend onto the adjacent spacers 134.

Figure 53:
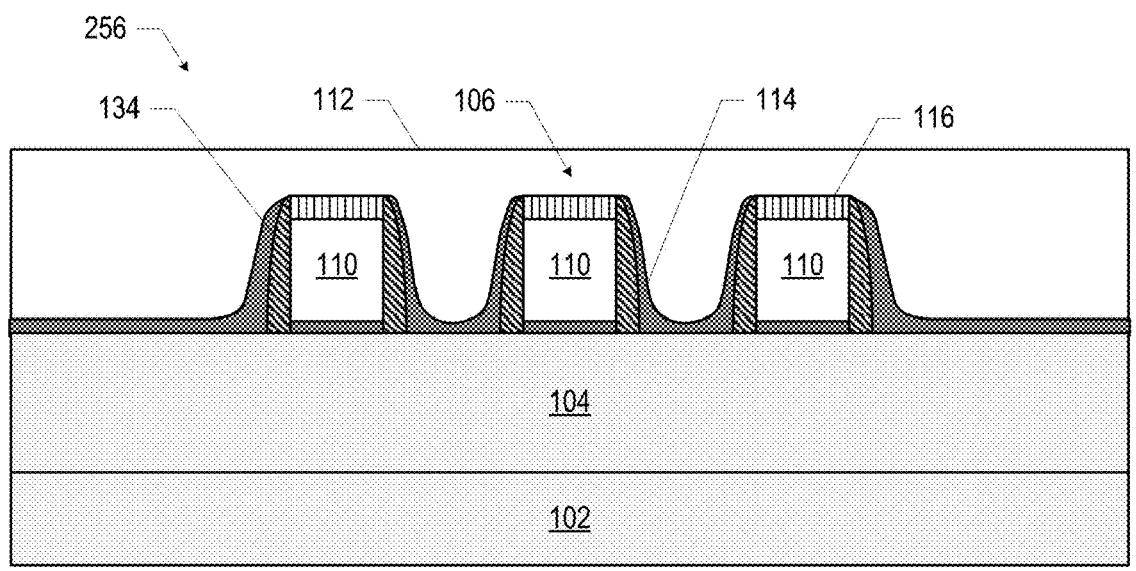

FIG. 53 is a cross-sectional view of an assembly 256 subsequent to providing the gate metal 112 on the assembly 254 (FIG. 52). The gate metal 112 may fill the areas between adjacent ones of the gates 106, and may extend over the tops of the gates 106, as shown. The provision of the gate metal 112 may take any of the forms discussed above with reference to FIG. 25, for example. The assembly 256 may be further processed as discussed above with reference to FIGS. 26-34.

Figure 54:
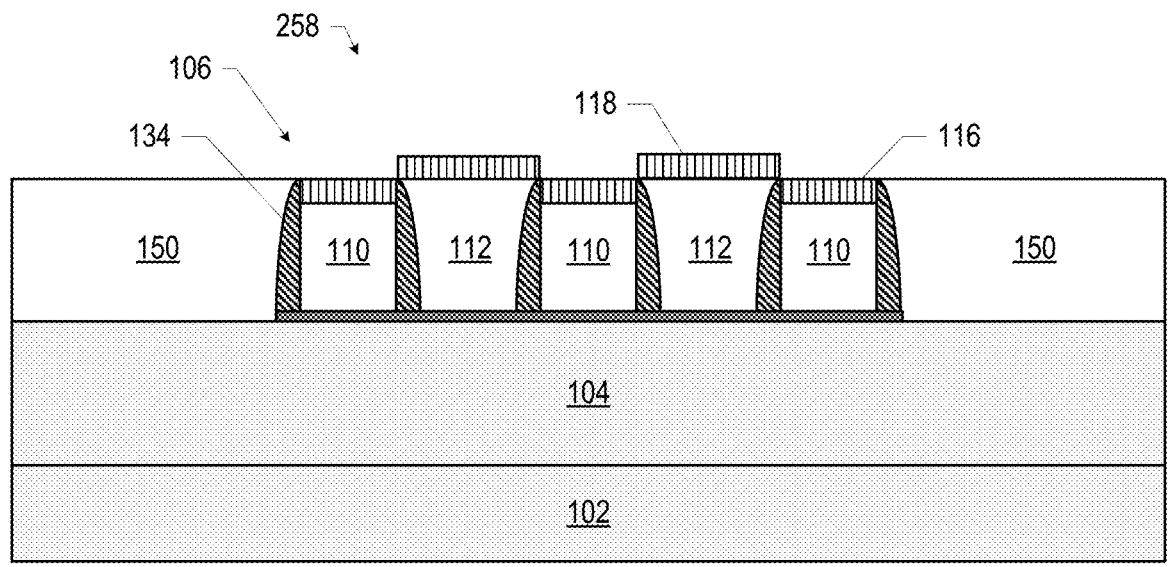
FIG. 54 illustrates an example alternative stage in the manufacture of a quantum dot device, in accordance with various embodiments.

As discussed above with reference to FIG. 28, in some embodiments, the pattern applied to the hardmask 118 (used for patterning the gates 108) may not result in a common, continuous portion of hardmask 118 that extends over all of the hardmask 116. One such example was discussed above with reference to FIGS. 45-47, and another example of such an embodiment is illustrated in FIG. 54. In particular, FIG. 54 is a cross-sectional view of an assembly 258 in which the hardmask 118 of the assembly 224 (FIG. 27) is not patterned to extend over the gates 106, but instead is patterned so as not to extend over the gate metal 110. The assembly 258 may be further processed as discussed above with reference to FIGS. 29-34 (e.g., etching away the excess portions 150, etc.). In some embodiments, the hardmasks 116 and 118 may remain in the quantum dot device 100 as part of the gates 106/108, while in other embodiments, the hardmasks 116 and 118 may be removed.

Figure 55:
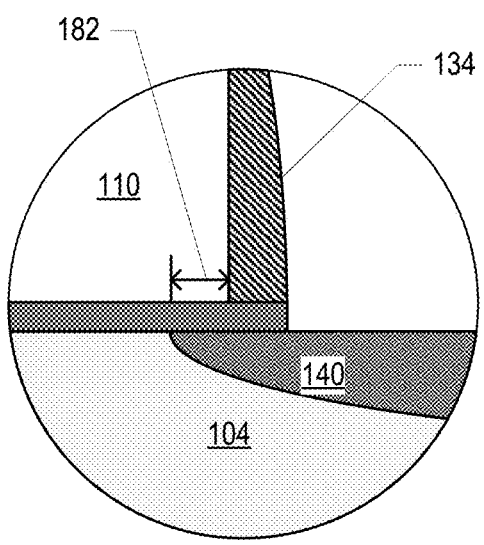
FIGS. 55-56 illustrate detail views of various embodiments of a doped region in a quantum dot device.
Figure 56:
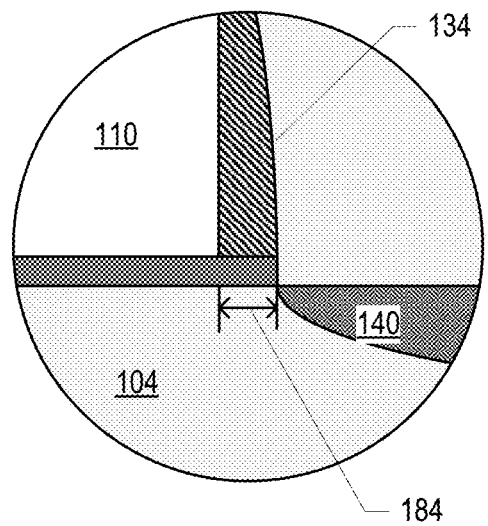

As discussed above with reference to FIGS. 11 and 30, the outer spacers 134 on the outer gates 106 may provide a doping boundary, limiting diffusion of the dopant from the doped regions 140 into the area under the gates 106/108. In some embodiments, the doped regions 140 may extend past the outer spacers 134 and under the outer gates 106. For example, as illustrated in FIG. 55, the doped region 140 may extend past the outer spacers 134 and under the outer gates 106 by a distance 182 between 0 nanometers and 10 nanometers. In some embodiments, the doped regions 140 may not extend past the outer spacers 134 toward the outer gates 106, but may instead "terminate" under the outer spacers 134. For example, as illustrated in FIG. 56, the doped regions 140 may be spaced away from the interface between the outer spacers 134 and the outer gates 106 by a distance 184 between 0 nanometers and 10 nanometers. The interface material 141 is omitted from FIGS. 55 and 56 for ease of illustration.

As discussed above, conductive vias and/or lines may be used to provide electrical interconnects to the gates 106/108 and to the doped regions 140. FIGS. 57-76 illustrate various example stages in the formation of interconnects in a quantum dot device 100, in accordance with various embodiments. In particular, FIGS. 57-76 illustrate techniques that may be used to form the conductive vias 120/122/136, as well as conductive lines and additional conductive vias to create electrical pathways to the gates 106/108 and the doped regions 140. In particular, FIGS. 57-62 illustrate operations that may be used to form the conductive vias 136 of the assembly 238 of FIG. 34, and FIGS. 63-76 illustrate operations that may be used to form additional conductive vias and lines in conductive contact with the conductive vias 136.

Although FIGS. 57-76 explicitly depict the formation of the conductive vias 136 (and additional interconnect structures) to the doped regions 140 (for consistency with the particular cross-sections illustrated in FIGS. 11 and 13-34), this is simply for ease of illustration, and the structure of the interconnects formed in FIGS. 57-76 may be used for interconnects to any of the gates 106/108 (including the conductive vias 120 and 122). Similarly, the manufacturing techniques discussed with reference to the interconnects to the doped regions 140 formed in FIGS. 57-76 may be used to form interconnects to the gates 106/108, as readily recognized.

Figure 57:
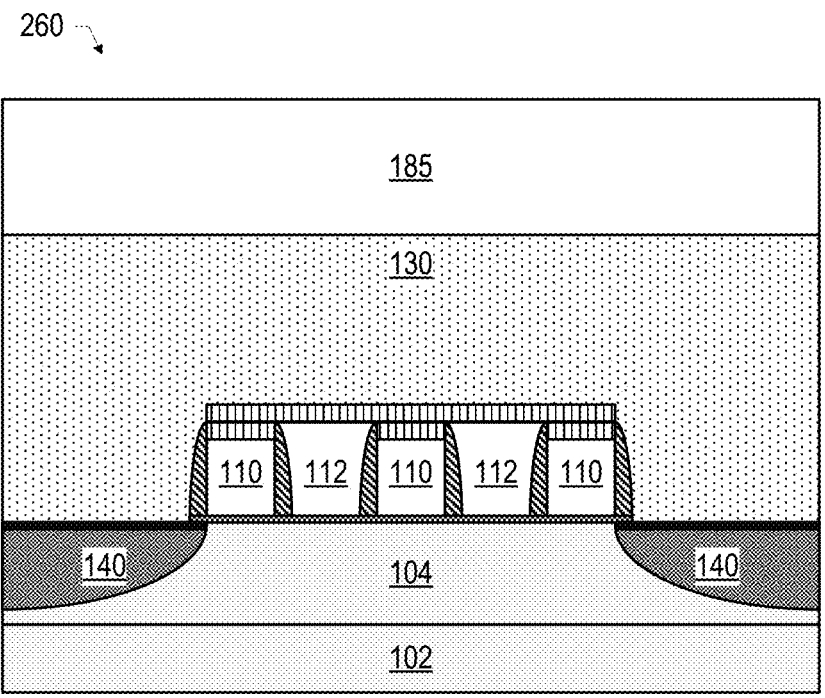
FIGS. 57-76 illustrate various example stages in the formation of interconnects in a quantum dot device, in accordance with various embodiments.

FIG. 57 is a cross-sectional view of an assembly 260 subsequent to providing a resist material 185 on the insulating material 130 of the assembly 236 (FIG. 33). The resist material 185 may be any suitable resist for patterning the insulating material 130, as discussed below with reference to FIG. 59 (e.g., a photoresist).

Figure 58:
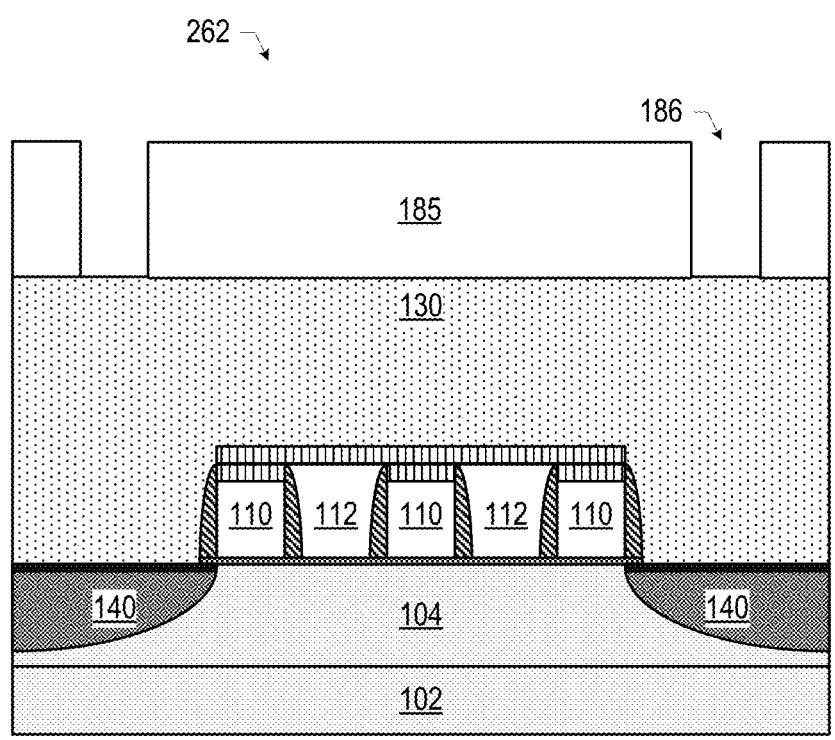

FIG. 58 is a cross-sectional view of an assembly 262 subsequent to patterning the resist material 185 of the assembly 260 (FIG. 57). The patterned resist material 185 may include cavities 186 that extend down to and expose portions of the insulating material 130. The patterning of the resist material 185 may be performed in accordance with any suitable technique (e.g., a photolithography technique).

Figure 59:
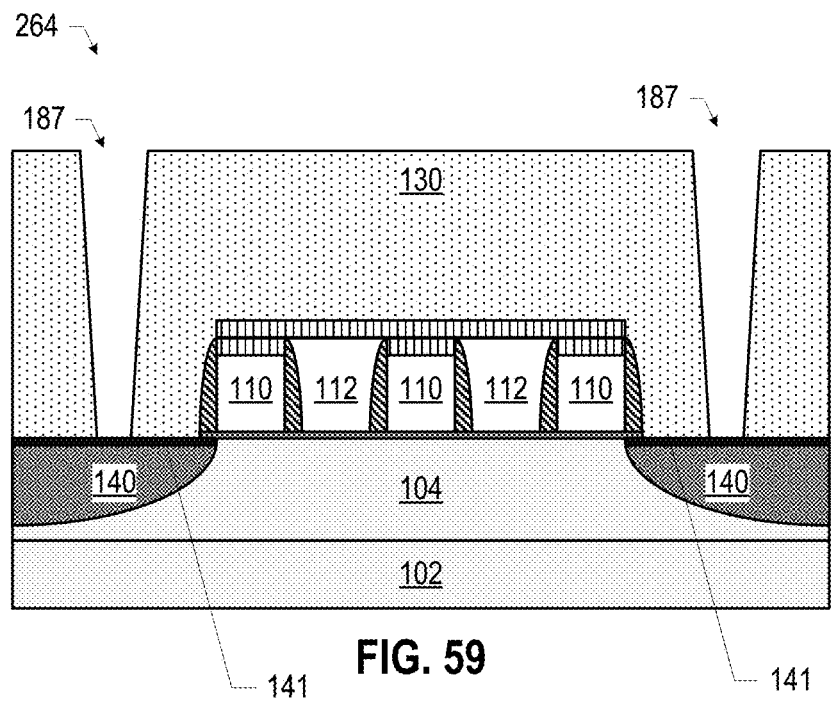

FIG. 59 is a cross-sectional view of an assembly 264 subsequent to etching the insulating material 130 in accordance with the pattern provided by the patterned resist material 185 of the assembly 262 (FIG. 58), and removing the remaining resist material 185. In particular, cavities 187 may be formed in the insulating material 130 at locations corresponding to the locations of the cavities 186 in the resist material 185. The cavities 187 may extend down to the interface material 141 of the doped regions 140. In some embodiments, the cavities 187 may have a taper, and may be narrower closer to the doped regions 140, as illustrated. When the manufacturing techniques of FIGS. 57-59 are used to form cavities that extend down to the gate metal 110 of the gates 106 (i.e., to form the conductive vias 120), the intervening material of the hardmask 118 and the intervening material of the hardmask 116 may also be removed so that the gate metal 110 is exposed at the bottom of the cavities. Similarly, when the manufacturing techniques of FIGS. 57-59 are used to form cavities that extend down to the gate metal 112 of the gates 108 (i.e., to form the conductive vias 122), the intervening material of the hardmask 118 may also be removed so that the gate metal 112 is exposed at the bottom of the cavities.

Figure 60:
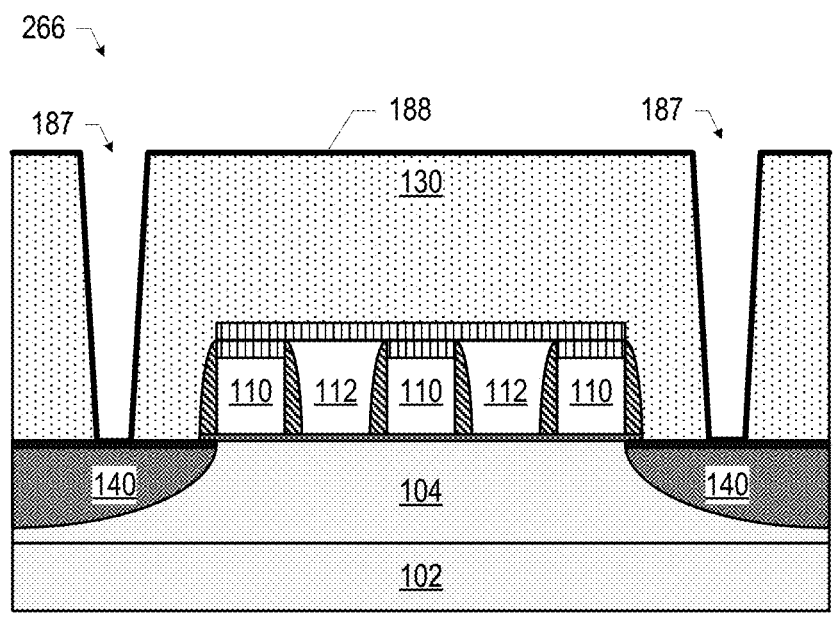

FIG. 60 is a cross-sectional view of an assembly 266 subsequent to providing an adhesion material 188 on the assembly 264 (FIG. 59). In particular, the adhesion material 188 may be provided on the exposed insulating material 130, as well as at the bottom of the cavities 187 (in FIG. 60, on the exposed interface material 141). The adhesion material 188 may be a conductive material that facilitates adhesion between the assembly 266 and the conductive material that will be subsequently provided (e.g., the conductive material 189 discussed below with reference to FIG. 61). In some embodiments, the adhesion material 188 may include a refractory metal or a refractory metal nitride, such as titanium, tantalum, titanium nitride, titanium zirconium nitride, ruthenium, doped ruthenium (e.g., ruthenium doped with phosphorous) or tantalum nitride. In some embodiments, the adhesion material 188 may include tantalum nitride/tantalum (TNT). In some embodiments, the adhesion material 188 may include titanium nitride, which may have any suitable thickness (e.g., between 10 Angstroms and 70 Angstroms). The adhesion material 188 may be provided using any suitable technique, such as ALD.

Figure 61:
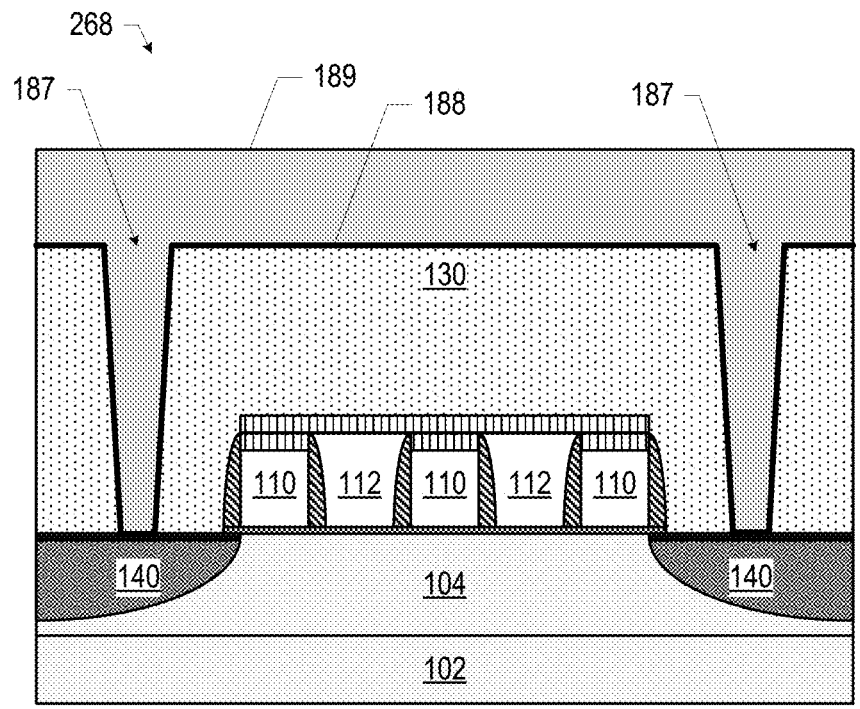

FIG. 61 is a cross-sectional view of an assembly 268 subsequent to providing a conductive material 189 on the assembly 266 (FIG. 60) such that the conductive material 189 fills the cavities 187. Any suitable technique may be used to provide the conductive material 189 on the assembly 266 (e.g., sputtering). The conductive material 189 may be in contact with the adhesion material 188. In some embodiments (e.g., as illustrated in FIG. 61), the conductive material 189 may extend beyond the cavities 187 over the insulating material 130. In some embodiments, the conductive material 189 may be copper. In some embodiments, the conductive material 189 may be tungsten (and may be deposited by CVD, for example). In some embodiments, the conductive material 189 may be a superconductor, such as aluminum, tin, titanium nitride, niobium titanium nitride, tantalum, niobium, and other niobium compounds (e.g., niobium tin and niobium germanium).

Figure 62:
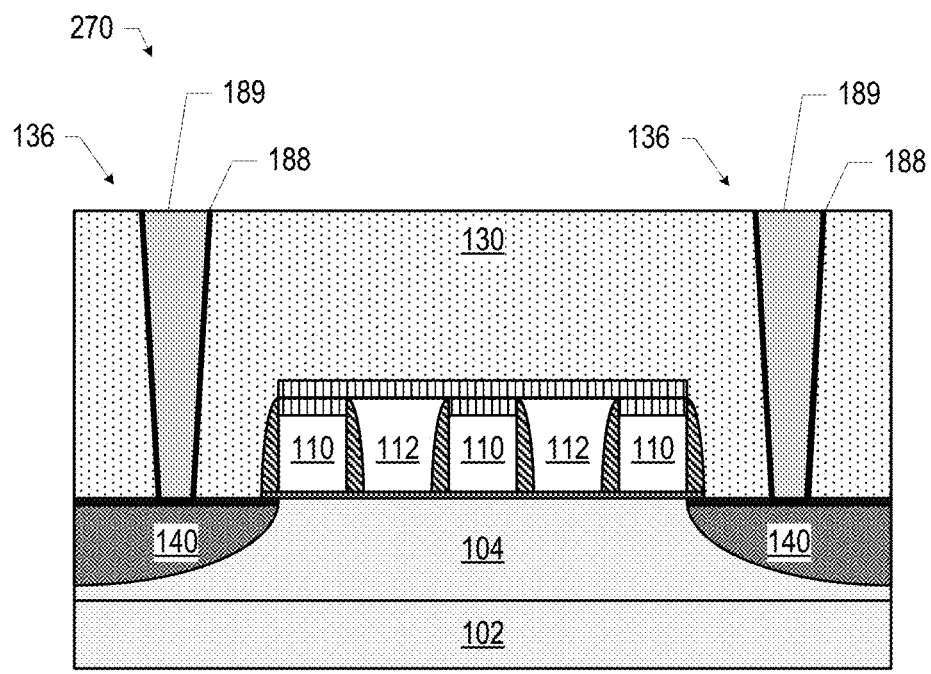

FIG. 62 is a cross-sectional view of an assembly 270 subsequent to planarizing the assembly 268 (FIG. 61) to remove the conductive material 189 that extends beyond the cavities 187. The remaining conductive material 189 in the cavities 187 (and the adhesion material 188 in the cavities 187) may provide the conductive vias 136. As noted above, analogous operations may be performed to manufacture the conductive vias 120 and 122 to the gates 106 and 108, respectively.

Figure 63:
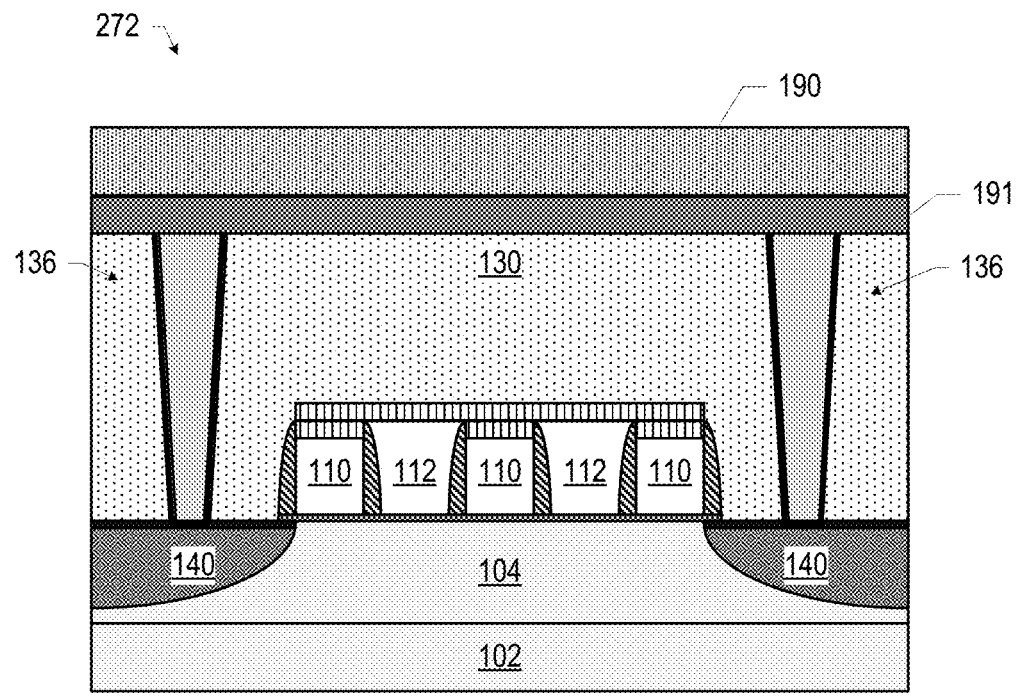

FIG. 63 is a cross-sectional view of an assembly 272 subsequent to depositing an etch stop material 191 and an insulating material 190 on the assembly 270 (FIG. 62). The etch stop material 191 may be disposed between the insulating material 190 and the assembly 270, as shown. The etch stop material 191 may include any suitable material, such as a DDM 500, a nitride, silicon carbide, silicon nitride, carbon-doped silicon nitride, or silicon oxycarbide. In some embodiments, the etch stop material 191 may be deposited using CVD. The etch stop material 191 may have any suitable thickness. In some embodiments, the etch stop material 191 may have a thickness that is less than 20 nanometers (e.g., between 8 nanometers and 12 nanometers). The insulating material 190 may be a dielectric material, such as any of the DDMs 500 disclosed herein. In other embodiments, the insulating material 190 may include silicon oxide, carbon-doped oxide, silicon oxynitride, and/or a polymer material. In some embodiments, the insulating material 190 may be deposited using CVD. The insulating material 190 may have any suitable thickness. In some embodiments, the insulating material 190 may have a thickness between 10 nanometers and 30 nanometers (e.g., between 10 nanometers and 20 nanometers).

Figure 64:
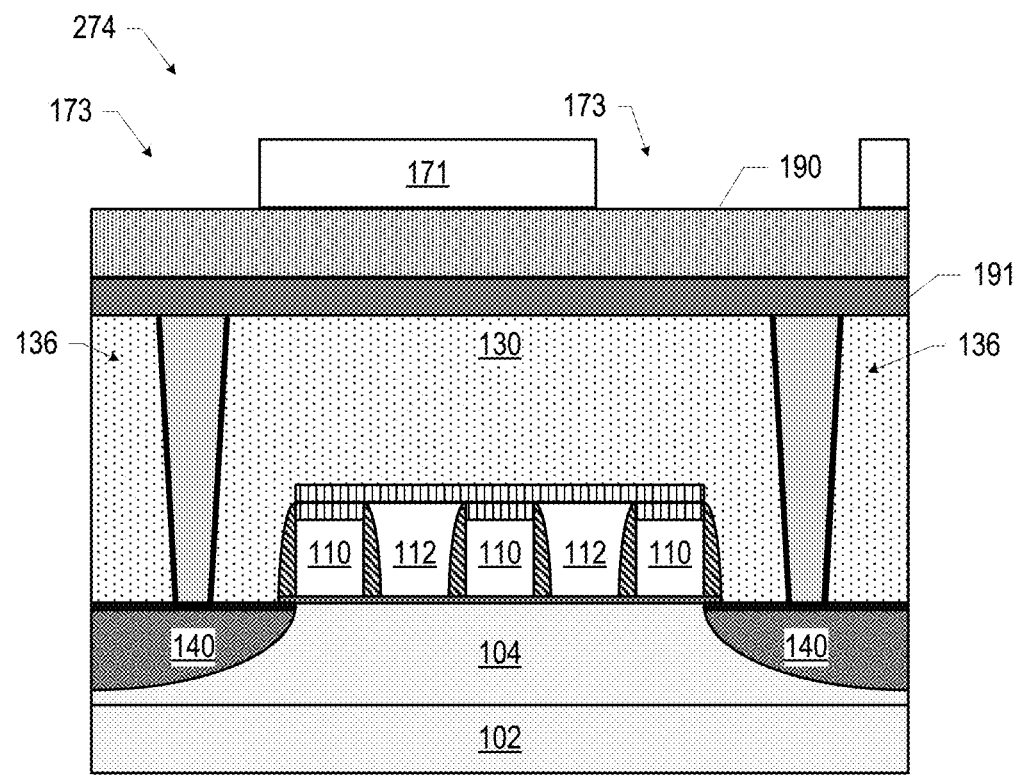

FIG. 64 is a cross-sectional view of an assembly 274 subsequent to providing a resist material 185 on the assembly 272 (FIG. 63) and patterning the resist material 171. The provision and patterning of the resist material 171 may take any suitable form (e.g., as discussed above with reference to FIGS. 57 and 58). In some embodiments, the resist material 171 may have the same material composition as the resist material 185; in other embodiments, the resist material 171 and the resist material 185 may have different material compositions. The patterned resist material 171 may include cavities 173 that extend down to and expose portions of the insulating material 190.

Figure 65:
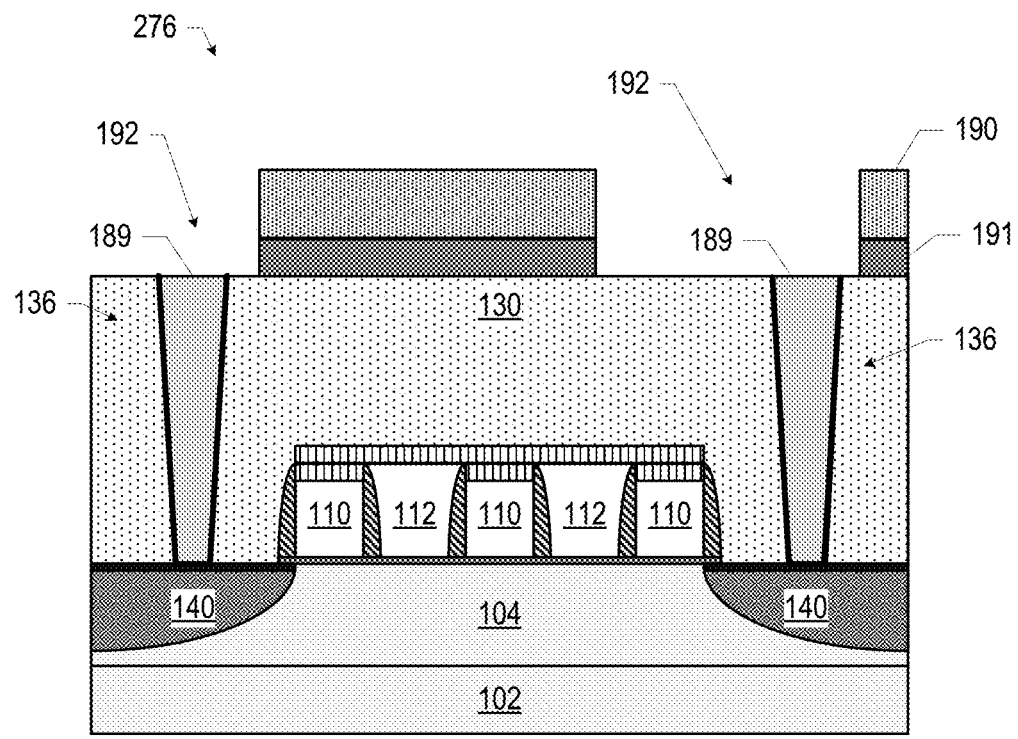

FIG. 65 is a cross-sectional view of an assembly 276 subsequent to etching the insulating material 190 and the etch stop material 191 in accordance with the pattern provided by the patterned resist material 171 of the assembly 274 (FIG. 64), and removing the remaining resist material 171. In particular, cavities 192 may be formed in the insulating material 190 and the etch stop material 191 at locations corresponding to the locations of the cavities 173 in the resist material 171. The cavities 173 (which may also be referred to as "trenches") may extend down to insulating material 130 and may expose the conductive material 189 of the conductive vias 136. In some embodiments, the formation of the cavities 192 may be a two-step process: first, the insulating material 190 may be etched (with the etch stop material 191 stopping that etch, and thus preventing over-etch into the insulating material 130), then the etch stop material 191 may be etched. In some embodiments, the cavities 192 may be tapered (e.g., as illustrated in FIG. 65).

Figure 66:
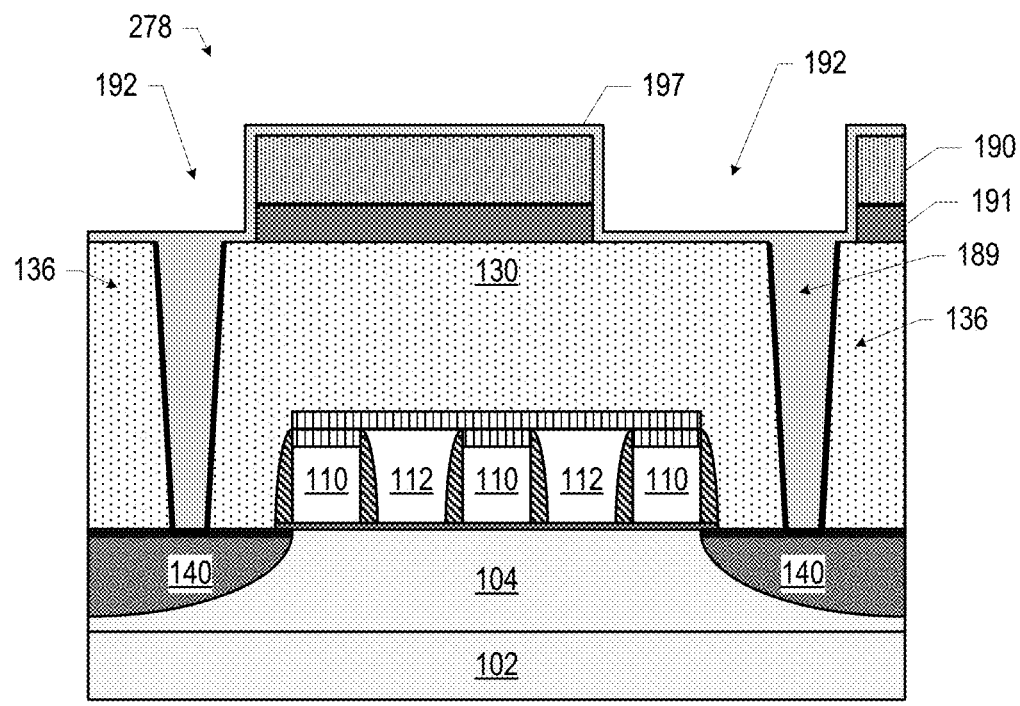

FIG. 66 is a cross-sectional view of an assembly 278 subsequent to providing a seed layer 197 of conductive material on the assembly 276 (FIG. 65) such that the seed layer 197 extends over the walls and bottoms of the cavities 192 (as well as over the exposed top surfaces of the patterned insulating material 190). In particular, the seed layer 197 may be in conductive contact with the conductive material 189 of the conductive vias 136. The seed layer 197 may be formed of a same material as the conductive material 189, and as discussed below with reference to FIG. 67, may facilitate electroplating of additional such material. In some embodiments, the seed layer 197 may be formed of ruthenium, cobalt, or copper. In some embodiments, a liner material (not shown) may be provided on the assembly 278 before the seed layer 197 is provided. The liner material may serve one or more functions, including improving adhesion (e.g., as discussed above with reference to the adhesion material 188), providing a barrier against metal diffusion (e.g., between conductive lines/vias and proximate insulating material, which may include a DDM 500), and reducing electromigration between conductive lines and vias. In some embodiments, the liner material may take any of the forms discussed above with reference to the adhesion material 188 (e.g., to reduce electromigration and/or provide a diffusion barrier). In some embodiments, the liner material may include copper doped with aluminum, or copper doped with manganese (e.g., to reduce electromigration). The liner material may be provided by ALD, CVD, or sputtering, for example. The liner material may have any suitable thickness (e.g., between 2 Angstroms and 70 Angstroms).

Figure 67:
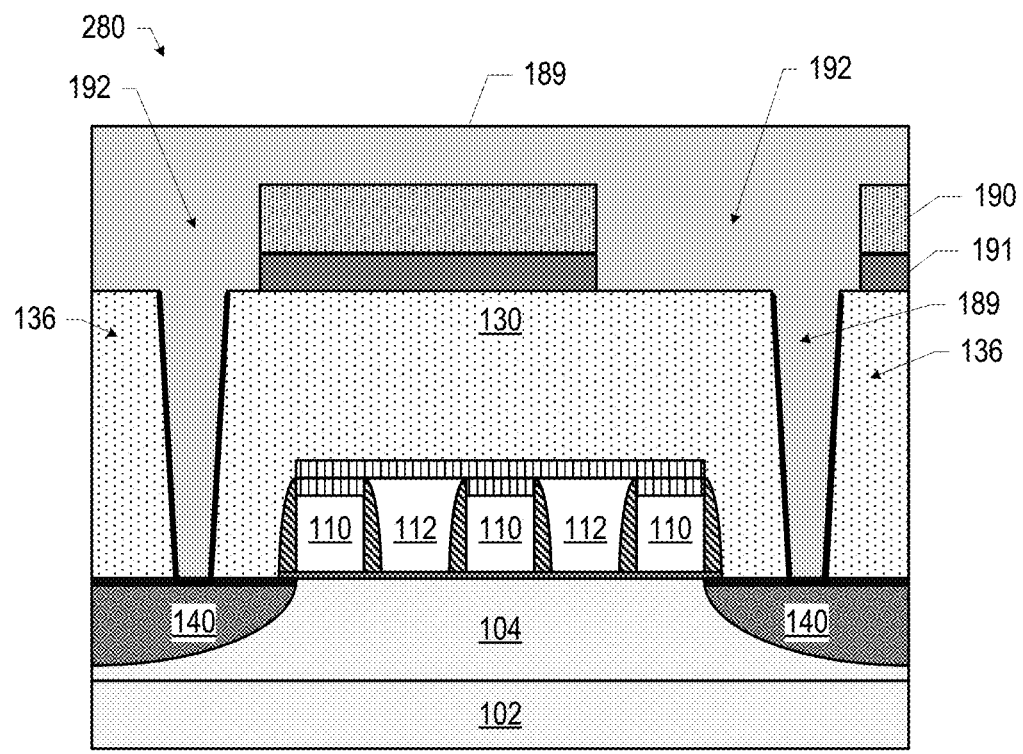

FIG. 67 is a cross-sectional view of an assembly 280 subsequent to providing additional conductive material 189 on the seed layer 197 of the assembly 278 (FIG. 66). In particular, the additional conductive material 189 may fill the cavities 192, and in some embodiments, may extend beyond the cavities 192 over the adjacent insulating material 190 (as shown). In some embodiments, the additional conductive material 189 may be electroplated onto the assembly 278 to form the assembly 280. The additional conductive material 189 may take the form of any of the embodiments of the conductive material 189 discussed herein (e.g., a superconducting material). In some embodiments, the additional conductive material 189 may not be provided by electroplating, but may instead be provide by electroless deposition (e.g., when the additional conductive material 189 includes copper or tin), ALD (e.g., when the additional conductive material includes titanium nitride), or sputtering, for example.

Figure 68:
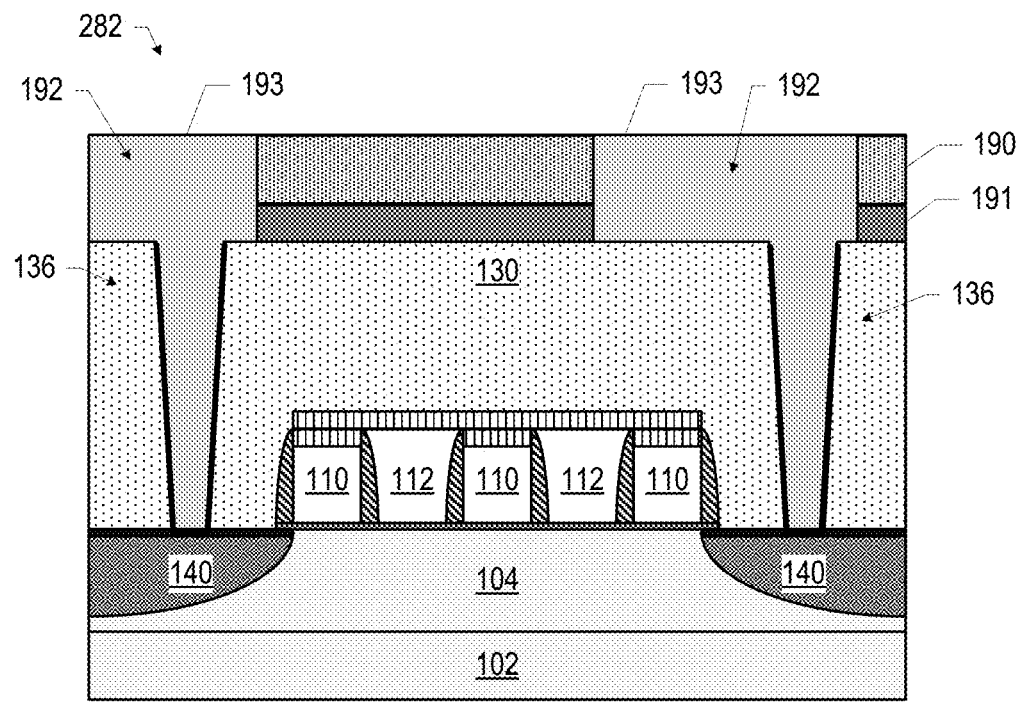

FIG. 68 is a cross-sectional view of an assembly 282 subsequent to planarizing the assembly 280 (FIG. 67) to remove the conductive material 189 that extended beyond the cavities 192 of the assembly 280. The resulting conductive material 189 that fills the cavities 192 may provide conductive lines 193 in conductive contact with the conductive vias 136. The operations discussed above with reference to FIGS. 63-68 may represent a single Damascene process for forming the conductive lines 193; any suitable embodiments of such a process may be used to form interconnects in the quantum dot devices 100 disclosed herein. In some embodiments, the conductive lines 193 of the assembly 282 may extend into and out of the plane of the drawing, providing conductive pathways to route electrical signals to and/or from the doped regions 140. Analogous conductive lines may be formed to provide conductive contact to the conductive vias 120 and 122 for the gates 106 and 108, respectively.

Figure 69:
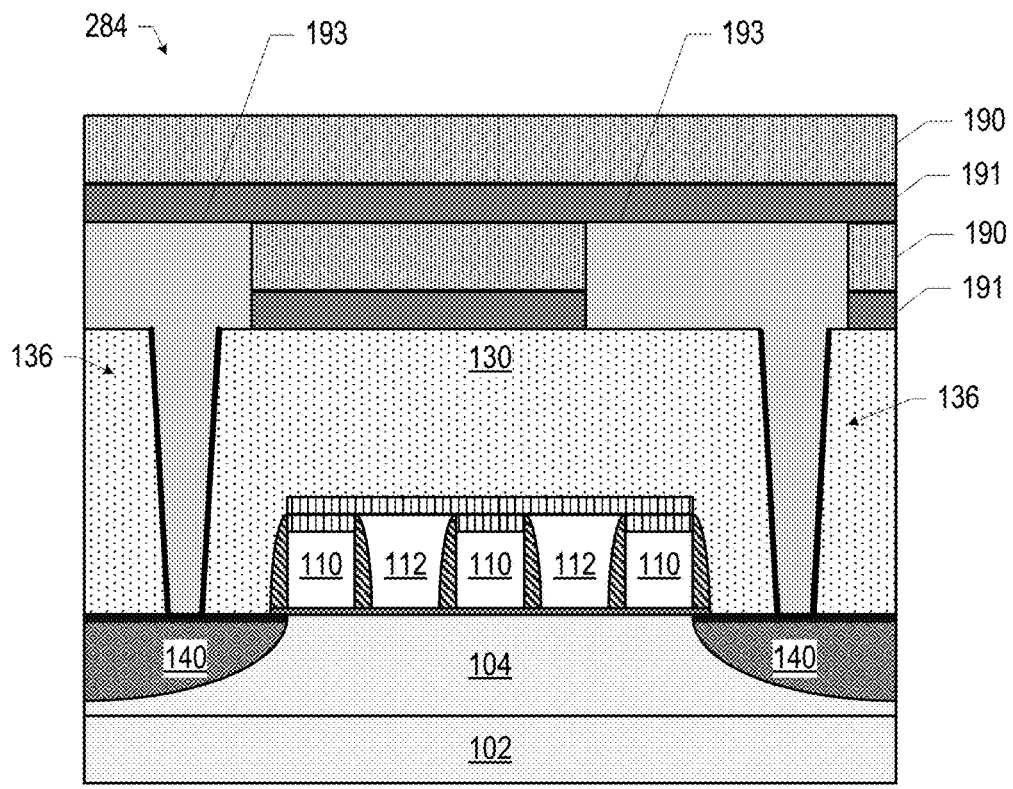

FIG. 69 is a cross-sectional view of an assembly 284 subsequent to depositing additional etch stop material 191 and additional insulating material 190 on the assembly 282 (FIG. 68). The additional etch stop material 191 may be provided between the assembly 282 and the additional insulating material 190, as shown, and may be provided in accordance with any of the embodiments discussed above with reference to FIG. 63.

Figure 70:
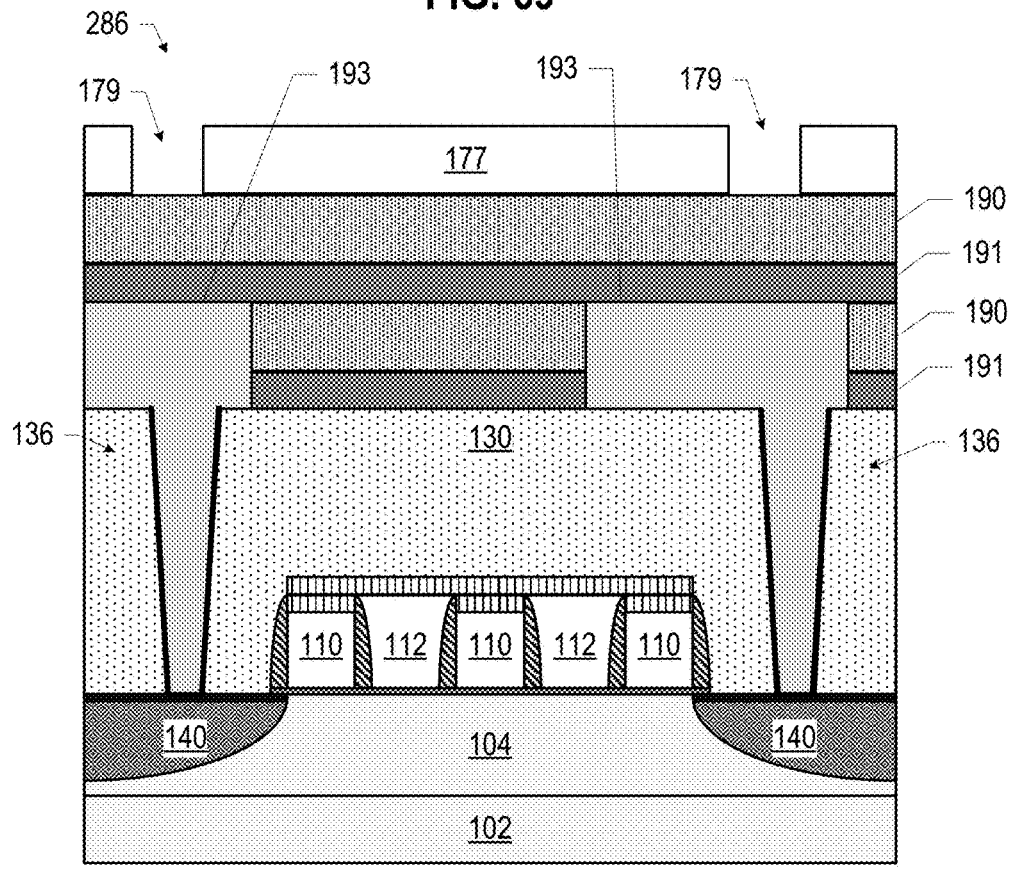

FIG. 70 is a cross-sectional view of an assembly 286 subsequent to providing a resist material 177 on the assembly 284 (FIG. 69) and patterning the resist material 177. The provision and patterning of the resist material 177 may take any suitable form (e.g., as discussed above with reference to FIGS. 57 and 58). In some embodiments, the resist material 177 may have the same material composition as the resist material 171; in other embodiments, the resist material 177 and the resist material 171 may have different material compositions. The patterned resist material 177 may include cavities 179 that extend down to and expose portions of the additional insulating material 190.

Figure 71:
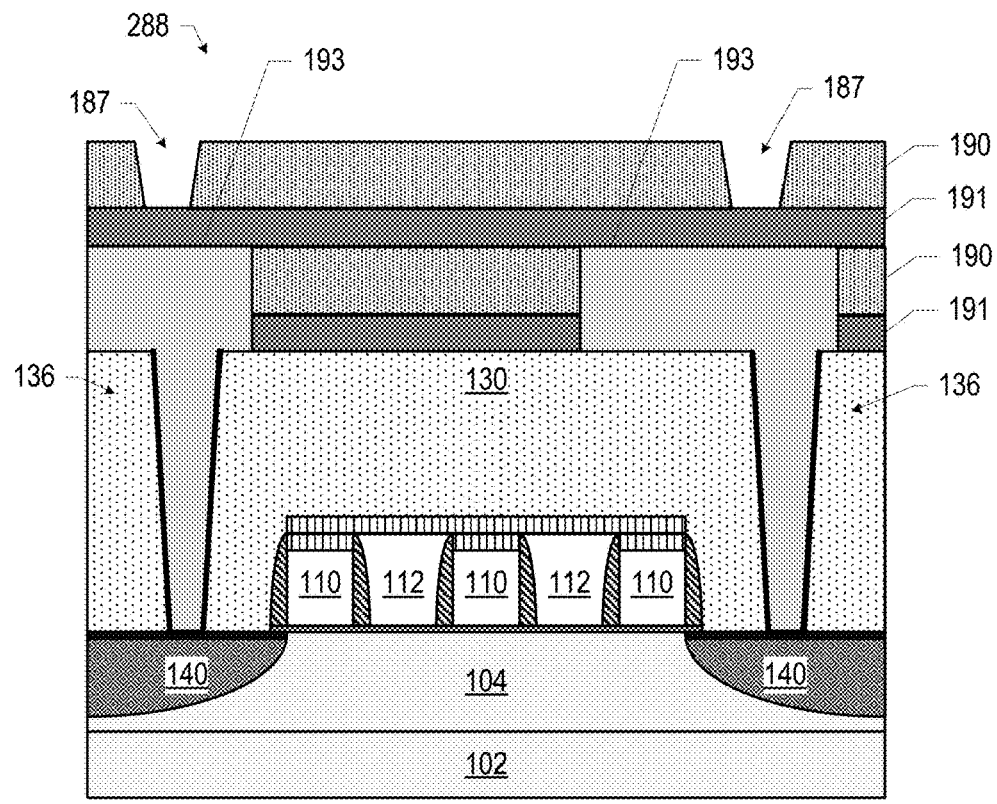

FIG. 71 is a cross-sectional view of an assembly 288 subsequent to etching the additional insulating material 190 in accordance with the pattern provided by the patterned resist material 177 of the assembly 286 (FIG. 70), and removing the remaining resist material 177. In particular, cavities 187 may be formed in the additional insulating material 190 at locations corresponding to the locations of the cavities 179 in the resist material 177. The cavities 187 may extend down to the additional etch stop material 191 (which may serve as an etch stop for the formation of the cavities 187). In some embodiments, the cavities 187 may be tapered, as shown.

Figure 72:
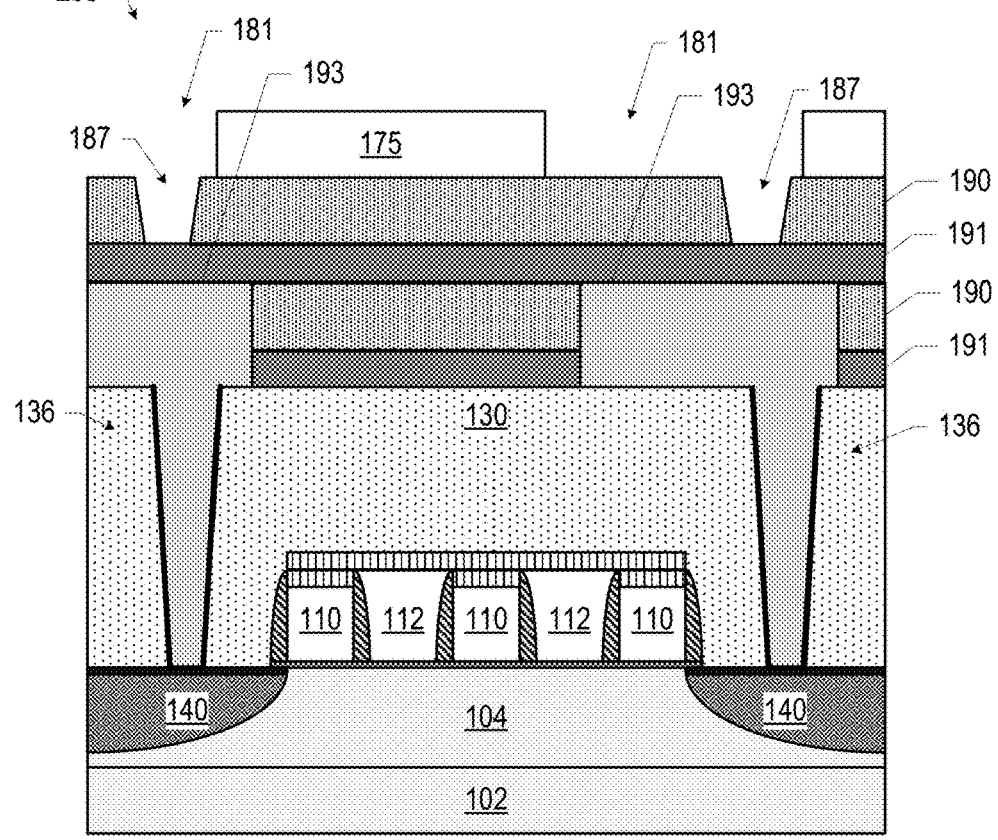

FIG. 72 is a cross-sectional view of an assembly 290 subsequent to providing a resist material 175 on the assembly 288 (FIG. 71) and patterning the resist material 175. The provision and patterning of the resist material 175 may take any suitable form (e.g., as discussed above with reference to FIGS. 57 and 58). In some embodiments, the resist material 175 may have the same material composition as the resist material 177; in other embodiments, the resist material 175 and the resist material 177 may have different material compositions. The patterned resist material 175 may include cavities 181 that extend down to and expose portions of the additional insulating material 190, and also expose the cavities 187 in the additional insulating material 190.

Figure 73:
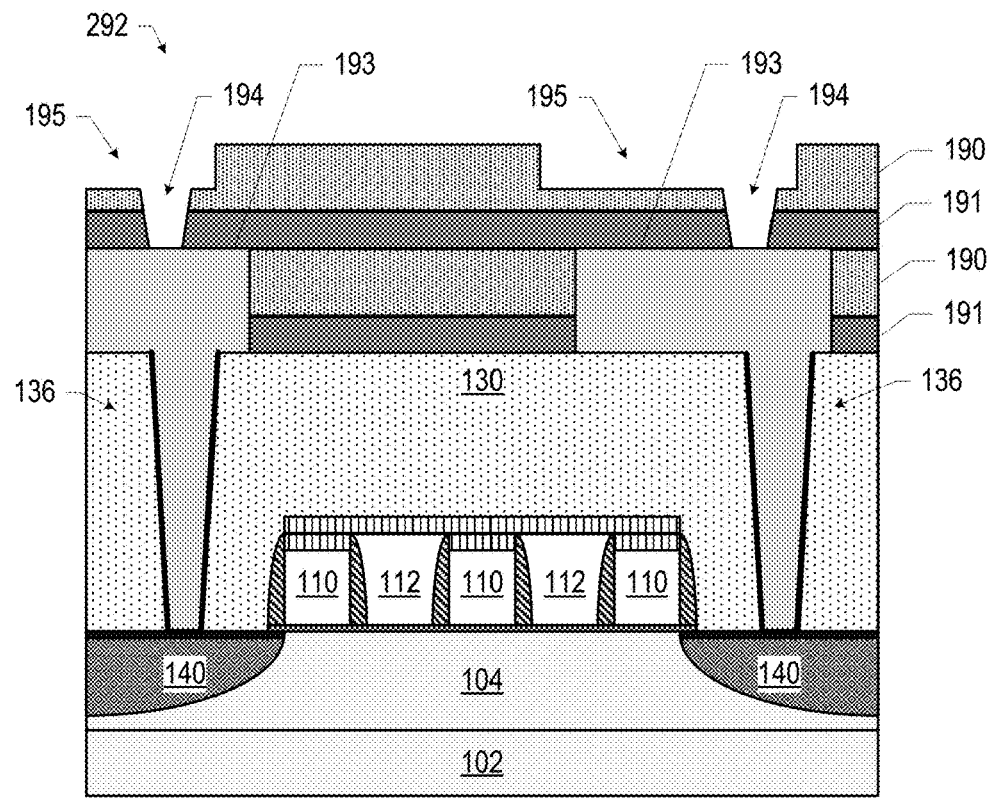

FIG. 73 is a cross-sectional view of an assembly 292 subsequent to etching the additional insulating material 190 and the additional etch stop material 191 in accordance with the pattern provided by the patterned resist material 175 of the assembly 290 (FIG. 72), and removing the remaining resist material 175. In particular, a timed etch may be used to remove some of the additional oxide material 191 that was not protected by the resist material 175, leaving cavities 195 (which may also be referred to as "trenches"). After the timed etch, the additional etch stop material 191 at the bottom of the cavities 187 may be removed to form cavities 194 (e.g., as part of a two-step process, as discussed above with reference to FIG. 65). The cavities 195 may extend over the cavities 194, as shown.

Figure 74:
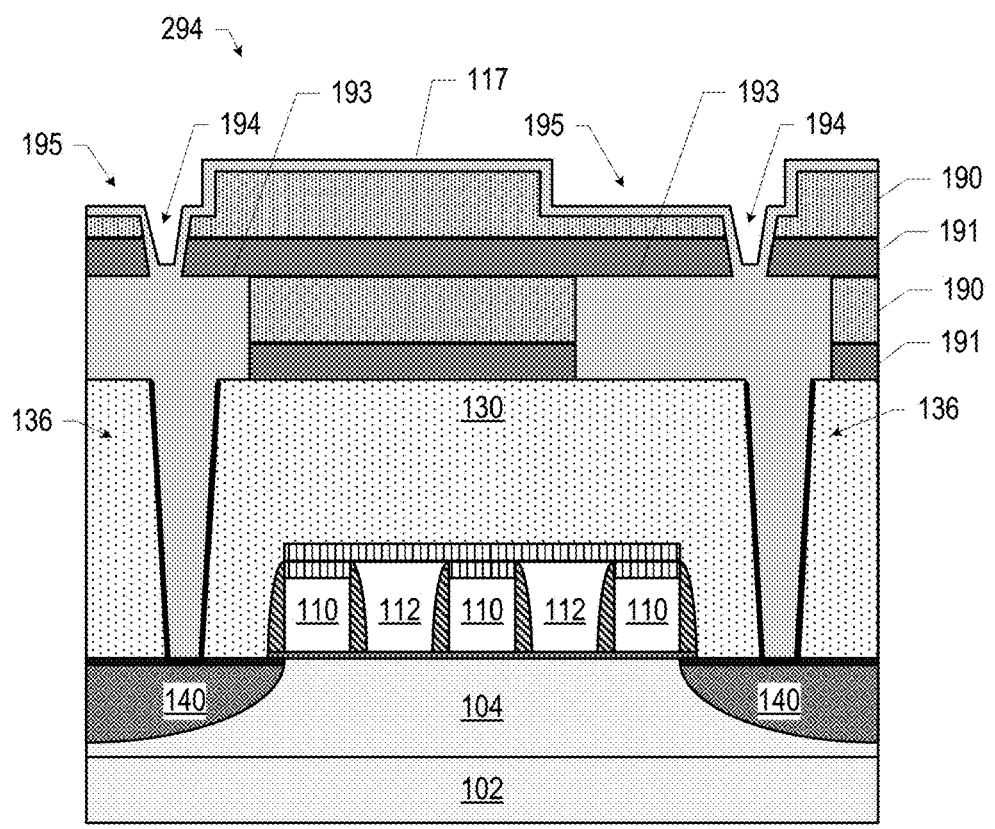

FIG. 74 is a cross-sectional view of an assembly 294 subsequent to providing a seed layer 117 of conductive material on the assembly 292 (FIG. 73) such that the seed layer 117 extends over the walls and bottoms of the cavities 194 and 195 (as well as over the exposed top surfaces of the additional insulating material 190). In particular, the seed layer 117 may be in conductive contact with the conductive lines 193. The seed layer 117 may take the form of any of the embodiments of the seed layer 197, discussed above.

Figure 75:
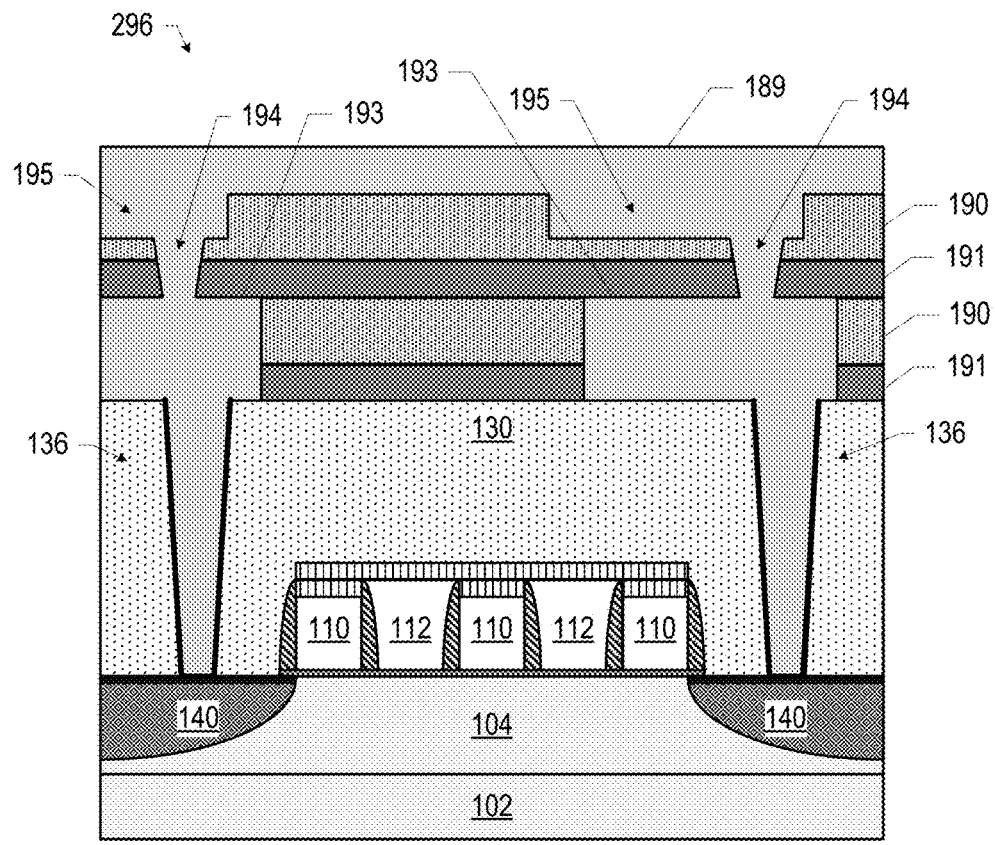

FIG. 75 is a cross-sectional view of an assembly 296 subsequent to providing additional conductive material 189 on the seed layer 117 of the assembly 294 (FIG. 74). In particular, the additional conductive material 189 may fill the cavities 194 and 195, and in some embodiments, may extend beyond the cavities 194 and 195 over the adjacent insulating material 190 (as shown). In some embodiments, the additional conductive material 189 may be electroplated onto the assembly 294 to form the assembly 296.

Figure 76:
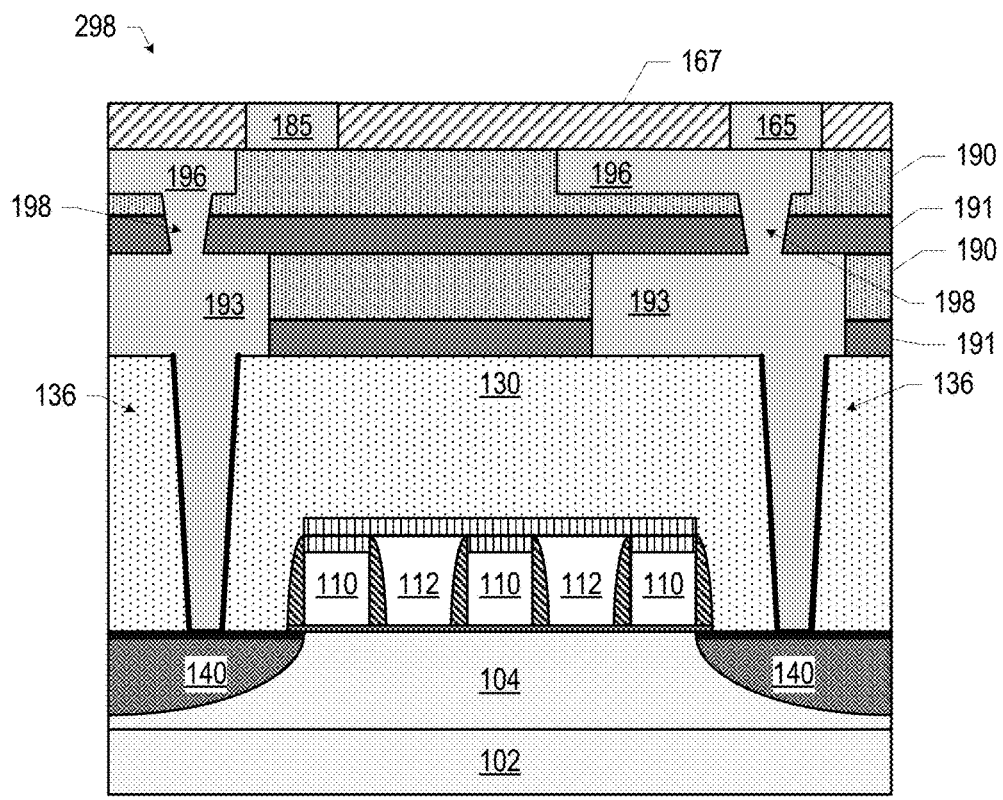

FIG. 76 is a cross-sectional view of an assembly 298 subsequent to planarizing the assembly 296 (FIG. 75) to remove the conductive material 189 that extended beyond the cavities 194 and 195 of the assembly 296, forming conductive contacts 165 on the planarized surface, and providing a solder resist material 167 around the conductive contacts 165 on the planarized surface. The resulting conductive material 189 that fills the cavities 195 may provide conductive vias 198 in conductive contact with the conductive lines 193, and the conductive material 189 that fills the cavities 194 may provide conductive lines 196 in conductive contact with the conductive vias 198. The conductive contacts 165 may be in conductive contact with the conductive lines 196. In some embodiments, the conductive lines 196 of the assembly 298 may extend into and out of the plane of the drawing, providing conductive pathways to route electrical signals to and/or from the doped regions 140. Before providing the conductive contacts 165 and the solder resist material 167, additional conductive vias and lines may be formed on the conductive lines 196 by repeating the operations discussed above with reference to FIGS. 69-76 to form any desired interconnect structures for electrical contact with the doped regions 140 (and, analogously, to form any desired interconnect structures for electrical contact with the gates 106 and 108). The operations discussed above with reference to FIGS. 69-76 may represent a dual Damascene process for forming conductive lines and vias; any suitable embodiments of such a process may be used to form interconnects in the quantum dot devices 100 disclosed herein.

During operation of the quantum dot device 100, electrical signals (such as power and/or input/output (I/O) signals) may be routed to and/or from the gates 106/108 and/or the doped regions 140 of the quantum dot device 100 through the interconnects provided by the conductive vias 120/122/136 and additional conductive vias and/or lines. The combination of the interconnect structures and the proximate insulating material (e.g., the insulating material 130, the insulating material 190, and the etch stop material 191, any one or more of which may advantageously include any of the DDMs 500 disclosed herein) may provide an interlayer dielectric (ILD) stack of the quantum dot device 100. As noted above, interconnect structures may be arranged within the quantum dot device 100 to route electrical signals according to a wide variety of designs (in particular, the arrangement is not limited to the particular configuration of interconnect structures depicted in FIG. 76 or any of the other accompanying figures, and may include more or fewer interconnect structures).

The conductive vias 120/122/136 may be referred to as part of the "device layer" of the quantum dot device 100, which may also include the gates 106/108 and the doped regions 140. The conductive lines 193 may be referred to as a Metal 1 or "M1" interconnect layer, and may couple the conductive vias 120/122/136 to other interconnect structures. The conductive vias 198 and the conductive lines 196 may be referred to as a Metal 2 or "M2" interconnect layer, and may be formed directly on the M1 interconnect layer. Although the different conductive vias and lines in FIG. 76 (and other figures herein) are not delineated with lines (and are instead illustrated as a continuous structure), conductive vias and lines that are in conductive contact may or may not be structurally and/or materially contiguous.

The solder resist material 167 (e.g., a polyimide or similar material) may be disposed around the conductive contacts 165, and in some embodiments, may extend onto the conductive contacts 165 (not shown). The conductive contacts 165 may provide the contacts to couple other components (e.g., a package substrate or other component) to the interconnect structures in the quantum dot device 100, and may be formed of any suitable conductive material (e.g., a superconducting material). For example, solder bonds may be formed on the one or more conductive contacts 165 to mechanically and/or electrically couple a chip including the quantum dot device 100 with another component (e.g., a circuit board). The conductive contacts 165 illustrated in FIG. 76 take the form of bond pads, but other first level interconnect structures may be used (e.g., posts) to route electrical signals to/from the quantum dot device 100.

The manufacturing techniques illustrated in FIGS. 57-76 are illustrative examples of techniques that may be used to form some embodiments of the quantum dot devices 100 disclosed herein, but other techniques may be used instead of or in combination with the techniques discussed above. For example, FIGS. 77-80 illustrate various alternative manufacturing operations using subtractive techniques for forming various interconnect structures in a quantum dot device 100. In the example depicted in FIGS. 77-80, the conductive lines 193 (discussed above with reference to FIG. 68) may be formed using a subtractive process (e.g., instead of the additive process illustrated by FIGS. 63-68). In some embodiments, the operations discussed below with reference to FIGS. 77-80 may replace the operations discussed above with reference to FIGS. 63-68.

Figure 77:
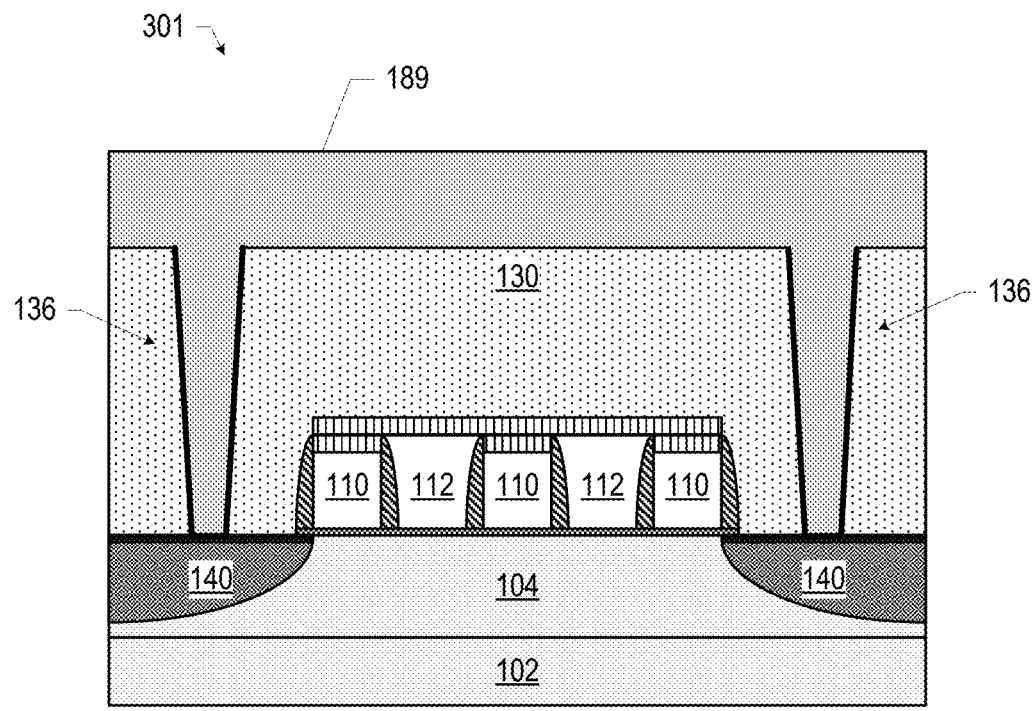
FIGS. 77-80 illustrate various alternative example stages in the formation of interconnects in a quantum dot device, in accordance with various embodiments.

FIG. 77 is a cross-sectional view of an assembly 301 subsequent to providing a conductive material 189 on the assembly 270 (FIG. 62). The conductive material 189 may be provided using any suitable technique (e.g., sputtering), and may be in conductive contact with the conductive vias 136, as shown. The conductive material 189 may take the form of any of the conductive materials 189 disclosed herein (e.g., a superconducting material).

Figure 78:
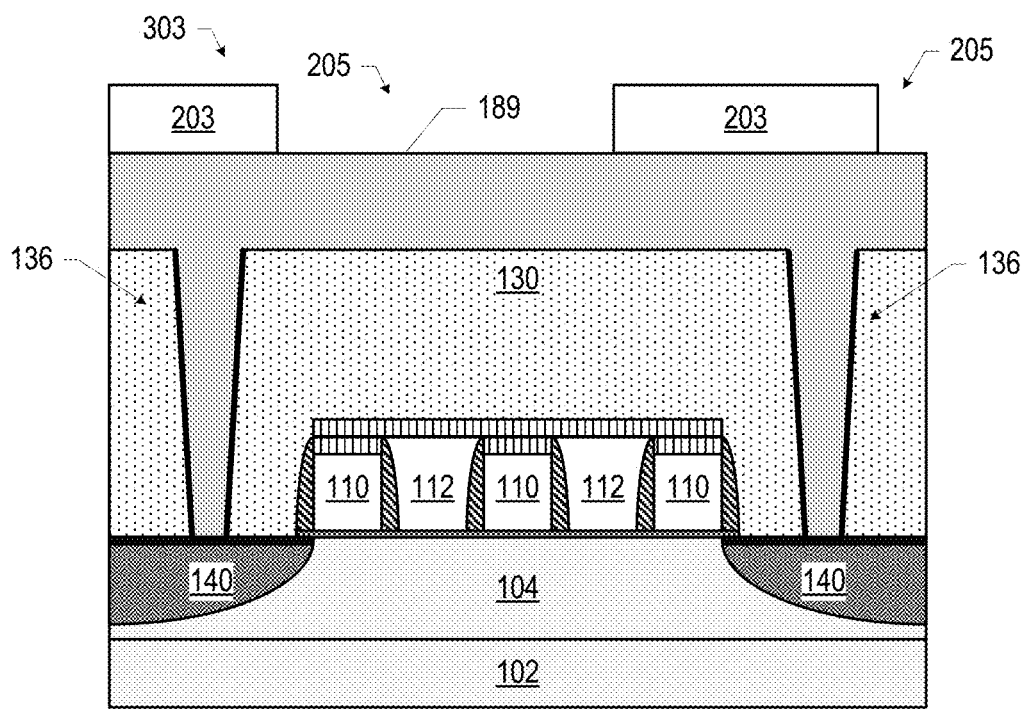

FIG. 78 is a cross-sectional view of an assembly 303 subsequent to providing a resist material 203 on the assembly 301 (FIG. 77) and patterning the resist material 203. The provision and patterning of the resist material 203 may take any suitable form (e.g., as discussed above with reference to FIGS. 57 and 58). The resist material 203 may be any resist material suitable for etching the conductive material 189, as discussed below. The patterned resist material 203 may include cavities 205 that extend down to and expose portions of the conductive material 189.

Figure 79:
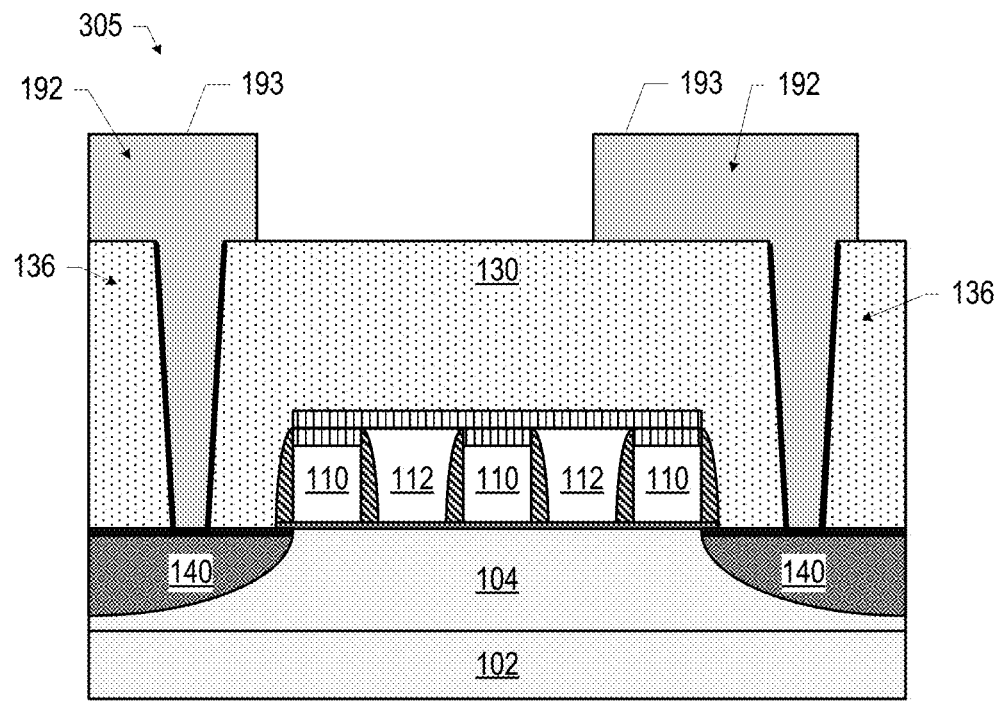

FIG. 79 is a cross-sectional view of an assembly 305 subsequent to etching the exposed conductive material 189, in accordance with the pattern provided by the patterned resist material 203 of the assembly 303 (FIG. 78), and removing the remaining resist material 203. The remaining patterned conductive material 189 (in conductive contact with the conductive vias 136) may provide the conductive lines 193.

Figure 80:
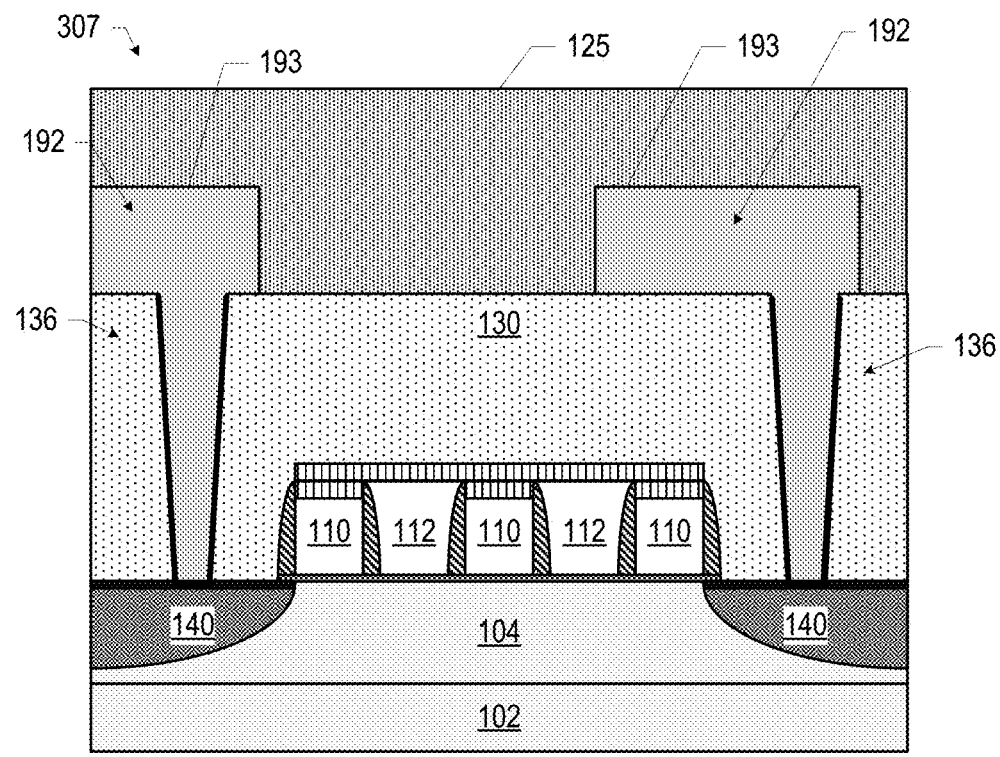

FIG. 80 is a cross-sectional view of an assembly 307 subsequent to providing an insulating material 125 (e.g., a dielectric material, such as a DDM 500) around the conductive lines 193 of the assembly 305 of FIG. 79. The insulating material 125 may be an insulating material (e.g., any of the materials discussed above with reference to the insulating material 190, such as a DDM 500) or any other suitable material, and may be deposited using any suitable technique. In some embodiments, the insulating material 125 may be planarized subsequent to deposition so as to provide a flat surface on which subsequent layers of conductive vias and lines may be built (e.g., using any of the techniques discussed herein).

Although particular patterning techniques are discussed herein, any suitable patterning techniques and materials may be used in the manufacture of the quantum dot devices 100 disclosed herein. For example, self-aligned double patterning techniques, hardmask lithography techniques, or antireflective coating (ARC) techniques may be used. In another example, air gap dielectrics may be included in any of the insulating materials, and air gap formation techniques may be incorporated into the process of manufacturing a quantum dot device 100, as suitable.

Figures 81, 82:
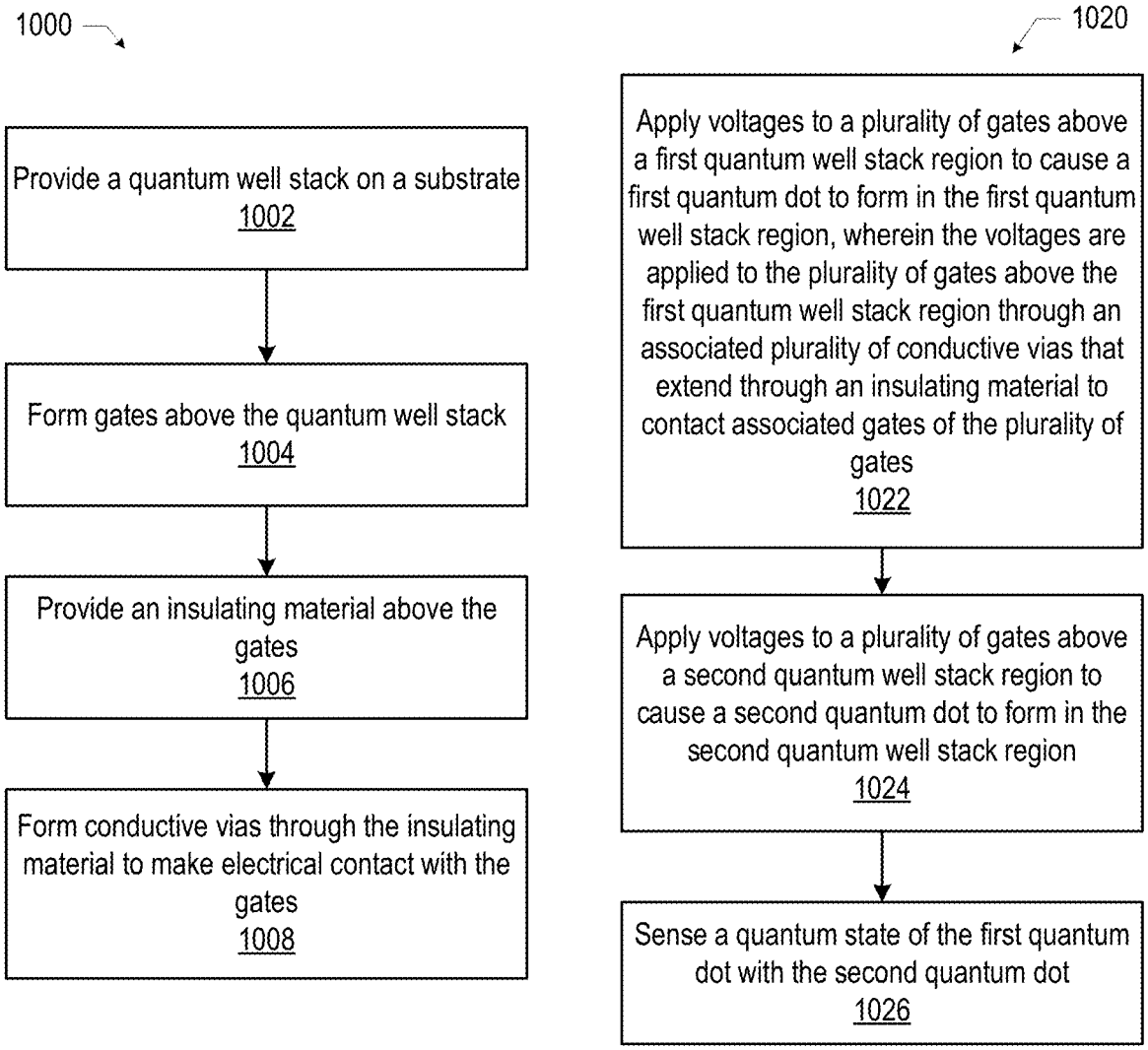

As noted above, any suitable techniques may be used to manufacture the quantum dot devices 100 disclosed herein. FIG. 81 is a flow diagram of an illustrative method 1000 of manufacturing a quantum dot device, in accordance with various embodiments. Although the operations discussed below with reference to the method 1000 are illustrated in a particular order and depicted once each, these operations may be repeated or performed in a different order (e.g., in parallel), as suitable. Additionally, various operations may be omitted, as suitable. Various operations of the method 1000 may be illustrated with reference to one or more of the embodiments discussed above, but the method 1000 may be used to manufacture any suitable quantum dot device (including any suitable ones of the embodiments disclosed herein).

At 1002, a quantum well stack may be provided on a substrate. For example, a quantum well stack 146 may be provided on a substrate 144 (e.g., as discussed above with reference to FIGS. 13-14 and 35-37).

At 1004, gates may be formed above the quantum well stack. For example, gates 106 and/or 108 may be formed on the fins 104 (e.g., as discussed above with reference to FIGS. 20-29 and 49).

At 1006, an insulating material may be provided above the gates. For example, hardmasks 116 and/or 118 may be provided on the gate metal 110 and/or 112 of the gates 106 and/or 108, respectively, and an insulating material 130 may be disposed on the gates 106 and/or 108 (e.g., as discussed above with reference to FIGS. 20-29 and 33).

At 1008, conductive vias may be formed through the insulating material to make electrical contact with the gates. For example, conductive vias 120 and/or 122 may be formed through the insulating material 130, the hardmask 116, and/or the hardmask 118 (e.g., as discussed above with reference to FIGS. 34 and 57-80).

A number of techniques are disclosed herein for operating a quantum dot device 100. FIGS. 82-83 are flow diagrams of particular illustrative methods 1020 and 1040, respectively, of operating a quantum dot device, in accordance with various embodiments. Although the operations discussed below with reference to the methods 1020 and 1040 are illustrated in a particular order and depicted once each, these operations may be repeated or performed in a different order (e.g., in parallel), as suitable. Additionally, various operations may be omitted, as suitable. Various operations of the methods 1020 and 1040 may be illustrated with reference to one or more of the embodiments discussed above, but the methods 1020 and 1040 may be used to operate any suitable quantum dot device (including any suitable ones of the embodiments disclosed herein).

Turning to the method 1020 of FIG. 82, at 1022, voltages may be applied to a plurality of gates above a first quantum well stack region to cause a first quantum dot to form in the first quantum well stack region. The voltages may be applied to the plurality of gates above the first quantum well stack region through an associated plurality of conductive vias that extend through an insulating material to contact associated gates of the plurality of gates. For example, one or more voltages may be applied to the gates 106/108 on a fin 104-1 through the conductive vias 120/122 to cause at least one quantum dot 142 to form in the fin 104-1.

At 1024, voltages may be applied to a plurality of gates above a second quantum well stack region to cause a second quantum dot to form in the second quantum well stack region. For example, one or more voltages may be applied to the gates 106/108 on a fin 104-2 (e.g., through the conductive vias 120/122) to cause at least one quantum dot 142 to form in the fin 104-2.

At 1026, a quantum state of the first quantum dot may be sensed with the second quantum dot. For example, a quantum dot 142 in the fin 104-2 (the "read" fin) may sense the quantum state of a quantum dot 142 in the fin 104-1 (the "active" fin).

Turning to the method 1040 of FIG. 83, at 1042, a voltage may be applied to a first gate disposed above a quantum well stack region to cause a first quantum dot to form in a first quantum well in the quantum well stack region under the first gate. The voltage may be applied to the first gate through a conductive via in conductive contact with the first gate. For example, a voltage may be applied to the gate 108-1 disposed on a fin 104 (through a conductive via 122) to cause a first quantum dot 142 to form in the quantum well layer 152 in the fin 104 under the gate 108-1.

At 1044, a voltage may be applied to a second gate disposed above the quantum well stack region to cause a second quantum dot to form in a second quantum well in the quantum well stack region under the second gate. For example, a voltage may be applied to the gate 108-2 disposed on the fin 104 (e.g., through a conductive via 122) to cause a second quantum dot 142 to form in the quantum well layer 152 in the fin 104 under the gate 108-2.

At 1046, a voltage may be applied to a third gate disposed above the quantum well stack region to (1) cause a third quantum dot to form in a third quantum well in the quantum well stack region under the third gate or (2) provide a potential barrier between the first quantum well and the second quantum well. For example, a voltage may be applied to the gate 106-2 (e.g., through a conductive via 120) to (1) cause a third quantum dot 142 to form in the quantum well layer 152 in the fin 104 (e.g., when the gate 106-2 acts as a "plunger" gate) or (2) provide a potential barrier between the first quantum well (under the gate 108-1) and the second quantum well (under the gate 108-2) (e.g., when the gate 106-2 acts as a "barrier" gate).

As noted above, any suitable ones of the DDMs 500 may be included in superconducting qubit-type circuitry. FIGS. 84-85 illustrate example embodiments in which a DDM 500 is included in superconducting qubit-type circuitry. In particular, a DDM 500 may be used to isolate any of the conductive elements of superconducting qubit-type circuitry from each other (e.g., isolating interconnects). The operation of superconducting qubit-type quantum devices may be based on the Josephson effect, a macroscopic quantum phenomenon in which a supercurrent (a current that, due to zero electrical resistance, flows for indefinitely long without any voltage applied) flows across a device known as a Josephson junction. Examples of superconducting qubit-type quantum devices may include charge qubits, flux qubits, and phase qubits. Transmons, a type of charge qubit with the name being an abbreviation of "transmission line shunted plasma oscillation qubits," may exhibit reduced sensitivity to charge noise, and thus may be particularly advantageous. Transmon-type quantum devices may include inductors, capacitors, and at least one nonlinear element (e.g., a Josephson junction) to achieve an effective two-level quantum state system.

Josephson junctions may provide the central circuit elements of a superconducting qubit-type quantum device. A Josephson junction may include two superconductors connected by a weak link. For example, a Josephson junction may be implemented as a thin layer of an insulating material, referred to as a barrier or a tunnel barrier and serving as the "weak link" of the junction, sandwiched between two layers of superconductor. Josephson junctions may act as superconducting tunnel junctions. Cooper pairs may tunnel across the barrier from one superconducting layer to the other. The electrical characteristics of this tunneling are governed by the Josephson relations. Because the inductance of a Josephson junction is nonlinear, when used in an inductor-capacitor circuit (which may be referred to as an LC circuit) in a transmon-type quantum device, the resulting circuit has uneven spacing between its energy states. In other classes of superconducting qubit-type quantum devices, Josephson junctions combined with other circuit elements may similarly provide the nonlinearity necessary for forming an effective two-level quantum state to act as a qubit.

FIG. 84 is a block diagram of an example superconducting quantum circuit 300. As shown in FIG. 84, a superconducting quantum circuit 300 includes two or more qubit elements, 302-1 and 302-2. Qubit elements 302-1 and 302-2 may be identical and thus the discussion of FIG. 84 may refer generally to the "qubit elements 302"; the same applies to Josephson junctions 304-1 and 304-2, which may generally be referred to as "Josephson junctions 304," and to circuit elements 306-1 and 306-2, which may generally be referred to as "circuit elements 306." As shown in FIG. 84, each of the superconducting qubit elements 302 may include one or more Josephson junctions 304 connected to one or more other circuit elements 306, which, in combination with the Josephson junction(s) 304, may form a nonlinear circuit providing a unique two-level quantum state for the qubit. The circuit elements 306 could be, for example, capacitors in transmons or superconducting loops in flux qubits.

A superconducting quantum circuit 300 may include circuitry 308 for providing external control of qubit elements 302 and circuitry 310 for providing internal control of qubit elements 302. In this context, "external control" refers to controlling the qubit elements 302 from outside of the die that includes the qubit elements 302, including control by a user of a quantum computer, while "internal control" refers to controlling the qubit elements 302 within the die that includes the qubit elements 302. For example, if qubit elements 302 are transmon qubit elements, external control may be implemented by means of flux bias lines (also known as "flux lines" and "flux coil lines") and by means of readout and drive lines (also known as "microwave lines" since qubit elements are typically designed to operate with microwave signals), described in greater detail below. On the other hand, internal control lines for such qubit elements may be implemented by means of resonators (e.g., coupling and readout resonators, also described in greater detail below).

FIG. 85 illustrates an example of a physical layout 311 of a superconducting quantum circuit where qubit elements are implemented as transmons. Like FIG. 84, FIG. 85 illustrates two qubit elements 302. In addition, FIG. 85 illustrates flux bias lines 312, microwave lines 314, a coupling resonator 316, a readout resonator 318, and conductive contacts 320 and 322. The flux bias lines 312 and the microwave lines 314 may be viewed as examples of the external control circuitry 308 shown in FIG. 84.

Running a current through the flux bias lines 312, provided from the conductive contacts 320, enables the tuning of the frequency of the corresponding qubit elements 302 to which each line 312 is connected. For example, a magnetic field is created by running the current in a particular flux bias line 312. If such a magnetic field is in sufficient proximity to the qubit element 302, the magnetic field couples to the qubit element 302, thereby changing the spacing between the energy levels of the qubit element 302. This, in turn, changes the frequency of the qubit element 302 since the frequency is related to the spacing between the energy levels via Planck's equation. Provided there is sufficient multiplexing, different currents can be sent down each of the flux lines 312, allowing for independent tuning of the various qubit elements 302.

Typically, the qubit frequency may be controlled to bring the frequency either closer to or further away from another resonant element, such as a coupling resonator 316 as shown in FIG. 85 that connects two or more qubit elements 302 together. For example, if it is desired that a first qubit element 302 (e.g. the qubit element 302 shown on the left side of FIG. 85) and a second qubit element 302 (e.g. the qubit element 302 shown on the right side of FIG. 85) interact, via the coupling resonator 316 connecting these qubit elements, then both qubit elements 302 may be tuned at nearly the same frequency. In other scenarios, two qubit elements 302 could interact via a coupling resonator 316 at specific frequencies, but these three elements do not have to be tuned to be at nearly the same frequency with one another. Interactions between the qubit elements 302 can similarly be reduced or prevented by controlling the current in the appropriate flux bias lines. The state(s) of each qubit element 302 may be read by way of its corresponding readout resonator 318. As discussed below, the qubit element 302 may induce a resonant frequency in the readout resonator 318. This resonant frequency is then passed to the microwave lines 314 and communicated to the conductive contacts 322.

A readout resonator 318 may be provided for each qubit element. The readout resonator 318 may be a transmission line that includes a capacitive connection to ground on one side and is either shorted to ground on the other side (for a quarter-wavelength resonator) or has a capacitive connection to ground (for a half-wavelength resonator), which results in oscillations within the transmission line (resonance). The resonant frequency of the oscillations may be close to the frequency of the qubit element 302. The readout resonator 318 may be coupled to the qubit element 302 by being in sufficient proximity to the qubit element 302 (e.g., through capacitive or inductive coupling). Due to the coupling between the readout resonator 318 and the qubit element 302, changes in the state of the qubit element 302 may result in changes of the resonant frequency of the readout resonator 318. In turn, because the readout resonator 318 is in sufficient proximity to the microwave line 314, changes in the resonant frequency of the readout resonator 318 may induce changes in the current in the microwave line 314, and that current can be read externally via the conductive contacts 322.

The coupling resonator 316 may be used to couple different qubit elements together to realize quantum logic gates. The coupling resonator 316 may be similar to the readout resonator 318 in that it is a transmission line that may include capacitive connections to ground on both sides (for a half-wavelength resonator), which may result in oscillations within the coupling resonator 316. Each side of the coupling resonator 316 may be coupled (again, either capacitively or inductively) to a respective qubit element 302 by being in sufficient proximity to the qubit element 302. Because each side of the coupling resonator 316 couples with a respective different qubit element 302, the two qubit elements 302 may be coupled together through the coupling resonator 316. In this manner, a state of one qubit element 302 may depend on the state of the other qubit element 302, and vice versa. Thus, coupling resonators 316 may be employed to use a state of one qubit element 302 to control a state of another qubit element 302.

In some implementations, the microwave line 314 may be used to not only readout the state of the qubit elements 302 as described above, but also to control the state of the qubit elements 302. When a single microwave line 314 is used for this purpose, the line 314 may operate in a half-duplex mode in which, at some times, it is configured to readout the state of the qubit elements 302, and, at other times, it is configured to control the state of the qubit elements 302. In other implementations, microwave lines such as the line 314 shown in FIG. 85 may be used to only readout the state of the qubit elements as described above, while separate drive lines (such as the drive lines 324 shown in FIG. 85) may be used to control the state of the qubit elements 302. In such implementations, the microwave lines used for readout may be referred to as readout lines (e.g., the readout line 314), while microwave lines used for controlling the state of the qubit elements may be referred to as drive lines (e.g., the drive lines 324). The drive lines 324 may control the state of their respective qubit elements 302 by providing (e.g., using conductive contacts 326 as shown in FIG. 85) a microwave pulse at the qubit frequency, which in turn stimulates a transition between the states of the qubit element 302. By varying the length of this pulse, a partial transition can be stimulated, giving a superposition of the states of the qubit element 302.

Flux bias lines, microwave lines, coupling resonators, drive lines, and readout resonators, such as those described above, together form interconnects for supporting propagation of microwave signals. Further, any other connections for providing direct electrical interconnection between different quantum circuit elements and components, such as connections from Josephson junction electrodes to capacitor plates or to superconducting loops of superconducting quantum interference devices (SQUIDS) or connections between two ground lines of a particular transmission line for equalizing electrostatic potential on the two ground lines, are also referred to herein as interconnects. Electrical interconnections may also be provided between quantum circuit elements and components and non-quantum circuit elements, which may also be provided in a quantum circuit, as well as to electrical interconnections between various non-quantum circuit elements provided in a quantum circuit. Examples of non-quantum circuit elements that may be provided in a quantum circuit may include various analog and/or digital systems, e.g. analog-to-digital converters (ADCs), mixers, multiplexers, amplifiers, etc.

Coupling resonators and readout resonators may be configured for capacitive coupling to other circuit elements at one or both ends to have resonant oscillations, whereas flux bias lines and microwave lines may be similar to conventional microwave transmission lines because there is no resonance in these lines. Each one of these interconnects may be implemented as any suitable architecture of a microwave transmission line, such as a coplanar waveguide, a stripline, a microstrip line, or an inverted microstrip line. Typical materials that may be included in the interconnects may include aluminum, niobium, niobium nitride, titanium nitride, molybdenum rhenium, and niobium titanium nitride, all of which are particular types of superconductors. However, in various embodiments, other suitable superconductors and alloys of superconductors may be used as well.

In various embodiments, the interconnects as shown in FIG. 85 could have different shapes and layouts. For example, some interconnects may comprise more curves and turns while other interconnects may comprise fewer curves and turns, and some interconnects may comprise substantially straight lines. In some embodiments, various interconnects may intersect one another, in such a manner that they don't make an electrical connection, which can be done by using a bridge to bridge one interconnect over the other, for example.

In addition, FIG. 85 further illustrates ground contacts 328, connecting to the ground plane. Such ground contacts 328 may be used when a die supports propagation of microwave signals to suppress microwave parallel plate modes, cross-coupling between circuit blocks, and/or substrate resonant modes. In general, providing ground pathways may improve signal quality, enable fast pulse excitation, and improve the isolation between the different lines.

Only two ground contacts are labeled in FIG. 85 with the reference numeral 328, but all white circles shown throughout FIG. 85 may illustrate exemplary locations of ground conductive contacts. The illustration of the location and the number of the ground contacts 328 in FIG. 85 is purely illustrative and, in various embodiments, ground contacts 328 may be provided at different places, as known in microwave engineering. More generally, any number of qubit elements 302, flux bias lines 312, microwave lines 314, coupling resonators 316, readout resonators 318, drive lines 324, contacts 320, 322, 326, and 328, and other components discussed herein with reference to the superconducting quantum circuit 300 may be present.

While FIGS. 6 and 7 depict examples of quantum circuits comprising only two qubit elements 302, this is simply illustrative, and embodiments with any larger number of qubit elements are within the scope of the present disclosure. Furthermore, while FIGS. 6 and 7 may illustrate various features specific to transmon-type quantum devices, quantum circuits implementing other types of superconducting qubit elements may include any of the DDMs 500 disclosed herein.

Figure 86:
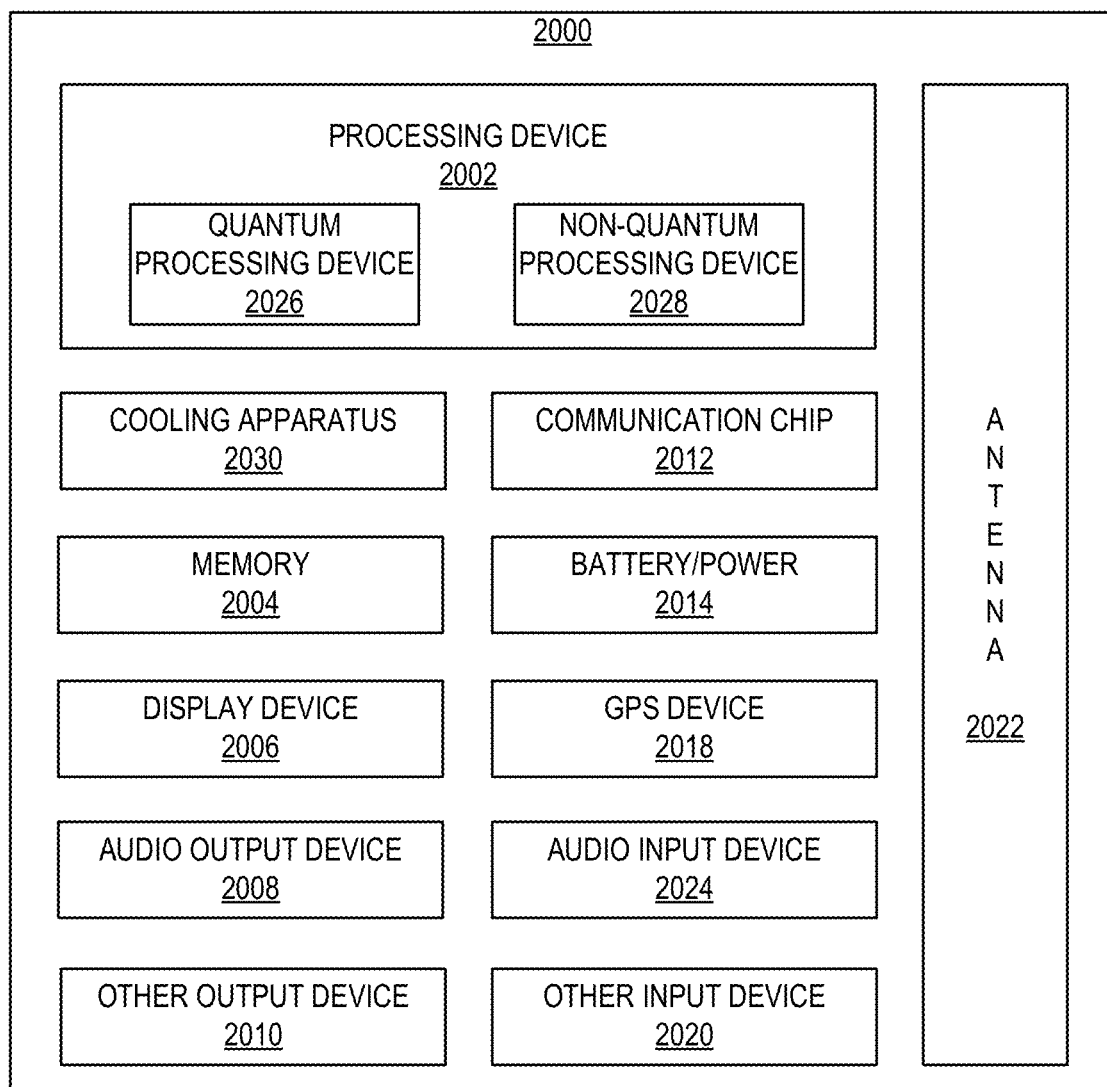
FIG. 86 is a block diagram of an example quantum computing device that may include any of the quantum dot devices disclosed herein, in accordance with various embodiments.

FIG. 86 is a block diagram of an example quantum computing device 2000 that may include any of the quantum dot devices disclosed herein. A number of components are illustrated in FIG. 86 as included in the quantum computing device 2000, but any one or more of these components may be omitted or duplicated, as suitable for the application. In some embodiments, some or all of the components included in the quantum computing device 2000 may be attached to one or more printed circuit boards (e.g., a motherboard). In some embodiments, various ones of these components may be fabricated onto a single system-on-a-chip (SoC) die. Additionally, in various embodiments, the quantum computing device 2000 may not include one or more of the components illustrated in FIG. 86, but the quantum computing device 2000 may include interface circuitry for coupling to the one or more components. For example, the quantum computing device 2000 may not include a display device 2006, but may include display device interface circuitry (e.g., a connector and driver circuitry) to which a display device 2006 may be coupled. In another set of examples, the quantum computing device 2000 may not include an audio input device 2024 or an audio output device 2008, but may include audio input or output device interface circuitry (e.g., connectors and supporting circuitry) to which an audio input device 2024 or audio output device 2008 may be coupled.

The quantum computing device 2000 may include a processing device 2002 (e.g., one or more processing devices). As used herein, the term "processing device" or "processor" may refer to any device or portion of a device that processes electronic data from registers and/or memory to transform that electronic data into other electronic data that may be stored in registers and/or memory. The processing device 2002 may include a quantum processing device 2026 (e.g., one or more quantum processing devices), and a non-quantum processing device 2028 (e.g., one or more non-quantum processing devices). The quantum processing device 2026 may include one or more of the quantum dot devices 100 disclosed herein, and may perform data processing by performing operations on the quantum dots that may be generated in the quantum dot devices 100, and monitoring the result of those operations. For example, as discussed above, different quantum dots may be allowed to interact, the quantum states of different quantum dots may be set or transformed, and the quantum states of quantum dots may be read (e.g., by another quantum dot). The quantum processing device 2026 may be a universal quantum processor, or specialized quantum processor configured to run one or more particular quantum algorithms. In some embodiments, the quantum processing device 2026 may execute algorithms that are particularly suitable for quantum computers, such as cryptographic algorithms that utilize prime factorization, encryption/decryption, algorithms to optimize chemical reactions, algorithms to model protein folding, etc. The quantum processing device 2026 may also include support circuitry to support the processing capability of the quantum processing device 2026, such as input/output channels, multiplexers, signal mixers, quantum amplifiers, and analog-to-digital converters.

As noted above, the processing device 2002 may include a non-quantum processing device 2028. In some embodiments, the non-quantum processing device 2028 may provide peripheral logic to support the operation of the quantum processing device 2026. For example, the non-quantum processing device 2028 may control the performance of a read operation, control the performance of a write operation, control the clearing of quantum bits, etc. The non-quantum processing device 2028 may also perform conventional computing functions to supplement the computing functions provided by the quantum processing device 2026. For example, the non-quantum processing device 2028 may interface with one or more of the other components of the quantum computing device 2000 (e.g., the communication chip 2012 discussed below, the display device 2006 discussed below, etc.) in a conventional manner, and may serve as an interface between the quantum processing device 2026 and conventional components. The non-quantum processing device 2028 may include one or more digital signal processors (DSPs), application-specific integrated circuits (ASICs), central processing units (CPUs), graphics processing units (GPUs), cryptoprocessors (specialized processors that execute cryptographic algorithms within hardware), server processors, or any other suitable processing devices.

The quantum computing device 2000 may include a memory 2004, which may itself include one or more memory devices such as volatile memory (e.g., dynamic random access memory (DRAM)), nonvolatile memory (e.g., read-only memory (ROM)), flash memory, solid state memory, and/or a hard drive. In some embodiments, the states of qubits in the quantum processing device 2026 may be read and stored in the memory 2004. In some embodiments, the memory 2004 may include memory that shares a die with the non-quantum processing device 2028. This memory may be used as cache memory and may include embedded dynamic random access memory (eDRAM) or spin transfer torque magnetic random access memory (STT-MRAM).

The quantum computing device 2000 may include a cooling apparatus 2030. The cooling apparatus 2030 may maintain the quantum processing device 2026 at a predetermined low temperature during operation to reduce the effects of scattering in the quantum processing device 2026. This predetermined low temperature may vary depending on the setting; in some embodiments, the temperature may be 5 Kelvin or less. In some embodiments, the non-quantum processing device 2028 (and various other components of the quantum computing device 2000) may not be cooled by the cooling apparatus 2030, and may instead operate at room temperature. The cooling apparatus 2030 may be, for example, a dilution refrigerator, a helium-3 refrigerator, or a liquid helium refrigerator.

In some embodiments, the quantum computing device 2000 may include a communication chip 2012 (e.g., one or more communication chips). For example, the communication chip 2012 may be configured for managing wireless communications for the transfer of data to and from the quantum computing device 2000. The term "wireless" and its derivatives may be used to describe circuits, devices, systems, methods, techniques, communications channels, etc., that may communicate data through the use of modulated electromagnetic radiation through a nonsolid medium. The term does not imply that the associated devices do not contain any wires, although in some embodiments they might not.

The communication chip 2012 may implement any of a number of wireless standards or protocols, including but not limited to Institute for Electrical and Electronic Engineers (IEEE) standards including Wi-Fi (IEEE 802.11 family), IEEE 802.16 standards (e.g., IEEE 802.16-2005 Amendment), Long-Term Evolution (LTE) project along with any amendments, updates, and/or revisions (e.g., advanced LTE project, ultramobile broadband (UMB) project (also referred to as "3GPP2"), etc.). IEEE 802.16 compatible Broadband Wireless Access (BWA) networks are generally referred to as WiMAX networks, an acronym that stands for Worldwide Interoperability for Microwave Access, which is a certification mark for products that pass conformity and interoperability tests for the IEEE 802.16 standards. The communication chip 2012 may operate in accordance with a Global System for Mobile Communication (GSM), General Packet Radio Service (GPRS), Universal Mobile Telecommunications System (UMTS), High Speed Packet Access (HSPA), Evolved HSPA (E-HSPA), or LTE network. The communication chip 2012 may operate in accordance with Enhanced Data for GSM Evolution (EDGE), GSM EDGE Radio Access Network (GERAN), Universal Terrestrial Radio Access Network (UTRAN), or Evolved UTRAN (E-UTRAN). The communication chip 2012 may operate in accordance with Code Division Multiple Access (CDMA), Time Division Multiple Access (TDMA), Digital Enhanced Cordless Telecommunications (DECT), Evolution-Data Optimized (EV-DO), and derivatives thereof, as well as any other wireless protocols that are designated as 3G, 4G, 5G, and beyond. The communication chip 2012 may operate in accordance with other wireless protocols in other embodiments. The quantum computing device 2000 may include an antenna 2022 to facilitate wireless communications and/or to receive other wireless communications (such as AM or FM radio transmissions).

In some embodiments, the communication chip 2012 may manage wired communications, such as electrical, optical, or any other suitable communication protocols (e.g., the Ethernet). As noted above, the communication chip 2012 may include multiple communication chips. For instance, a first communication chip 2012 may be dedicated to shorter-range wireless communications such as Wi-Fi or Bluetooth, and a second communication chip 2012 may be dedicated to longer-range wireless communications such as global positioning system (GPS), EDGE, GPRS, CDMA, WiMAX, LTE, EV-DO, or others. In some embodiments, a first communication chip 2012 may be dedicated to wireless communications, and a second communication chip 2012 may be dedicated to wired communications.

The quantum computing device 2000 may include battery/power circuitry 2014. The battery/power circuitry 2014 may include one or more energy storage devices (e.g., batteries or capacitors) and/or circuitry for coupling components of the quantum computing device 2000 to an energy source separate from the quantum computing device 2000 (e.g., AC line power).

The quantum computing device 2000 may include a display device 2006 (or corresponding interface circuitry, as discussed above). The display device 2006 may include any visual indicators, such as a heads-up display, a computer monitor, a projector, a touchscreen display, a liquid crystal display (LCD), a light-emitting diode display, or a flat panel display, for example.

The quantum computing device 2000 may include an audio output device 2008 (or corresponding interface circuitry, as discussed above). The audio output device 2008 may include any device that generates an audible indicator, such as speakers, headsets, or earbuds, for example.

The quantum computing device 2000 may include an audio input device 2024 (or corresponding interface circuitry, as discussed above). The audio input device 2024 may include any device that generates a signal representative of a sound, such as microphones, microphone arrays, or digital instruments (e.g., instruments having a musical instrument digital interface (MIDI) output).

The quantum computing device 2000 may include a GPS device 2018 (or corresponding interface circuitry, as discussed above). The GPS device 2018 may be in communication with a satellite-based system and may receive a location of the quantum computing device 2000, as known in the art.

The quantum computing device 2000 may include an other output device 2010 (or corresponding interface circuitry, as discussed above). Examples of the other output device 2010 may include an audio codec, a video codec, a printer, a wired or wireless transmitter for providing information to other devices, or an additional storage device.

The quantum computing device 2000 may include an other input device 2020 (or corresponding interface circuitry, as discussed above). Examples of the other input device 2020 may include an accelerometer, a gyroscope, a compass, an image capture device, a keyboard, a cursor control device such as a mouse, a stylus, a touchpad, a bar code reader, a Quick Response (QR) code reader, any sensor, or a radio frequency identification (RFID) reader.

The quantum computing device 2000, or a subset of its components, may have any appropriate form factor, such as a hand-held or mobile computing device (e.g., a cell phone, a smart phone, a mobile internet device, a music player, a tablet computer, a laptop computer, a netbook computer, an ultrabook computer, a personal digital assistant (PDA), an ultramobile personal computer, etc.), a desktop computing device, a server or other networked computing component, a printer, a scanner, a monitor, a set-top box, an entertainment control unit, a vehicle control unit, a digital camera, a digital video recorder, or a wearable computing device.

The following paragraphs provide examples of various ones of the embodiments disclosed herein.

Example 1 is a quantum computing device, including: qubit circuitry; an interconnect in conductive contact with the qubit circuitry; and a dielectric material proximate to the interconnect, wherein the dielectric material includes a diamondoid film.

Example 2 includes the subject matter of Example 1, and further specifies that the diamondoid film has an amorphous macrostructure.

Example 3 includes the subject matter of any of Examples 1-2, and further specifies that the diamondoid film has a diamondoid microstructure.

Example 4 includes the subject matter of any of Examples 1-3, and further specifies that the diamondoid film includes sp3 carbon bonds, and a proportion of the sp3 carbon bonds among carbon bonds in the diamondoid film is greater than 90 percent.

Example 5 includes the subject matter of Example 4, and further specifies that the proportion of sp3 carbon bonds among carbon bonds in the diamondoid film is greater than 95 percent.

Example 6 includes the subject matter of Example 5, and further specifies that the proportion of sp3 carbon bonds among carbon bonds in the diamondoid film is greater than 99 percent.

Example 7 includes the subject matter of any of Examples 1-6, and further specifies that the diamondoid film has a thickness that is less than 1 micron.

Example 8 includes the subject matter of Example 7, and further specifies that the diamondoid film has a thickness between 10 nanometers and 200 nanometers.

Example 9 includes the subject matter of Example 8, and further specifies that the diamondoid film has a thickness between 50 nanometers and 200 nanometers.

Example 10 includes the subject matter of any of Examples 1-9, and further specifies that the diamondoid film includes an adamantane.

Example 11 includes the subject matter of any of Examples 10, and further specifies that the diamondoid film includes an diallyladamantane, a divinyladamantane, or a dibromoadamantane.

Example 12 includes the subject matter of any of Examples 1-10, and further specifies that the diamondoid film is noncrystalline.

Example 13 includes the subject matter of any of Examples 1-12, and further specifies that the diamondoid film includes silicon and carbon.

Example 14 includes the subject matter of any of Examples 1-13, and further specifies that the diamondoid film includes a carbosilane.

Example 15 includes the subject matter of any of Examples 1-14, and further specifies that the qubit circuitry includes spin qubit-type quantum devices.

Example 16 includes the subject matter of any of Examples 1-15, and further specifies that the qubit circuitry includes superconducting qubit-type quantum devices.

Example 17 is a dielectric material, including: adamantane; and a carbosilane.

Example 18 includes the subject matter of Example 17, and further specifies that the dielectric material has an amorphous macrostructure.

Example 19 includes the subject matter of any of Examples 17-18, and further specifies that the dielectric material has a diamondoid microstructure.

Example 20 includes the subject matter of any of Examples 17-18, and further specifies that the dielectric material includes sp3 carbon bonds, and a proportion of the sp3 carbon bonds among carbon bonds in the dielectric material is greater than 90 percent.

Example 21 includes the subject matter of Example 20, and further specifies that the proportion of sp3 carbon bonds among carbon bonds in the dielectric material is greater than 95 percent.

Example 22 includes the subject matter of Example 21, and further specifies that the proportion of sp3 carbon bonds among carbon bonds in the dielectric material is greater than 99 percent.

Example 23 includes the subject matter of any of Examples 17-22, and further specifies that the dielectric material has a thickness that is less than 1 micron.

Example 24 includes the subject matter of Example 23, and further specifies that the dielectric material has a thickness between 10 nanometers and 200 nanometers.

Example 25 includes the subject matter of Example 24, and further specifies that the dielectric material has a thickness between 50 nanometers and 200 nanometers.

Example 26 includes the subject matter of any of Examples 17-25, and further specifies that the dielectric material includes an diallyladamantane, a divinyladamantane, or a dibromoadamantane.

Example 27 includes the subject matter of any of Examples 17-26, and further specifies that the dielectric material is noncrystalline.

Example 28 is a method of forming a diamondoid film, including: providing a support; providing one or more precursors, wherein the one or more precursors includes a carbosilane precursor; and treating the one or more precursors to form the diamondoid film on the support.

Example 29 includes the subject matter of Example 28, and further specifies that treating the one or more precursors to form the diamondoid film on the support includes: providing the one or more precursors to the support using atomic layer deposition or chemical vapor deposition.

Example 30 includes the subject matter of Example 29, and further specifies that the carbosilane precursor includes an oligometric mixture of hexaethoxytrisilacyclohexane and 1,3,5-trisilacyclohexane.

Example 31 includes the subject matter of Example 28, and further specifies that treating the one or more precursors to form the diamondoid film on the support includes: spin-coating the one or more precursors on the support.

Example 32 includes the subject matter of Example 31, and further specifies that the carbosilane precursor includes tetravinylsilane (TVS) or tetraallylsilane (TAS).

Example 33 includes the subject matter of any of Examples 31-32, and further specifies that treating the one or more precursors to form the diamondoid film on the support includes oligomerizing the one or more precursors.

Example 34 includes the subject matter of Example 28, and further specifies that the one or more precursors include an adamantane precursor.

Example 35 includes the subject matter of Example 34, and further specifies that the adamantane precursor includes a diallyladamantane, a divinyladamantane, or a dibromoadamantane.

Example 36 includes the subject matter of any of Examples 34-35, and further specifies that treating the one or more precursors to form the diamondoid film on the support includes: spin-coating the one or more precursors on the support.

Example 37 includes the subject matter of Example 36, and further specifies that treating the one or more precursors to form the diamondoid film on the support includes oligomerizing the one or more precursors.

Example 38 includes the subject matter of any of Examples 28-37, and further specifies that the diamondoid film has an amorphous macrostructure.

Example 39 includes the subject matter of any of Examples 28-38, and further specifies that the diamondoid film includes sp3 carbon bonds, and a proportion of the sp3 carbon bonds among carbon bonds in the diamondoid film is greater than 90 percent.

Example 40 includes the subject matter of Example 39, and further specifies that the proportion of sp3 carbon bonds among carbon bonds in the diamondoid film is greater than 95 percent.

Example 41 includes the subject matter of Example 40, and further specifies that the proportion of sp3 carbon bonds among carbon bonds in the diamondoid film is greater than 99 percent.

Example 42 includes the subject matter of any of Examples 28-41, and further specifies that the diamondoid film has a thickness that is less than 1 micron.

Example 43 includes the subject matter of Example 42, and further specifies that the diamondoid film has a thickness between 10 nanometers and 200 nanometers.

Example 44 includes the subject matter of Example 43, and further specifies that the diamondoid film has a thickness between 50 nanometers and 200 nanometers.

Example 45 includes the subject matter of any of Examples 28-44, and further specifies that the diamondoid film is noncrystalline.

The invention claimed is:

1. A quantum computing device, comprising:
   qubit circuitry;
   an interconnect in conductive contact with the qubit circuitry; and
   a dielectric material proximate to the interconnect, wherein the dielectric material includes a diamondoid film.

2. The quantum computing device of claim 1, wherein the diamondoid film has an amorphous macrostructure.

3. The quantum computing device of claim 1, wherein the diamondoid film has a diamondoid microstructure.

4. The quantum computing device of claim 1, wherein the diamondoid film includes sp3 carbon bonds, and a proportion of the sp3 carbon bonds among carbon bonds in the diamondoid film is greater than 90 percent.

5. The quantum computing device of claim 1, wherein the diamondoid film has a thickness that is less than 1 micron.

6. The quantum computing device of claim 1, wherein the diamondoid film includes an adamantane.

7. The quantum computing device of claim 1, wherein the diamondoid film is noncrystalline.

8. The quantum computing device of claim 1, wherein the diamondoid film includes silicon and carbon.

9. The quantum computing device of claim 1, wherein:
the quantum computing device further includes a quantum well stack,
the qubit circuitry includes a gate above the quantum well stack, and
the interconnect in conductive contact with the qubit circuitry includes an interconnect in conductive contact with the gate.

10. The quantum computing device of claim 9, wherein the interconnect is a conductive via.

11. The quantum computing device of claim 9, wherein the interconnect extends through the dielectric material.

12. The quantum computing device of claim 9, wherein the quantum computing device further includes a fin, and at least a portion of the quantum well stack is in the fin.

13. The quantum computing device of claim 9, wherein the quantum well stack includes a quantum well layer.

14. The quantum computing device of claim 9, wherein the quantum well stack further includes a barrier layer.

15. The quantum computing device of claim 1, wherein:
the quantum computing device further includes a Josephson Junction,
the qubit circuitry includes a control line coupled to the Josephson Junction, and
the interconnect in conductive contact with the qubit circuitry includes an interconnect in conductive contact with the control line.

16. The quantum computing device of claim 15, wherein the control line is one of a flux bias line, a readout line, or a drive line.

17. A quantum computing device, comprising:
a quantum processing device; and
a non-quantum processing device coupled to the quantum processing device,
wherein the quantum processing device includes:
    qubit circuitry,
    an interconnect in conductive contact with the qubit circuitry, and
    a dielectric material proximate to the interconnect, wherein the dielectric material includes a diamondoid film.

18. The quantum computing device of claim 17, further comprising a cooling apparatus.

19. A quantum computing device, comprising:
a quantum processing device; and
a non-quantum processing device coupled to the quantum processing device,
wherein the quantum processing device includes:
    a quantum well stack,
    plurality of gates above the quantum well stack,
    an insulator material above the plurality of gates, wherein the insulator material includes a diamondoid material, and
    an interconnect extending through the insulator material to a gate of the plurality of gates, wherein the interconnect is in conductive contact with the gate.

20. The quantum computing device of claim 19, wherein the gates include one or more plunger gates and one or more barrier gates.

* * * * *